(12) United States Patent
Bolli et al.

(10) Patent No.: US 8,592,460 B2
(45) Date of Patent: Nov. 26, 2013

(54) AMINO-PYRIDINE DERIVATIVES AS S1P1 /EDG1 RECEPTOR AGONISTS

(75) Inventors: Martin Bolli, Allschwil (CH); Boris Mathys, Egerkingen (CH); Claus Mueller, Weil am Rhein (DE); Oliver Nayler, Arlesheim (CH); Beat Steiner, Dornach (CH); Jorg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 654 days.

(21) Appl. No.: 12/531,374

(22) PCT Filed: Feb. 29, 2008

(86) PCT No.: PCT/IB2008/050742
§ 371 (c)(1),
(2), (4) Date: Sep. 15, 2009

(87) PCT Pub. No.: WO2008/114157
PCT Pub. Date: Sep. 25, 2008

(65) Prior Publication Data
US 2010/0087417 A1    Apr. 8, 2010

(30) Foreign Application Priority Data
Mar. 16, 2007  (WO) .................. PCT/IB2007/050921

(51) Int. Cl.
*A61K 31/4439* (2006.01)
*C07D 413/04* (2006.01)

(52) U.S. Cl.
USPC ........................................ 514/340; 546/269.4

(58) Field of Classification Search
USPC ........................................ 546/269.4; 514/340
See application file for complete search history.

(56) References Cited

U.S. PATENT DOCUMENTS

| | | | |
|---|---|---|---|
| 3,647,809 A | 3/1972 | Reiter et al. | |
| 5,708,180 A | 1/1998 | Beck et al. | |
| 7,605,171 B2 | 10/2009 | Colandrea et al. | |
| 7,605,269 B2 | 10/2009 | Bolli et al. | |
| 7,723,378 B2 | 5/2010 | Bolli et al. | |
| 7,750,040 B2 | 7/2010 | Bolli et al. | |
| 7,834,039 B2 * | 11/2010 | Hobson et al. | 514/364 |
| 7,846,964 B2 | 12/2010 | Bolli et al. | |
| 7,951,794 B2 | 5/2011 | Bolli et al. | |
| 7,981,924 B2 | 7/2011 | Bolli et al. | |
| 8,003,800 B2 | 8/2011 | Bolli et al. | |
| 8,133,910 B2 | 3/2012 | Bolli et al. | |
| 8,148,410 B2 | 4/2012 | Bolli et al. | |
| 8,178,562 B2 | 5/2012 | Bolli et al. | |
| 2004/0058894 A1 | 3/2004 | Doherty et al. | |
| 2007/0021443 A1 | 1/2007 | Ohlmeyer | |
| 2007/0043014 A1 | 2/2007 | Doherty et al. | |
| 2007/0270438 A1 | 11/2007 | Bhattacharya et al. | |
| 2008/0113961 A1 | 5/2008 | Nishi et al. | |
| 2008/0249093 A1 | 10/2008 | Colandrea et al. | |
| 2008/0306124 A1 | 12/2008 | Albert et al. | |
| 2009/0275554 A1 | 11/2009 | Habashita et al. | |
| 2010/0063108 A1 | 3/2010 | Bolli et al. | |
| 2010/0087495 A1 | 4/2010 | Bolli et al. | |
| 2010/0168005 A1 | 7/2010 | Bolli et al. | |
| 2010/0234346 A1 | 9/2010 | Bolli et al. | |
| 2010/0331372 A1 | 12/2010 | Bolli et al. | |
| 2011/0028448 A1 | 2/2011 | Bolli et al. | |
| 2011/0028449 A1 | 2/2011 | Bolli et al. | |
| 2011/0046170 A1 | 2/2011 | Bolli et al. | |
| 2011/0207704 A1 | 8/2011 | Cusack et al. | |
| 2011/0212998 A1 | 9/2011 | Bolli et al. | |
| 2012/0108638 A1 | 5/2012 | Bolli et al. | |

FOREIGN PATENT DOCUMENTS

| | | |
|---|---|---|
| DE | 10237883 | 3/2004 |
| EP | 0476646 | 3/1992 |
| EP | 0702003 | 6/1998 |
| EP | 1873153 | 1/2008 |
| JP | 2008120794 | 5/2008 |
| WO | WO 91/15583 | 10/1991 |
| WO | WO 99/46277 | 9/1999 |
| WO | WO 00/45799 | 8/2000 |
| WO | WO 0112627 | 2/2001 |
| WO | WO 02/068417 | 9/2002 |
| WO | WO 03/062248 | 7/2003 |
| WO | WO 03/062252 | 7/2003 |
| WO | WO 03/105771 | 12/2003 |
| WO | WO 2004/035538 | 4/2004 |
| WO | WO 2004/056789 | 7/2004 |
| WO | WO 2004/103279 | 12/2004 |
| WO | WO 2005/014525 | 2/2005 |
| WO | WO 2005/032465 | 4/2005 |
| WO | WO 2005/058848 | 6/2005 |
| WO | WO 2005115382 | 12/2005 |
| WO | WO 2006/047195 | 5/2006 |

(Continued)

OTHER PUBLICATIONS

Alvernhe et al; "Synthesis and Reactivity of 3-chloro-3-trifluoromethylacroleins: Stabilization of the Tetrahedral Intermediate in a Nucleophilic Vinylic "Substitution""; Bull. Soc. Chim. Fr.; 131, 1994, 167-172.

Biyouki, M.A.A., et al., Synthetic Communications, vol. 28, pp. 3817-3825 (1989).

Brain et al; "Novel Procedure for the Synthesis of 1,3,4-Oxadiazoles from 1,2-diacylhydrazinos Using Polymer-Supported Burgess Reagent under Microwave Conditions"; Tetrahedron Letters, 1999, pp. 3275-3278, vol. 40.

CAPLUS 2000:553399.

Chakraborti et al; "One-Pot Synthesis of Nitriles from Aldehydes Under Microwave Irradiation: Influence of the Medium and Mode of Microwave Irradiation on Product Formation"; Tetrahedron, 1999, pp. 13265-13268, vol. 55.

Cui et al; Design and Synthesis of Highly Constrained Factor Xa Inhibitors: Amidine-Substituted Bis(benzoyl)-[1,3]-diazepan-2-ones and Bis(benzylidene)-bis(gem-dimethyl)Cycloketones, Bioorganic Medicinal Chemistry, 2003, pp. 3379-3392, vol. II.

(Continued)

*Primary Examiner* — Patricia L Morris
(74) *Attorney, Agent, or Firm* — Hoxie & Associates LLC

(57) ABSTRACT

The invention relates to novel amino-pyridine derivatives, their preparation and their use as pharmaceutically active compounds. Said compounds particularly act as immunomodulating agents.

14 Claims, No Drawings

(56) References Cited

FOREIGN PATENT DOCUMENTS

| WO | WO 2006/097817 | 9/2006 |
|---|---|---|
| WO | WO 2006/100631 | 9/2006 |
| WO | WO 2006/114400 | 11/2006 |
| WO | WO 2006/115188 | 11/2006 |
| WO | WO 2006/131336 | 12/2006 |
| WO | WO 2007/001973 | 1/2007 |
| WO | WO 2007/085451 | 8/2007 |
| WO | WO 2007/098474 | 8/2007 |
| WO | WO 2007/132307 | 11/2007 |
| WO | WO 2008/029370 | 3/2008 |
| WO | WO 2008/029371 | 3/2008 |
| WO | WO 2008/037476 | 4/2008 |
| WO | WO 2008/076356 | 6/2008 |
| WO | WO 2008/091967 | 7/2008 |
| WO | WO 2009/043889 | 4/2009 |
| WO | WO 2009/043890 | 4/2009 |
| WO | WO 2009/151529 | 12/2009 |
| WO | WO 2011/007324 | 1/2011 |

OTHER PUBLICATIONS

Ecke et al; "Ortho-Alkylation of Aromatic Amines"; Journal of Organic Chemistry, 1957, pp. 639-642, vol. 22.
Fallahpour, R. A., Synthesis, No. 12, pp. 1665-1667 (2000).
Finch, N., et al., J. Med. Chem., vol. 23, pp. 1405-1410 (1980).
Furnster et al; "Iron Catalyzed Cross-Coupling Reactions"; J. Am. Chem. Soc., 124, 2002, 13856-13863.
Furnster et al; "Iron-Catalyzed Cross-coupling Reactions of Alkyl-grignard Reagents with Aryl Chlorides, Tosylates, and Triflates"; Angew. Chem.; 2002; vol. 41, No. 4, pp. 609-612.
Gangloff et al; "Synthesis of 3,5-disubstituted-1,2,4-Oxadiazoles Using Tetrabutylammonium Fluoride as a Mild and Efficient Catalyst", Tetrahedron Letters, 2001, pp. 1441-1443, vol. 42.
Garcia et al; "Synthesis, Biological Evaluation, and Three-Dimensional Quantitative Structure-Activity Relationship Study of Small-Molecule Positive Modulators of Adrenomedullin"; Journal of Medicinal Chemistry, 2005, pp. 4068-4075, vol. 48.
Gibson (Editor); Pharmaceutical Preformulation and Formulation; HIS Health Group, 2001.
Gierczyk, B., et al., Organic Preparations and Procedures Int., vol. 37, pp. 213-222 (2005).
Glennon et al; "B-Oxygenated Analogues of the 5-HT2A Serotonin Receptor Agonist 1-(4Bromo-2,5-dimethoxyphenyl)-2-aminopropane", Journal of Medicinal Chemistry, 2004, pp. 6034-6041, vol. 47.
Golub et al, "Molecular Classification of Cancer: Class Discovery and Class Prediction by Gene Expression Monitoring"; Science, 1999, vol. 286, 531-537.
Gould; "Salt Selection for Basic Drugs", International Journal of Pharmaceutics, 1986, pp. 201-217, vol. 33.
Grid-Alexa, L.C., et al., Synthesis, No. 4, pp. 619-628 (2006).
Gronowitz et al; "On the Synthesis of Branched Saturated Fatty Acids"; Lipids, vol. 28, 1993, 889-897.
Habermehl, N. C., et al., Inorganic Chem., vol. 68, pp. 7316-7321 (2003).
Hamze et al; "Synthesis of Various 3-Substituted 1,2,4-Oxadiazole Containing Chiral B- and a-Amino Acids from Fmoc-Protected Aspartic Acid"; J. Org. Chem., 68, 7316-7321.
Harris, M.C., J. Org. Chem., vol. 64, pp. 6019-6022 (1999).
Hla et al; "An Abundant Transcript Induced on Differentiating Human Endothelial Cells Encodes a Polypeptide with Structural Similarities to G-Protein-Coupled-Receptors"; The Journal of Biological Chemistry, 1990, pp. 9308-9313, vol. 265, No. 16.
John et al; "Reactions of (Difluoroamino) Difluoroacetonitrile and (Difluoroamino) Difluoroacetamidoxime", Inorganic Chemistry; 1988, pp. 3100-3104, vol. 27.
Kaboudin et al, "One-Pot Synthesis of 1,2,4-Oxadiazoles Mediated by Microwave Irradiation Under Solvent-Free Condition"; Heterocycles, 2003; pp. 2287-2292, vol. 60, No. 10.
Kaminski T. et al, J. Org. Chem., vol. 19, pp. 3855-3860 (2003).
Katz, R. B. et al., Syn. Communications, vol. 19, 317-325 (1989).
Kerins et al; "Generation of Substituted Styrenes via Suzuki Cross-Coupling or Aryl Halides with 2,4,6 Triymylcyclotriboroxane"; J. Org. Chem; 67, 2002, 4968-4971.
Khlestkin et al; "Recent Advances in the Application of A, O-dialkylhydroxylamines in Organic Chemistry"; Current Organic Chemistry, 7, 2003; 967-993.
Kiryanov et al; "Synthesis of 2-Alkoxy-Substituted Thlophenes, 1,3-Thiazoles, and Related S-Heterocycles via Lawesson's Reagent-Mediated Cyclization under Microwave Irradiation. Applications for Liquid Crystal Synthesis"; Journal of Organic Chemistry, 2001, pp. 7925-7929, vol. 66.
Knight et al; "Generation and Synthetic Utility of Dianions Derived from Thiophencarboxylic Acids"; J. Chem. Soc., Perkin Trans 1; 1983, 791-794.
Lala et al, "Role of Nitric Oxide in Tumor Progression: Lessons from Experimental Tumors"; Cancer and Metastasis Reviews (1998), 17, 91-106.
LaMattina, "The Synthesis of 2-Amino-4-(4-imidazolyl)pyridines"; J. Heterocyclic Chem.; 20; 1983; 533-538.
Matsushita H., et al., J. Org. Chem., vol. 47, pp. 4161-4165 (1982).
Mentzel et al; "N-Methoxy N-methyl amides (Weinred amides) in Modern Organic Synthesis", Journal fur Praktische Chemie Chiker-Zeitung; 339; 1997, 517-524.
Meyer et al; "Synthesis of New 1,2,4- and 1,3,4-Oxadiazole Derivatives"; Synthesis; 2003; pp. 899-905, No. 6.
Natarajan, S. R., Bioorg, & Med. Chem. Lett., vol. 13, pp. 273-276 (2003).
Notice of Allowance dated Jun. 13, 2012 for U.S. Appl. No. 12/310,763.
Office Action dated Dec. 2, 2011 for U.S. Appl. No. 12/310,763.
Office Action dated Dec. 6, 2011 for U.S. Appl. No. 12/310,801.
Office Action dated Feb. 17, 2012 for U.S. Appl. No. 12/673,918.
Office Action dated Jul. 24, 2012 for U.S. Appl. No. 12/920,569.
Office Action dated Jun. 11, 2012 for U.S. Appl. No. 12/673,918.
Office Action dated Jun. 27, 2012 for U.S. Appl. No. 12/310,801.
Office Action dated Jun. 7, 2011 for U.S. Appl. No. 12/310,763.
Office Action dated Mar. 1, 2012 for U.S. Appl. No. 12/310,763.
Office Action dated Oct. 8, 2010 for U.S. Appl. No. 12/310,763.
Paine, "A Convenient Synthesis of Nicotinate Esters from 3-cyanopyridones"; J. Heterocyclic; 1987; vol. 24, pp. 351-355.
Patani et al; "Bioisosterism: A Rational Approach in Drug Design"; Chem. Rev. 1996, vol. 96, No. 8, pp. 3147-3176.
Pesson et al; "Antibacteriens de Syntheses—Derives de L'acide Pipernidique", Eur. J. Med. Chem.; 15: 1980; 263-268.
Pierrat, P. et al., Synlett, No. 13, pp. 2319-2322 (2004).
Poulain et al; "Parallel Synthesis of 1,2,4-oxadiazoles from Carboxylic Acids Using an Improved, Uronium-based, Activation"; Tetrahedron Letters, 2001, pp. 1495-1498, vol. 42.
Remington, "The Science and Practice of Pharmacy", 21st Edition (2005), Part 5, "Pharmaceutical Manufacturing", Published by Lippincott Williams & Wilkins.
Roth et al; "2-4-Diamino-5-benzylyrimidines and Analogs as Antibacterial Agents"; J. Med. Chem.; 1988; vol. 31, No. 1; pp. 122-129.
Sato et al, "Synthesis and Evaluation of Substituted 4-alkoxy-2-aminopyridines as Novel Neuropeptide YI Receptor Antagonists", Bioorganic and Medicinal Chemistry Letters, 2004, pp. 1761-1764, vol. 14.
Silverman, "The Organic Chemistry of Drug Design and Drug Action"; 2004; Elsevier, pp. 29-32.
Silverman; "The Organic Chemistry of Drug Design and Drug Action"; 2004; Elsevier, pp. 9.
Singh et al; "The Growing Synthetic Utility of Weinreb's Amide"; Journal fur Praktische Chemie; 342; 2000; 340-347.
Srivastava et al; "Synthesis of 3-Aryl-5-[Thien-3-YL Methyl]-1,2,4-Oxadiazoles", Synthetic Communications, 1999, pp. 1437-1450, vol. 29.
Stauffer S. et al., Organic Letters, vol. 2, No. 10, pp. 1423-1426 (2000).
Suzuki et al; "Synthesis of the Selective 5-Hydroxytryptamine 4 (5-HT4) Receptor Agonist (+)-(S)-2-Chloro-5-methoxy-4-[5-(2-plperydylmethyl)-1,2,4-oxadiazol-3-yl]aniline"; Chem. Pharm. Bull.; 1999, pp. 120-122, vol. 47.

(56) References Cited

OTHER PUBLICATIONS

Trapani et al, "Propofol Analogues Synthesis, Relationships between Strucutre and Affinity at GABBA Receptor in Rat Brain, and Differential Electrophysiological Profile at Recombinant Human GABAA Receptors"; Journal of Medicinal Chemistry, 1998, pp. 1846-1854, vol. 41.

Tsukerman et al; "Basicity and Structure of .alpha., .beta.-unsaturated Ketones of a Heterocyclic Series. VII. Methyl-substituted Analogs of Chalcones"; Chemical Abstracts Service; XP0024673039, STN Database Accession No. 1971: 87024.

Waaaw S. et al., J. Org. Chem., vol. 61, pp. 7240-7241 (1996).

Wild et al; "Asymmetric Synthesis of (S)-(−)-acromelobic Acid"; Eur. J. Org. Chem.; 2003; pp. 4445-4440.

Wolfe J. P. et al., J. Org. Chem. vol. 65, pp. 1158-1174 (2000).

Xu et al; "Acyclic Analogues of Adenosine Biphosphates as P2Y Receptor Antagonists: Phosphate Substitution Leads to Multiple Pathways of Inhibition of Platelet Aggregation"; Journal of Medicinal Chemistry, 2002, pp. 5694-5709, vol. 45.

Yan et al, "Discovery of 3-arylpropionic Acids as Potent Agonists of Spingosine-1-phosphate Receptor-1 (S1P1) with High Selectivity Against All Other Known SIP Receptor Subtypes"; Bioorganic and Medicinal Chemistry Letters, 2006, pp. 3679-3683, vol. 16, No. 14.

Zhen et al, "Discovery of Potent 3,5-Diphenyl-1,2,4-oxadiazole Sphingosine-1-phosphate-1 (S1P1) Receptor Agonists with Exceptional Selectivity Against S1P1 and S1P", Journal of Medicinal Chemistry, 2005, pp. 6169-6173, vol. 48, No. 20.

Ziener, U. et al., Chemistry—A European Journal, vol. 6, pp. 41332-4139 (2000).

Bode et al; "Immune Regulation, Etc."; Arch. Immunol. Ther. Exp.; 60: 3-12; (2012).

Buzard et al; "Expert Opinion on Therapuetic Patents"; vol. 18, No. 10; pp. 1141-1159 (2008).

Gennaro, "Remington: The Science and Practice of Pharmacy", Table of Contents; 20th Edition, Philadelphia College of Pharmacy and Science 2003.

Greene et al, "Protective Groups in Organic Synthesis", Table of Contents; 3rd Edition, Wiley New York, 1991.

Gura; "Systems for Indentifying New Drugs are Often Faulty"; Cancer Models; Science, vol. 278, No. 5340, pp. 1041-1042; Nov. 1997.

Hu et al; "Sphingosine-1-phosphate, etc."; Mol. Biol. Rep.; 38:4225-4230 (2011).

Jo et al; "Spingosine-1-phosphate, Etc."; Kidney International; 73, 1220-1230; (2008).

Johnson et al; "Relationships Between Drug Acitvity in NCI Preclinical In Vitro and In Vivo Models and Early Clinical Trials"; British Journal of Cancer; 64(10): 1524-1431; (2001).

Kocienski, "Protecting Groups", Thieme Stuggart, 1994; Introduction.

Meyer Zu Heringdorf et al; "Pharmacology of the Sphingosine-1-Phosphate Signalling System"; Sphingolipids: Basic Science and Drug Development; Handbook of Experimental Pharmacology 215, pp. 239-253; 2013.

Notice of Allowance dated Jun. 20, 2012 for U.S. Appl. No. 12/738,110.

Notice of Allowance dated Nov. 18, 2011 for U.S. Appl. No. 12/747,280.

Notice of Allowance dated Nov. 28, 2012 for U.S. Appl. No. 12/920,574.

Notice of Allowance dated Sep. 26, 2011 for U.S. Appl. No. 12/442,203.

Office Action—Final dated Feb. 7, 2013 for U.S. Appl. No. 12/637,918.

Office Action—Final dated Nov. 8, 2012 for U.S. Appl. No. 12/310,801.

Office Action—Non-Final dated Mar. 13, 2012 for U.S. Appl. No. 12/738,110.

Office Action—Restriction dated Apr. 26, 2013 for U.S. Appl. No. 13/383,619.

Office Action—Restriction dated Jul. 24, 2012 for U.S. Appl. No. 12/920,569.

Office Action—Restriction dated May 24, 2012 for U.S. Appl. No. 12/920,656.

Office Action dated Feb. 8, 2013 for U.S. Appl. No. 12/920,656.

Office Action dated Jan. 4, 2013 for U.S. Appl. No. 12/310,801.

Office Action dated Oct. 31, 2012 for U.S. Appl. No. 12/920,656.

Roberts et al; "Sphingosine 1-phosphate Receptor Agonists: A Patent Review"; Expert Opinion; The Scripps Research Institute, Dept. of Chemistry; 2013; pp. 1-25.

Robinson; "Medical Therapy of Inflammatory Bowel Disease for the 21st Century"; Eur. J. Sug. 164, Suppl. 582, pp. 90-98 (1998).

Simone; "Oncology: Introduction"; Cecil Textbook of Medicine, 20th Edition; vol. 1; pp. 1004-1010; (1996).

Spiegel et al; "Nature Reviews Immunology"; vol. 11, No. 6; pp. 403-415; Jun. 2011.

Van Der Giet et al; "Relevance and Potential, Etc."; Biol. Chem.; 389, pp. 1381-1390; (2008).

Notice of Allowance dated Jun. 19, 2013 for U.S. Appl. No. 12/310,801.

Advisory Action dated Apr. 16, 2013 for U.S. Appl. No. 12/310,801.

Notice of Allowance dated Jul. 23, 2013 for U.S. Appl. No. 12/673,918.

Supp. Notice of Allowance dated Oct. 17, 2013 for U.S. Appl. No. 12/673,918.

Office Action—Final dated May 23, 2013 for U.S. Appl. No. 12/920,569.

Advisory Action dated May 16, 2013 for U.S. Appl. No. 12/920,656.

Notice of Allowance dated Jun. 24, 2013 for U.S. Appl. No. 12/920,656.

\* cited by examiner

AMINO-PYRIDINE DERIVATIVES AS S1P1 /EDG1 RECEPTOR AGONISTS

CROSS REFERENCE TO RELATED APPLICATIONS

This application is a United States Application under 35 U.S.C. 371 claiming benefit of PCT Application No. PCT/IB2008/050742, filed on Feb. 29, 2008, which claims the benefit of PCT Application No. PCT/IB2007/050921, filed on Mar. 16, 2007.

FIELD OF THE INVENTION

The present invention relates to S1P1/EDG1 receptor agonists of formula (I) and their use as active ingredients in the preparation of pharmaceutical compositions. The invention also concerns related aspects including processes for the preparation of the compounds, pharmaceutical compositions containing a compound of the formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO 91/15583 published 17 Oct. 1991; WO 99/46277 published 16 Sep. 1999. The potency and efficacy of the compounds of formula (I) are assessed using a GTPγS assay to determine $EC_{50}$ values and by measuring the circulating lymphocytes in the rat after oral administration, respectively (see in Examples).

i) The invention relates to novel amino-pyridine compounds of the formula (I),

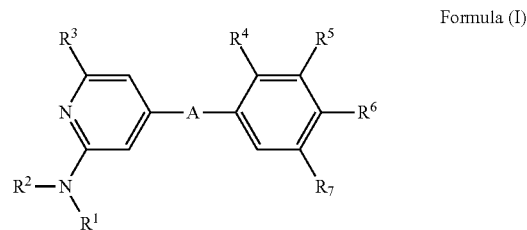

Formula (I)

wherein
A represents wherein the asterisks indicate the bond that is linked to the pyridine group of formula (I);
$R^1$ represents hydrogen, or $C_{1-3}$-alkyl;
$R^2$ represents $C_{1-4}$-alkyl; or
$R^1$ and $R^2$, together with the nitrogen atom to which they are attached, form a pyrrolidine, piperidine, or morpholine ring, such as especially a pyrrolidine ring;
$R^3$ represents $C_{1-4}$-alkyl, or chloro;
$R^4$ represents hydrogen, $C_{1-4}$-alkyl, $C_{1-3}$-alkoxy, or halogen;
$R^5$ represents hydrogen, $C_{1-4}$-alkyl, $C_{1-3}$-alkoxy, or halogen;
$R^6$ represents hydrogen, hydroxy-$C_{1-5}$-alkyl, 2,3-dihydroxypropyl, di-(hydroxy-$C_{1-4}$-alkyl)-$C_{1-4}$-alkyl, —$CH_2$—$(CH_2)_k$— —$NR^{61}R^{62}$, —$CH_2$—$(CH_2)_k$—$NHSO_2R^{63}$, —$(CH_2)_n$ $CH(OH)$—$CH_2$—$NHSO_2R^{63}$, —$CH_2$—$(CH_2)_k$—$NHCOR^{64}$, —$(CH_2)_n CH(OH)$—$CH_2$—$NHCOR^{64}$, —$CH_2$—$(CH_2)_n$—$CONR^{61}R^{62}$, —$CO$—$NHR^{61}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n CH(OH)$—$CH_2$—$NR^{61}R^{62}$, hydroxy, $C_{1-4}$-alkoxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{61}R^{62}$, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, —$OCH_2$—$CH(OH)$—$CH_2$—$NR^{61}R^{62}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, —$OCH_2$—$(CH_2)_m$—$NHSO_2R^{63}$, —$OCH_2$—$CH(OH)$—$CH_2$—$NHSO_2R^{63}$, —$OCH_2$—$(CH_2)_m$—$NHCOR^{64}$, —$OCH_2$—$CH(OH)$—$CH_2$—$NHCOR^{64}$, —$NR^{61}R^{62}$, —$NHCO$—$R^{61}$, or —$SO_2NHR^{61}$;
$R^{61}$ represents hydrogen, $C_{1-3}$-alkyl, 2-hydroxyethyl, 2-hydroxy-1-hydroxymethyl-ethyl, 2,3-dihydroxypropyl, carboxymethyl, ($C_{1-5}$-alkylcarboxy)methyl, 2-carboxyethyl, 2-($C_{1-5}$-alkylcarboxy)ethyl, or 2-aminoethyl;
$R^{62}$ represents hydrogen, methyl, or ethyl;
$R^{63}$ represents $C_{1-3}$-alkyl, methylamino, ethylamino, or dimethylamino;
$R^{64}$ represents hydroxy-$C_{1-2}$-alkyl, or $R^{65}R^{66}N$—$C_{1-2}$-alkyl;
$R^{65}$ and $R^{66}$ independently represent hydrogen, or methyl;
k represents the integer 1, 2, or 3;
m represents the integer 1 or 2;
n represents 0, 1, or 2; and
$R^7$ represents hydrogen, $C_{1-4}$-alkyl, or halogen.

The general terms used hereinbefore and hereinafter preferably have, within this disclosure, the following meanings, unless otherwise indicated:

The term $C_{x-y}$-alkyl, x and y being an integer, means saturated, branched or straight chain alkyl groups with x to y carbon atoms. Likewise, the term $C_{1-5}$-alkyl means saturated, branched or straight chain alkyl groups with one to five carbon atoms. Examples of $C_{1-5}$-alkyl groups are methyl, ethyl, n-propyl, iso-propyl, n-butyl, iso-butyl, n-pentyl, and iso-pentyl (preferably methyl, ethyl, n-propyl, iso-propyl, or iso-butyl). Likewise, the term $C_{1-4}$-alkyl means saturated, branched or straight chain alkyl groups with one to four carbon atoms. Examples of $C_{1-4}$-alkyl groups are methyl, ethyl, n-propyl, iso-propyl, n-butyl, and iso-butyl (preferably methyl, ethyl, n-propyl, iso-propyl, or iso-butyl). Likewise, the term $C_{1-3}$-alkyl means saturated, branched or straight chain alkyl groups with one to three carbon atoms. Examples of $C_{1-3}$-alkyl groups are methyl, ethyl, n-propyl, and iso-propyl (preferably methyl, or ethyl). Likewise, the term $C_{1-2}$-alkyl represents a methyl, or ethyl group.

The term $C_{x-y}$-alkoxy, x and y being an integer, means an R—O group, wherein R is a saturated, branched or straight chain alkyl group with x to y carbon atoms. Likewise, the term $C_{1-4}$-alkoxy means an R—O group, wherein R is a $C_{1-4}$-alkyl. Examples of $C_{1-4}$-alkoxy groups are methoxy, ethoxy, propoxy, iso-propoxy, and iso-butoxy (preferably methoxy). Likewise, the term $C_{2-5}$-alkoxy means an R—O group, wherein R is a $C_{2-5}$-alkyl. Examples of $C_{2-5}$-alkoxy groups are ethoxy, propoxy, iso-propoxy, iso-butoxy, and iso-pentoxy (preferably ethoxy).

The term halogen means fluoro, chloro, bromo or iodo (preferably fluoro or chloro; especially preferred chloro).

ii) A further embodiment of the invention relates to amino-pyridine derivatives according to embodiment i), wherein A represents wherein the asterisks indicate the bond that is linked to the pyridine group of formula (I).

iii) Another embodiment of the invention relates to amino-pyridine derivatives according to embodiment i), wherein A represents wherein the asterisks indicate the bond that is linked to the pyridine group of formula (I).

iv) Another embodiment of the invention relates to amino-pyridine derivatives according to embodiment i), wherein A represents

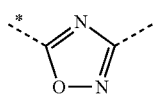

wherein the asterisk indicates the bond that is linked to the pyridine group of formula (I).

v) Another embodiment of the invention relates to aminopyridine derivatives according to embodiment i), wherein A represents

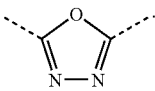

vi) Another embodiment of the invention relates to aminopyridine derivatives according to any one of the embodiments i) to v), wherein $R^1$ represents hydrogen, methyl or ethyl.

vii) Another embodiment of the invention relates to aminopyridine derivatives according to any one of the embodiments i) to v), wherein $R^1$ represents methyl or ethyl.

viii) Another embodiment of the invention relates to aminopyridine derivatives according to any one of the embodiments i) to vii), wherein $R^2$ represents $C_{1-3}$-alkyl.

ix) Another embodiment of the invention relates to aminopyridine derivatives according to any one of the embodiments i) to vii), wherein $R^2$ represents ethyl or isopropyl.

x) Another embodiment of the invention relates to aminopyridine derivatives according to any one of the embodiments i) to ix), wherein $R^3$ represents $C_{1-4}$-alkyl.

xi) Another embodiment of the invention relates to aminopyridine derivatives according to any one of the embodiments i) to ix), wherein $R^3$ represents $C_{1-2}$-alkyl.

xii) Another embodiment of the invention relates to aminopyridine derivatives according to any one of the embodiments i) to ix), wherein $R^3$ represents methyl.

xiii) Another embodiment of the invention relates to aminopyridine derivatives according to any one of the embodiments i) to xii), wherein $R^4$ represents methoxy, and $R^5$ and $R^7$ represent hydrogen.

xiv) Another embodiment of the invention relates to aminopyridine derivatives according to any one of the embodiments i) to xii), wherein $R^4$ represents hydrogen; $R^5$ represents $C_{1-3}$-alkyl, or methoxy; and $R^7$ represents $C_{1-2}$-alkyl, or chloro.

xv) Another embodiment of the invention relates to aminopyridine derivatives according to any one of the embodiments i) to xii), wherein $R^4$ represents hydrogen; $R^5$ represents methyl, or ethyl; and $R^7$ represents methyl.

xvi) Another embodiment of the invention relates to aminopyridine derivatives according to any one of the embodiments i) to xii), wherein $R^4$ represents hydrogen; $R^5$ represents methoxy, or methyl; and $R^7$ represents chloro.

xvii) Another embodiment of the invention relates to aminopyridine derivatives according to any one of the embodiments i) to xvi), wherein $R^6$ represents hydrogen, 2,3-dihydroxypropyl, di-(hydroxy-$C_{1-4}$-alkyl)-$C_{1-4}$-alkyl, —$CH_2$—$(CH_2)_k$—$NHSO_2R^{63}$, —$(CH_2)_n CH(OH)$—$CH_2$—$NHSO_2R^{63}$, —$CH_2$—$(CH_2)_k$—$NHCOR^{64}$, —$(CH_2)_n CH(OH)$—$CH_2$—$NHCOR^{64}$, —$CH_2$—$(CH_2)_n$—$CONR^{61}R^{62}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n CH(OH)$—$CH_2$—$NR^{61}R^{62}$, hydroxy, $C_{1-4}$-alkoxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{61}R^{62}$, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, —$OCH_2$—$CH(OH)$—$CH_2$—$NR^{61}R^{62}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, —$OCH_2$—$(CH_2)_m$—$NHSO_2R^{63}$, —$OCH_2$—$CH(OH)$—$CH_2$—$NHSO_2R^{63}$, —$OCH_2$—$(CH_2)_m$—$NHCOR^{64}$, —$OCH_2$—$CH(OH)$—$CH_2$—$NHCOR^{64}$, or —$NR^{61}R^{62}$.

xviii) Another embodiment of the invention relates to aminopyridine derivatives according to any one of the embodiments i) to xvi), wherein $R^6$ represents hydrogen, 2,3-dihydroxypropyl, di-(hydroxy-$C_{1-4}$-alkyl)-$C_{1-4}$-alkyl, —$CH_2$—$(CH_2)_k$—$NHSO_2R^{63}$, —$(CH_2)_n CH(OH)$—$CH_2$—$NHSO_2R^{63}$, —$CH_2$—$(CH_2)_k$—$NHCOR^{64}$, —$(CH_2)_n CH(OH)$—$CH_2$—$NHCOR^{64}$, —$CH_2$—$(CH_2)_n$—$CONR^{61}R^{62}$, —$(CH_2)_n CH(OH)$—$CH_2$—$NR^{61}R^{62}$, hydroxy, $C_{1-4}$-alkoxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{61}R^{62}$, —$OCH_2$—$CH(OH)$—$CH_2$—$NR^{61}R^{62}$, —$OCH_2$—$(CH_2)_m$—$NHSO_2R^{63}$, —$OCH_2$—$CH(OH)$—$CH_2$—$NHSO_2R^{63}$, —$OCH_2$—$(CH_2)_m$—$NHCOR^{64}$, —$OCH_2$—$CH(OH)$—$CH_2$—$NHCOR^{64}$, or —$NR^{61}R^{62}$.

xix) Another embodiment of the invention relates to aminopyridine derivatives according to any one of the embodiments i) to xvi), wherein $R^6$ represents 2,3-dihydroxypropyl, —$(CH_2)_n CH(OH)$—$CH_2$—$NHSO_2R^{63}$, —$CH_2$—$(CH_2)_k$—$NHCOR^{64}$, —$CH_2$—$(CH_2)_k$—$NHSO_2R^{63}$, —$(CH_2)_n CH(OH)$—$CH_2$—$NHCOR^{64}$, —$CH_2$—$(CH_2)_n$—$CONR^{61}R^{62}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NHSO_2R^{63}$, —$OCH_2$—$CH(OH)$—$CH_2$—$NHSO_2R^{63}$, —$OCH_2$—$(CH_2)_m$—$NHCOR^{64}$, or —$OCH_2$—$CH(OH)$—$CH_2$—$NHCOR^{64}$.

xx) Another embodiment of the invention relates to aminopyridine derivatives according to any one of the embodiments i) to xvi), wherein $R^6$ represents —$CH_2$—$(CH_2)_n$—$CONR^{61}R^{62}$, hydroxy-$C_{2-5}$-alkoxy, di-(hydroxy-$C_{1-4}$-alkyl)-$C_{1-4}$-alkoxy, 2,3-dihydroxy-propoxy, —$OCH_2$—$(CH_2)_m$—$NHSO_2R^{63}$, —$OCH_2$—$CH(OH)$—$CH_2$—$NHSO_2R^{63}$, —$OCH_2$—$(CH_2)_m$—$NHCOR^{64}$, or —$OCH_2$—$CH(OH)$—$CH_2$—$NHCOR^{64}$.

xxi) Another embodiment of the invention relates to aminopyridine derivatives according to any one of the embodiments i) to xvi), wherein $R^6$ represents hydroxy, $C_{1-4}$-alkoxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{61}R^{62}$, —$OCH_2$—$CH(OH)$—$CH_2$—$NR^{61}R^{62}$, —$OCH_2$—$(CH_2)_m$—$NHSO_2R^{63}$, —$OCH_2$—$CH(OH)$—$CH_2$—$NHSO_2R^{63}$, —$OCH_2$—$(CH_2)_m$—$NHCOR^{64}$, or —$OCH_2$—$CH(OH)$—$CH_2$—$NHCOR^{64}$.

xxii) Another embodiment of the invention relates to aminopyridine derivatives according to any one of the embodiments i) to xvi), wherein $R^6$ represents —$CH_2$—$(CH_2)_n$—$CONR^{61}R^{62}$, 2,3-dihydroxy-propoxy, or —$OCH_2$—$CH(OH)$—$CH_2$—$NHCOR^{64}$.

xxiii) Another embodiment of the invention relates to amino-pyridine derivatives according to any one of the embodiments i) to xvi), wherein $R^6$ represents —$CH_2$—$(CH_2)_n$—$CONR^{61}R^{62}$.

xxiv) Another embodiment of the invention relates to amino-pyridine derivatives according to any one of the embodiments i) to xvi), wherein $R^6$ represents 2,3-dihydroxy-propoxy, or —$OCH_2$—$CH(OH)$—$CH_2$—$NHCOR^{64}$.

xxv) Another embodiment of the invention relates to amino-pyridine derivatives according to any one of the embodiments i) to xxiii), wherein $R^{61}$ represents hydrogen, 2-carboxyethyl, or 2-aminoethyl.

xxvi) Another embodiment of the invention relates to amino-pyridine derivatives according to any one of the embodiments i) to xxiii) and xxv), wherein $R^{62}$ represents hydrogen.

xxvii) Another embodiment of the invention relates to amino-pyridine derivatives according to any one of the embodiments i) to xxi), wherein $R^{63}$ represents methyl, or methylamino.

xxviii) Another embodiment of the invention relates to amino-pyridine derivatives according to any one of the embodiments i) to xxii) and xxiv), wherein $R^{64}$ represents hydroxymethyl.

xxix) Another embodiment of the invention relates to amino-pyridine derivatives according to any one of the embodiments i) to xx) and xxii) to xxiii), wherein n represents the integer 1.

xxx) Another embodiment of the invention relates to amino-pyridine derivatives according to any one of the embodiments i) to xix), wherein k represents the integer 1 or 2.

xxxi) A further embodiment of the invention relates to amino-pyridine derivatives according to embodiment i), wherein A represents

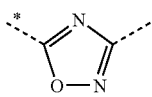

wherein the asterisk indicates the bond that is linked to the pyridine group of formula (I);
$R^1$ represents $C_{1-3}$-alkyl;
$R^2$ represents $C_{1-4}$-alkyl; or
$R^1$ and $R^2$, together with the nitrogen atom to which they are attached, form a pyrrolidine ring;
$R^3$ represents $C_{1-4}$-alkyl;
$R^4$ represents hydrogen;
$R^5$ represents $C_{1-4}$-alkyl;
$R^6$ represents —$CH_2$—$(CH_2)_n$—$CONR^{61}R^{62}$, hydroxy, 2,3-dihydroxy-propoxy, —$OCH_2$—$CH(OH)$—$CH_2$—$NR^{61}R^{62}$, or —$OCH_2$—$CH(OH)$—$CH_2$—$NHCOR^{64}$;
$R^{61}$ represents hydrogen, 2-carboxyethyl, or 2-aminoethyl;
$R^{62}$ represents hydrogen;
$R^{64}$ represents hydroxy-$C_{1-2}$-alkyl;
n represents 1; and
$R^7$ represents $C_{1-4}$-alkyl.

xxxii) A further embodiment of the invention relates to amino-pyridine derivatives according to embodiment i) wherein A represents

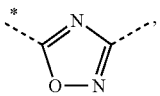 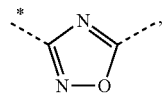

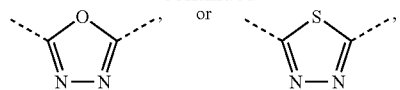

wherein the asterisks indicate the bond that is linked to the pyridine group of formula (I);
$R^1$ represents hydrogen, or $C_{1-3}$-alkyl;
$R^2$ represents $C_{1-4}$-alkyl; or
$R^1$ and $R^2$, together with the nitrogen atom to which they are attached, form a pyrrolidine or morpholine ring, such as especially a pyrrolidine ring;
$R^3$ represents $C_{1-4}$-alkyl, or chloro;
$R^4$ represents hydrogen, $C_{1-4}$-alkyl, $C_{1-3}$-alkoxy, or halogen;
$R^5$ represents hydrogen, $C_{1-4}$-alkyl, $C_{1-3}$-alkoxy, or halogen;
$R^6$ represents hydrogen, hydroxy-$C_{1-5}$-alkyl (such as hydroxymethyl or 2-hydroxyethyl), —$CH_2$—$(CH_2)_k$—$NR^{61}R^{62}$, —$CH_2$—$(CH_2)_k$—$NHSO_2R^{63}$, —$(CH_2)_n$CH(OH)—$CH_2$—$NHSO_2R^{63}$, —$CH_2$—$(CH_2)_k$—$NHCOR^{64}$, —$CH_2$—$(CH_2)_n$—$CONR^{61}R^{62}$, —$CO$—$NHR^{61}$, 1-(3-carboxy-azetidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n$CH(OH)—$CH_2$—$NR^{61}R^{62}$, hydroxy, $C_{1-4}$-alkoxy, hydroxy-$C_{2-5}$-alkoxy (such as 2-hydroxy-ethoxy), di-(hydroxy-$C_{1-4}$-alkyl)-$C_{1-4}$-alkoxy (such as 1-hydroxymethyl-2-hydroxy-ethoxy or 2-hydroxymethyl-3-hydroxy-n-propoxy), 2,3-dihydroxy-propoxy, 2-hydroxy-3-methoxy-propoxy, —$OCH_2$—$(CH_2)_m$—$NR^{61}R^{62}$, 2-[(azetidine-3-carboxylic acid)-1-yl]-ethoxy, 2-[(azetidine-3-carboxylic acid $C_{1-5}$-alkylester)-1-yl]-ethoxy (such as 2-[(azetidine-3-carboxylic acid methylester)-1-yl]-ethoxy), 2-[(pyrrolidine-3-carboxylic acid)-1-yl]-ethoxy, 2-[(pyrrolidine-3-carboxylic acid $C_{1-5}$-alkylester)-1-yl]-ethoxy (such as 2-[(pyrrolidine-3-carboxylic acid methylester)-1-yl]-ethoxy), —$OCH_2$—$CH(OH)$—$CH_2$—$NR^{61}R^{62}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy (such as 3-[(azetidine-3-carboxylic acid methylester)-1-yl]-2-hydroxypropoxy), 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy (such as 2-hydroxy-3-[(pyrrolidine-3-carboxylic acid methylester)-1-yl]-propoxy), 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy (such as 2-hydroxy-3-[(pyrrolidine-2-carboxylic acid methylester)-1-yl]-propoxy), —$OCH_2$—$(CH_2)_m$—$NHSO_2R^{63}$, —$OCH_2$—$CH(OH)$—$CH_2$—$NHSO_2R^{63}$, —$OCH_2$—$(CH_2)_m$—$NHCOR^{64}$, —$OCH_2$—$CH(OH)$—$CH_2$—$NHCOR^{64}$, —$NR^{61}R^{62}$, or —$NHCO$—$R^{61}$;
$R^{61}$ represents hydrogen, $C_{1-3}$-alkyl, 2-hydroxyethyl, 2,3-dihydroxypropyl, carboxymethyl, $(C_{1-5}$-alkylcarboxy)methyl (such as (ethylcarboxy)methyl), 2-carboxyethyl, or 2-aminoethyl;
$R^{62}$ represents hydrogen;
$R^{63}$ represents $C_{1-3}$-alkyl, or dimethylamino;
$R^{64}$ represents hydroxy-$C_{1-2}$-alkyl, or $R^{65}R^{66}N$—$C_{1-2}$-alkyl;
$R^{65}$ and $R^{66}$ independently represent hydrogen, or methyl;
k and m represent the integer 1;
n represents 0 or 1; and
$R^7$ represents hydrogen, $C_{1-4}$-alkyl, or halogen.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of formula (I) is to be understood as referring also to salts, especially pharmaceutically acceptable salts, of a compound of formula (I), as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Examples of preferred compounds are selected from the group consisting of:
(R)-3-{4-[5-(2-diethylamino-6-ethyl-pyridin-4-yl)-[1,2,4]oxadiazol-3-yl]-2-ethyl-6-methyl-phenoxy}-propane-1,2-diol;
(S)-3-{4-[5-(2-diethylamino-6-ethyl-pyridin-4-yl)-[1,2,4]oxadiazol-3-yl]-2-ethyl-6-methyl-phenoxy}-propane-1,2-diol;
(R)-3-{4-[5-(2-diethylamino-6-methyl-pyridin-4-yl)-[1,2,4]oxadiazol-3-yl]-2-ethyl-6-methyl-phenoxy}-propane-1,2-diol;
(S)-3-{4-[5-(2-diethylamino-6-methyl-pyridin-4-yl)-[1,2,4]oxadiazol-3-yl]-2-ethyl-6-methyl-phenoxy}-propane-1,2-diol;
(R)-3-(2-ethyl-4-{5-[2-(ethyl-methyl-amino)-6-methyl-pyridin-4-yl]-[1,2,4]oxadiazol-3-yl}-6-methyl-phenoxy)-propane-1,2-diol;
(S)-3-(2-ethyl-4-{5-[2-(ethyl-methyl-amino)-6-methyl-pyridin-4-yl]-[1,2,4]oxadiazol-3-yl}-6-methyl-phenoxy)-propane-1,2-diol;
(R)-3-{4-[5-(2-diethylamino-6-methyl-pyridin-4-yl)-[1,2,4]oxadiazol-3-yl]-2,6-dimethyl-phenoxy}-propane-1,2-diol;
(S)-3-{4-[5-(2-diethylamino-6-methyl-pyridin-4-yl)-[1,2,4]oxadiazol-3-yl]-2,6-dimethyl-phenoxy}-propane-1,2-diol;
N—((R)-3-{4-[5-(2-dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide;
N—((S)-3-{4-[5-(2-dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide;
(R)-3-{4-[5-(2-diethylamino-6-methyl-pyridin-4-yl)-[1,2,4]oxadiazol-3-yl]-2-ethyl-6-methyl-phenoxy}-propane-1,2-diol;
(S)-3-{4-[5-(2-diethylamino-6-methyl-pyridin-4-yl)-[1,2,4]oxadiazol-3-yl]-2-ethyl-6-methyl-phenoxy}-propane-1,2-diol;
(R)-3-(4-{5-[2-(ethyl-methyl-amino)-6-methyl-pyridin-4-yl]-[1,2,4]oxadiazol-3-yl}-2,6-dimethyl-phenoxy)-propane-1,2-diol;
(S)-3-(4-{5-[2-(ethyl-methyl-amino)-6-methyl-pyridin-4-yl]-[1,2,4]oxadiazol-3-yl}-2,6-dimethyl-phenoxy)-propane-1,2-diol;
(S)-3-(4-{5-[2-(isopropyl-methyl-amino)-6-methyl-pyridin-4-yl]-[1,2,4]oxadiazol-3-yl}-2,6-dimethyl-phenoxy)-propane-1,2-diol;
N—((S)-3-{4-[5-(2-diethylamino-6-methyl-pyridin-4-yl)-[1,2,4]oxadiazol-3-yl]-2-ethyl-6-methyl-phenoxy}-2-hydroxy-propyl)-2-hydroxy-acetamide;
N—((R)-3-{4-[5-(2-diethylamino-6-methyl-pyridin-4-yl)-[1,2,4]oxadiazol-3-yl]-2-ethyl-6-methyl-phenoxy}-2-hydroxy-propyl)-2-hydroxy-acetamide; and
(S)-3-(2-ethyl-4-{5-[2-(isopropyl-methyl-amino)-6-methyl-pyridin-4-yl]-[1,2,4]oxadiazol-3-yl}-6-methyl-phenoxy)-propane-1,2-diol.

Further examples of preferred compounds are selected from the group consisting of:
4-{5-[2-(isopropyl-methyl-amino)-6-methyl-pyridin-4-yl]-[1,2,4]oxadiazol-3-yl}-2,6-dimethyl-phenol;
3-[3-(2-ethyl-4-{5-[2-(isopropyl-methyl-amino)-6-methyl-pyridin-4-yl]-[1,2,4]oxadiazol-3-yl}-6-methyl-phenyl)-propionylamino]-propionic acid;
N—[(R)-3-(2-ethyl-4-{5-[2-(ethyl-methyl-amino)-6-methyl-pyridin-4-yl]-[1,2,4]oxadiazol-3-yl}-6-methyl-phenoxy)-2-hydroxy-propyl]-2-hydroxy-acetamide;
N—[(S)-3-(2-ethyl-4-{5-[2-(ethyl-methyl-amino)-6-methyl-pyridin-4-yl]-[1,2,4]oxadiazol-3-yl}-6-methyl-phenoxy)-2-hydroxy-propyl]-2-hydroxy-acetamide;
N—[(R)-3-(2-ethyl-4-{3-[2-(ethyl-methyl-amino)-6-methyl-pyridin-4-yl]-[1,2,4]oxadiazol-5-yl}-6-methyl-phenoxy)-2-hydroxy-propyl]-2-hydroxy-acetamide;
N—[(S)-3-(2-ethyl-4-{3-[2-(ethyl-methyl-amino)-6-methyl-pyridin-4-yl]-[1,2,4]oxadiazol-5-yl}-6-methyl-phenoxy)-2-hydroxy-propyl]-2-hydroxy-acetamide;
1-((S)-3-{4-[5-(2-diethylamino-6-methyl-pyridin-4-yl)-[1,2,4]oxadiazol-3-yl]-2-ethyl-6-methyl-phenoxy}-2-hydroxy-propyl)-azetidine-3-carboxylic acid;
1-(2-{4-[5-(2-diethylamino-6-methyl-pyridin-4-yl)-[1,2,4]oxadiazol-3-yl]-2-ethyl-6-methyl-phenoxy}-ethyl)-pyrrolidine-3-(S)-carboxylic acid;
1-(2-{4-[5-(2-diethylamino-6-methyl-pyridin-4-yl)-[1,2,4]oxadiazol-3-yl]-2-ethyl-6-methyl-phenoxy}-ethyl)-pyrrolidine-3-(R)-carboxylic acid;
(3-{4-[5-(2-diethylamino-6-methyl-pyridin-4-yl)-[1,2,4]oxadiazol-3-yl]-2-ethyl-6-methyl-phenyl}-propionylamino)-acetic acid;
3-(3-{4-[5-(2-diethylamino-6-methyl-pyridin-4-yl)-[1,2,4]oxadiazol-3-yl]-2-ethyl-6-methyl-phenyl}-propionylamino)-propionic acid;
(R)-3-{4-[3-(2-diethylamino-6-methyl-pyridin-4-yl)-[1,2,4]oxadiazol-5-yl]-2-ethyl-6-methyl-phenoxy}-propane-1,2-diol;
N—((R)-3-{4-[3-(2-diethylamino-6-methyl-pyridin-4-yl)-[1,2,4]oxadiazol-5-yl]-2-ethyl-6-methyl-phenoxy}-2-hydroxy-propyl)-2-hydroxy-acetamide;
N—((S)-3-{4-[3-(2-diethylamino-6-methyl-pyridin-4-yl)-[1,2,4]oxadiazol-5-yl]-2-ethyl-6-methyl-phenoxy}-2-hydroxy-propyl)-2-hydroxy-acetamide;
N—((S)-3-{4-[5-(2-diethylamino-6-methyl-pyridin-4-yl)-[1,3,4]oxadiazol-2-yl]-2-ethyl-6-methyl-phenoxy}-2-hydroxy-propyl)-2-hydroxy-acetamide;
N—((S)-3-{4-[5-(2-diethylamino-6-methyl-pyridin-4-yl)-[1,3,4]thiadiazol-2-yl]-2-ethyl-6-methyl-phenoxy}-2-hydroxy-propyl)-2-hydroxy-acetamide;
N—((S)-3-{4-[5-(2-diethylamino-6-methyl-pyridin-4-yl)-[1,2,4]oxadiazol-3-yl]-2-methyl-6-propyl-phenoxy}-2-hydroxy-propyl)-2-hydroxy-acetamide;
(R)-3-{2-chloro-4-[5-(2-diethylamino-6-methyl-pyridin-4-yl)-[1,2,4]oxadiazol-3-yl]-6-methyl-phenoxy}-propane-1,2-diol;
(S)-3-{2-chloro-4-[5-(2-diethylamino-6-methyl-pyridin-4-yl)-[1,2,4]oxadiazol-3-yl]-6-methyl-phenoxy}-propane-1,2-diol;
N—((R)-3-{2-chloro-4-[5-(2-diethylamino-6-methyl-pyridin-4-yl)-[1,2,4]oxadiazol-3-yl]-6-methyl-phenoxy}-2-hydroxy-propyl)-2-hydroxy-acetamide;

N—((S)-3-{2-chloro-4-[5-(2-diethylamino-6-methyl-pyridin-4-yl)-[1,2,4]oxadiazol-3-yl]-6-methyl-phenoxy}-2-hydroxy-propyl)-2-hydroxy-acetamide;

{4-[3-(4-amino-3-chloro-5-methyl-phenyl)-[1,2,4]oxadiazol-5-yl]-6-methyl-pyridin-2-yl}-diethyl-amine;

(R)-3-{2-chloro-4-[5-(2-diethylamino-6-methyl-pyridin-4-yl)-[1,2,4]oxadiazol-3-yl]-6-methoxy-phenoxy}-propane-1,2-diol;

(S)-3-{2-chloro-4-[5-(2-diethylamino-6-methyl-pyridin-4-yl)-[1,2,4]oxadiazol-3-yl]-6-methoxy-phenoxy}-propane-1,2-diol;

(S)-1-amino-3-{2-chloro-4-[5-(2-diethylamino-6-methyl-pyridin-4-yl)-[1,2,4]oxadiazol-3-yl]-6-methoxy-phenoxy}-propan-2-ol;

N—((R)-3-{2-chloro-4-[5-(2-diethylamino-6-methyl-pyridin-4-yl)-[1,2,4]oxadiazol-3-yl]-6-methoxy-phenoxy}-2-hydroxy-propyl)-2-hydroxy-acetamide;

N—((S)-3-{2-chloro-4-[5-(2-diethylamino-6-methyl-pyridin-4-yl)-[1,2,4]oxadiazol-3-yl]-6-methoxy-phenoxy}-2-hydroxy-propyl)-2-hydroxy-acetamide;

(S)-3-{2,6-dichloro-4-[5-(2-diethylamino-6-methyl-pyridin-4-yl)-[1,2,4]oxadiazol-3-yl]-phenoxy}-propane-1,2-diol;

(R)-3-{2,6-dichloro-4-[5-(2-diethylamino-6-methyl-pyridin-4-yl)-[1,2,4]oxadiazol-3-yl]-phenoxy}-propane-1,2-diol;

N—[(R)-3-(2-ethyl-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

N—[(S)-3-(2-ethyl-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

3-(2-ethyl-4-{5-[2-(isopropyl-methyl-amino)-6-methyl-pyridin-4-yl]-[1,2,4]oxadiazol-3-yl}-6-methyl-phenyl)-N-(2-hydroxy-ethyl)propionamide;

2-hydroxy-N—[(S)-2-hydroxy-3-(4-{5-[2-(isopropyl-methyl-amino)-6-methyl-pyridin-4-yl]-[1,2,4]oxadiazol-3-yl}-2-methyl-6-propyl-phenoxy)-propyl]-acetamide;

(R)-3-(2-chloro-4-{5-[2-(isopropyl-methyl-amino)-6-methyl-pyridin-4-yl]-[1,2,4]oxadiazol-3-yl}-6-methyl-phenoxy)-propane-1,2-diol;

(S)-3-(2-chloro-4-{5-[2-(isopropyl-methyl-amino)-6-methyl-pyridin-4-yl]-[1,2,4]oxadiazol-3-yl}-6-methyl-phenoxy)-propane-1,2-diol;

N—[(R)-3-(2-chloro-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

N—[(S)-3-(2-chloro-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

(R)-3-(2-chloro-4-{5-[2-(isopropyl-methyl-amino)-6-methyl-pyridin-4-yl]-[1,2,4]oxadiazol-3-yl}-6-methoxy-phenoxy)-propane-1,2-diol;

(S)-3-(2-chloro-4-{5-[2-(isopropyl-methyl-amino)-6-methyl-pyridin-4-yl]-[1,2,4]oxadiazol-3-yl}-6-methoxy-phenoxy)-propane-1,2-diol;

(R)-1-amino-3-(2-chloro-4-{5-[2-(isopropyl-methyl-amino)-6-methyl-pyridin-4-yl]-[1,2,4]oxadiazol-3-yl}-6-methoxy-phenoxy)-propan-2-ol;

(S)-1-amino-3-(2-chloro-4-{5-[2-(isopropyl-methyl-amino)-6-methyl-pyridin-4-yl]-[1,2,4]oxadiazol-3-yl}-6-methoxy-phenoxy)-propan-2-ol;

N—[(R)-3-(2-chloro-4-{5-[2-(isopropyl-methyl-amino)-6-methyl-pyridin-4-yl]-[1,2,4]oxadiazol-3-yl}-6-methoxy-phenoxy)-2-hydroxy-propyl]-2-hydroxy-acetamide;

N—[(S)-3-(2-chloro-4-{5-[2-(isopropyl-methyl-amino)-6-methyl-pyridin-4-yl]-[1,2,4]oxadiazol-3-yl}-6-methoxy-phenoxy)-2-hydroxy-propyl]-2-hydroxy-acetamide;

(R)-3-(4-{5-[2-(isopropyl-methyl-amino)-6-methyl-pyridin-4-yl]-[1,2,4]oxadiazol-3-yl}-3-methoxy-phenoxy)-propane-1,2-diol;

(S)-3-(4-{5-[2-(isopropyl-methyl-amino)-6-methyl-pyridin-4-yl]-[1,2,4]oxadiazol-3-yl}-3-methoxy-phenoxy)-propane-1,2-diol;

2-hydroxy-N—[(R)-2-hydroxy-3-(4-{5-[2-(isopropyl-methyl-amino)-6-methyl-pyridin-4-yl]-[1,2,4]oxadiazol-3-yl}-3-methoxy-phenoxy)-propyl]-acetamide;

2-hydroxy-N—[(S)-2-hydroxy-3-(4-{5-[2-(isopropyl-methyl-amino)-6-methyl-pyridin-4-yl]-[1,2,4]oxadiazol-3-yl}-3-methoxy-phenoxy)-propyl]-acetamide;

(R)-3-(2-ethyl-4-{3-[2-(isopropyl-methyl-amino)-6-methyl-pyridin-4-yl]-[1,2,4]oxadiazol-5-yl}-6-methyl-phenoxy)-propane-1,2-diol;

N—[(S)-3-(2-ethyl-4-{3-[2-(isopropyl-methyl-amino)-6-methyl-pyridin-4-yl]-[1,2,4]oxadiazol-5-yl}-6-methyl-phenoxy)-2-hydroxy-propyl]-2-hydroxy-acetamide;

N—[(S)-3-(2-ethyl-4-{5-[2-(isopropyl-methyl-amino)-6-methyl-pyridin-4-yl]-[1,3,4]oxadiazol-2-yl}-6-methyl-phenoxy)-2-hydroxy-propyl]-2-hydroxy-acetamide;

N—((R)-3-{2-ethyl-6-methyl-4-[5-(2-methyl-6-pyrrolidin-1-yl-pyridin-4-yl)-[1,2,4]oxadiazol-3-yl]-phenoxy}-2-hydroxy-propyl)-2-hydroxy-acetamide;

N—((S)-3-{2-ethyl-6-methyl-4-[5-(2-methyl-6-pyrrolidin-1-yl-pyridin-4-yl)-[1,2,4]oxadiazol-3-yl]-phenoxy}-2-hydroxy-propyl)-2-hydroxy-acetamide;

N—((S)-3-{4-[5-(2-dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide;

(S)-3-{4-[5-(2-diethylamino-6-ethyl-pyridin-4-yl)-[1,2,4]oxadiazol-3-yl]-2-ethyl-6-methyl-phenoxy}-propane-1,2-diol;

(R)-3-{2-ethyl-4-[5-(2-isopropylamino-6-methyl-pyridin-4-yl)-[1,2,4]oxadiazol-3-yl]-6-methyl-phenoxy}-propane-1,2-diol;

(S)-3-{2-ethyl-4-[5-(2-isopropylamino-6-methyl-pyridin-4-yl)-[1,2,4]oxadiazol-3-yl]-6-methyl-phenoxy}-propane-1,2-diol;

N—((R)-3-{2-ethyl-4-[5-(2-isopropylamino-6-methyl-pyridin-4-yl)-[1,2,4]oxadiazol-3-yl]-6-methyl-phenoxy}-2-hydroxy-propyl)-2-hydroxy-acetamide;

N—((S)-3-{2-ethyl-4-[5-(2-isopropylamino-6-methyl-pyridin-4-yl)-[1,2,4]oxadiazol-3-yl]-6-methyl-phenoxy}-2-hydroxy-propyl)-2-hydroxy-acetamide;

N—[(R)-3-(2-ethyl-4-{5-[2-ethyl-6-(ethyl-methyl-amino)-pyridin-4-yl]-[1,2,4]oxadiazol-3-yl}-6-methyl-phenoxy)-2-hydroxy-propyl]-2-hydroxy-acetamide;

N—[(S)-3-(2-ethyl-4-{5-[2-ethyl-6-(ethyl-methyl-amino)-pyridin-4-yl]-[1,2,4]oxadiazol-3-yl}-6-methyl-phenoxy)-2-hydroxy-propyl]-2-hydroxy-acetamide;

N—[(S)-3-(2-ethyl-4-{5-[2-(isobutyl-methyl-amino)-6-methyl-pyridin-4-yl]-[1,2,4]oxadiazol-3-yl}-6-methyl-phenoxy)-2-hydroxy-propyl]-2-hydroxy-acetamide;

(S)-3-(4-{5-[2-chloro-6-(isopropyl-methyl-amino)-pyridin-4-yl]-[1,2,4]oxadiazol-3-yl}-2,6-dimethyl-phenoxy)-propane-1,2-diol;

(R)-3-(4-{5-[2-chloro-6-(isopropyl-methyl-amino)-pyridin-4-yl]-[1,2,4]oxadiazol-3-yl}-2,6-dimethyl-phenoxy)-propane-1,2-diol;

(S)—N-[3-(4-{5-[2-chloro-6-(isopropyl-methyl-amino)-pyridin-4-yl]-[1,2,4]oxadiazol-3-yl}-2,6-dimethyl-phenoxy)-2-hydroxy-propyl]-2-hydroxy-acetamide; and (R)—N-[3-(4-{5-[2-chloro-6-(isopropyl-methyl-amino)-pyridin-4-yl]-[1,2,4]oxadiazol-3-yl}-2,6-dimethyl-phenoxy)-2-hydroxy-propyl]-2-hydroxy-acetamide.

The compounds of formula (I) and their pharmaceutically acceptable salts can be used as medicaments, e.g. in the form of pharmaceutical compositions for enteral or parenteral administration and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of formula (I) are useful for the prevention and/or treatment of diseases or disorders associated with an activated immune system.

Such diseases or disorders include rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of formula (I) are selected from multiple sclerosis and psoriasis.

The present invention also relates to a method for the prevention or treatment of a disease or disorder mentioned herein comprising administering to a subject a pharmaceutically active amount of a compound of formula (I).

Furthermore, compounds of the formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of formula (I) for the preparation of a pharmaceutical composition, optionally for use in combination with one or several immunomodulating agents, for the prevention or treatment of the diseases and disorders mentioned herein.

The compounds of formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the formula (I) of the present invention can be prepared according to the general sequence of reactions outlined below. Only a few of the synthetic possibilities leading to compounds of formula (I) are described.

Structure 1

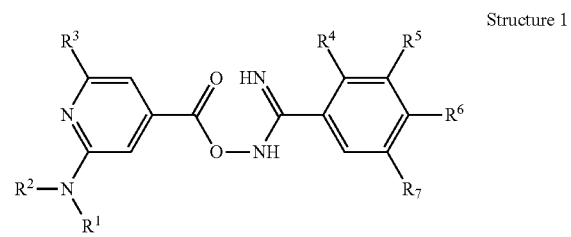

Compounds of formula (I) which represent a 5-pyridin-4-yl-[1,2,4]oxadiazole derivative, are prepared by reacting a compound of Structure 1 in a solvent such as dioxane, THF, dimethoxyethane, xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, methoxycarbonylsulfamoyl triethylammonium hydroxide (Burgess reagent), etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

Structure 2

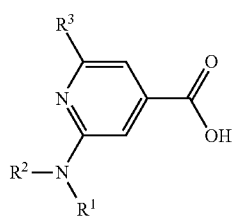

Structure 3

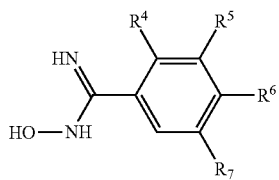

Compounds of Structure 1 may be prepared by reacting a compound of Structure 2 with a compound of Structure 3 in a solvent such as DMF, THF, DCM, etc. in the presence or absence of one or more coupling agents such as TBTU, DCC, EDC, HBTU, HOBt, CDI, PyBOP, etc. and in the presence or absence of a base such as triethylamine, DIPEA, NaH, $K_2CO_3$, etc. (Lit.: e.g. A. Hamze, J.-F. Hernandez, P. Fulcrand, J. Martinez, *J. Org. Chem.* 68 (2003) 7316-7321; and the literature cited above).

Structure 4

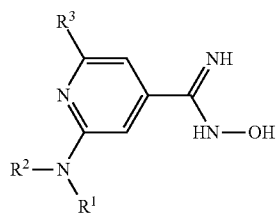

Structure 5

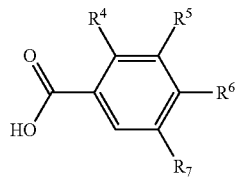

Compounds of formula (I) which represent a 3-pyridin-4-yl-[1,2,4]oxadiazole derivative are prepared in an analogous fashion (Lit.: e.g. C. T. Brain, J. M. Paul, Y. Loong, P. J. Oakley, *Tetrahedron Lett.* 40 (1999) 3275-3278) by reacting a compound of Structure 4 with a compound of Structure 5 and subsequent cyclisation of the corresponding hydroxyamidine ester intermediate. Compounds of Structure 5 are either commercially available or are prepared according to procedures described herein or according to procedures known to a person skilled in the art.

Structure 6

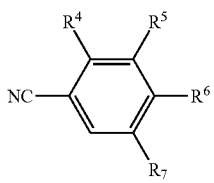

Structure 7

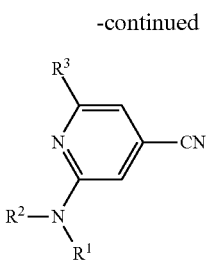

Compounds of Structure 3 and 4 may be prepared by reacting a compound of Structure 6 and 7, respectively, with hydroxylamine or one of its salts in a solvent such as methanol, ethanol, pyridine, etc. in the presence or absence of a base such as $Na_2CO_3$, $K_2CO_3$, triethylamine, KOtBu, etc. (Lit.: e.g. T. Suzuki, K. Iwaoka, N. Imanishi, Y. Nagakura, K. Miyta, H. Nakahara, M. Ohta, T. Mase, Chem. Pharm. Bull. 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, Bioorg. Med. Chem. 11 (2003), 3379-3392; R. Miller, F. Lang, Z. J. Song, D. Zewge, WO 2004/035538 (Merck & Co., Inc., USA); B. Kaboudin, K. Navaee, Heterocycles 60 (2003), 2287-2292).

Methods that effect the transformation of a compound of Structure 2 into a compound of Structure 7, or the opposite, are known to a person skilled in the art.

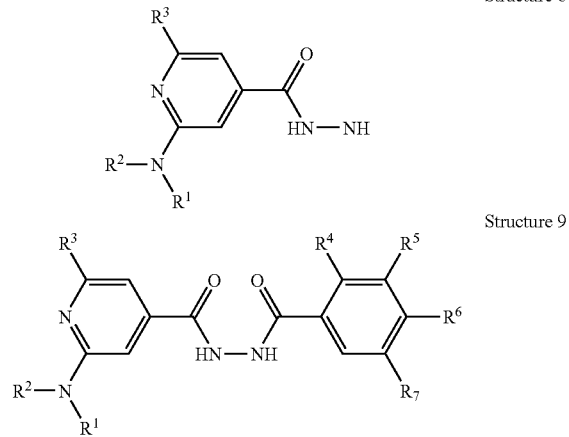

Compounds of formula (I) which represent a 2-pyridin-4-yl-[1,3,4]oxadiazole or a 2-pyridin-4-yl-[1,3,4]thiadiazole derivative are prepared similarly by reacting a compound of Structure 2 with hydrazine (by using a coupling reagent such as TBTU, DCC, EDC, HBTU, PyBOP, HOBt, CDI, etc.) to form a compound of Structure 8 which is then coupled with a compound of Structure 5 to give a compound of Structure 9. A compound of Structure 9 can also be prepared by following the reverse reaction order i.e. by first coupling a compound of Structure 5 with hydrazine followed by reacting the corresponding hydrazide intermediate with a compound of Structure 2. Dehydration of a compound of Structure 9 to form the desired 2-pyridin-4-yl-[1,3,4]oxadiazole derivative is affected by treating a compound of Structure 9 with a reagent such as $POCl_3$, $CCl_4$ or $CBr_4$ in combination with triphenylphosphine, $P_2O_5$, Burgess reagent, etc. in a solvent such as toluene, acetonitrile, dioxane, THF, $CHCl_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, J. Med. Chem. 48 (2005) 4068-4075; C. T. Brain, J. M. Paul, Y. Loong, P. J. Oakley, Tetrahedron Lett. 40 (1999) 3275-3278). Likewise, 2-pyridin-4-yl-[1,3,4]thiadiazole derivatives are obtained by cyclising a compound of Structure 9 with Lawesson's reagent, optionally in combination with $P_2S_5$, in the presence or absence of a solvent such as pyridine, toluene, THF, acetonitrile, etc. at elevated temperatures with or without microwave irradiation (Lit.: e.g. A. A. Kiryanov, P. Sampson, A. J. Seed, J. Org. Chem. 66 (2001) 7925-7929).

Depending on the nature of the functionalities present in the residues $R^4$ to $R^7$ in Structures 1, 3, 5, and 6, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3rd Edition, Wiley N.Y., 1999; P. J. Kocienski, Protecting Groups, Thieme Stuttgart, 1994). Alternatively, the desired residues $R^4$ to $R^7$, in particular $R^6$, may also be introduced in later steps that follow the A-ring formation between the pyridine and the phenyl rings according to procedures described herein or according to procedures known to a person skilled in the art. The phenyl compounds of Structure 3, 5, and 6 or their precursors are either commercially available or are prepared according to procedures known to a person skilled in the art.

Structure 10

Compounds of formula (I) which represent a 5-pyridin-4-yl-oxazole or a 5-pyridin-4-yl-thiazole derivative are prepared by treating a compound of Structure 10 either with $POCl_3$, $PCl_5$, $I_2$ in combination with triphenylphosphine and triethylamine, trifluoracetic anhydride, Burgess reagent, etc. in a solvent such as toluene, benzene, dioxane, THF, etc. at temperatures between 20 and 120° C., or with Lawesson's reagent, optionally in combination with $P_2S_5$, in the presence or absence of a solvent such as pyridine, toluene, THF, acetonitrile, etc. at elevated temperatures with or without microwave irradiation as mentioned above (Lit.: e.g. N. Sato, T. Shibata, M. Jitsuoka, T. Ohno, T. Takahashi, T. Hirohashi, T. Kanno, H. Iwaasa, A. Kanatani, T. Fukami, Takehiro, Bioorg. & Med. Chem. Lett. 14 (2004) 1761-1764). The compounds of Structure 10 are prepared by reacting a compound of Structure 11 with a compound of Structure 5. The aminoketon of Structure 11 can be prepared from a compound of Structure 2 by procedures given in the literature (e.g. J. L. LaMattina, J. Heterocyclic Chem. 20 (1983) 533-538; M. Pesson, M. Antoine, P. Girard, J. L. Benichon, S. Chabassier, P. De Lajudie, S. Patte, F. Roquet, G. Montay, Eur. J. Med. Chem. 15 (1980) 263-268). Compounds of formula (I) which represent a 2-pyridin-4-yl-oxazole or a 2-pyridin-4-yl-thiazole derivative are prepared in an analogous fashion from a compound of Structure 12 and a compound of Structure 2. The compounds of Structure 12 are prepared in analogy to literature procedures (e.g. W. A. Loughlin, L. C. Henderson, K. E. Elson, M. E. Murphy, *Synthesis* 2006, 1975-1980; L. Widler, J. Green, M. Missbach, M. Susa, E. Altmann, *Bioorganic & Medicinal Chemistry Letters* 11 (2001) 849-852; J. M. Holub et al., *Molecules* 9 (2004) 135-157).

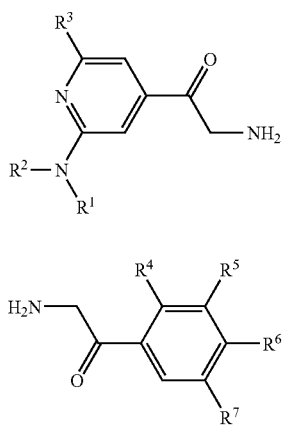

Structure 11

Structure 12

Alternatively, the bonds between the pyridine or the phenyl ring and the central 5-membered heteroaromatic ring can also be formed by applying palladium catalysed cross coupling reactions.

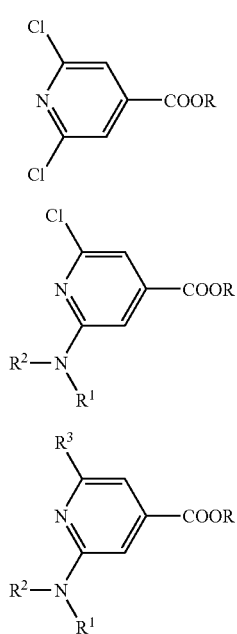

Structure 13

Structure 14

Structure 15

Compounds of Structure 2 may be prepared by reacting a 2,6-dichloro-isonicotinic acid ester (Structure 13, wherein R represents a $C_{1-4}$-alkyl, preferably an isopropyl or an tert.-butyl group; the compounds of Structure 13 are either commercially available or can be prepared as described herein or by standard procedures) with the appropriate amine $NHR^1R^2$ in the presence or absence of an additional solvent such as THF, dioxane, ethanol, etc., preferably at temperatures above 50° C. to give a compound of Structure 14. The compounds of Structure 14 can then be reacted with the appropriate alkyl-Zn reagent (e.g. $Me_2Zn$, $MeZnCl$, $Et_2Zn$, etc.) under Negishi reaction conditions (Lit.: e.g. H. Matsushita, E. Negishi, *J. Org. Chem.* 47 (1982) 4161-4165) to give a compound of Structure 15, which can be hydrolysed to a compound of Structure 2. In addition, compounds of the Structure 15 may be prepared by reacting a compound of Structure 14 with an alkyl Grignard reagent in the presence of $Fe(acac)_3$ in a solvent such as THF, dioxane, DMF, NMP, etc., or combinations thereof, at temperatures ranging from −78 to 25° C. (Fürstner conditions, Lit.: e.g. A. Fürstner, A. Leitner, M. Mendez, H. Krause, *J. Am. Chem. Soc.* 124 (2002) 13856-13863; A. Fürstner, A. Leitner, *Angew. Chem.* 114 (2002) 632-635). In case $R^3$ represents a $C_{2-4}$-alkyl group, the corresponding compounds of Structure 15 can also be prepared by reacting a compound of Structure 14 with an alkenyl boron derivative (e.g. 2,4,6-trivinyl-cyclotriboroxane) under Suzuki conditions (Lit.: e.g. F. Kerins, D. F. O'Shea, *J. Org. Chem.* 67 (2002) 4968-4971). The obtained 2-amino-6-alkenyl-isonicotinic acid derivative is hydrogenated to the corresponding compound of Structure 15.

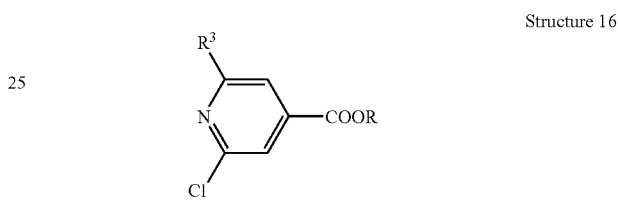

Structure 16

Alternatively, the compounds of Structure 15 may also be prepared by reacting a compound of Structure 16 with the appropriate amine $NHR^1R^2$ under Buchwald-Hartwig conditions (Lit.: J. P. Wolfe, H. Tomori, J. P. Sadighi, J. Yin, S. L. Buchwald, *J. Org. Chem.* 65 (2000) 1158-1174; S. Wagaw, S. L. Buchwald, *J. Org. Chem.* 61 (1996) 7240-7241; M. C. Harris, O. Geis, S. L. Buchwald, *J. Org. Chem.* 64 (1999) 6019-6022; S. R. Stauffer, S. Lee, J. P. Stambuli, S. I. Hauck, J. F. Hartwig, *Org. Letters* 2 (2000) 1423-1426). Compounds of Structure 16 or their corresponding acids are either commercially available or may be prepared by reacting a 2,6-dichloro-isonicotinic acid ester (Structure 13) with an alkyl Grignard reagent under Fürstner conditions (see above) or with an alkyl-Zn reagent under Negishi conditions. Reacting a compound of Structure 13 with an alkenyl boron derivative under Suzuki conditions, treating the corresponding alkenyl-chloro-isonicotinic acid ester with an amine $NHR^1R^2$ under Buchwald-Hartwig conditions and subsequent hydrogenation may also give access to compounds of Structure 15. The residues $R^1$ and $R^2$ may also be introduced by sequencial alkylation and/or reductive amination of a compound of Structure 17 (Lit.: e.g. N. Finch, T. R. Campbell, C. W. Gemenden, H. J. Povalski, *J. Med. Chem.* 23 (1980) 1405-1410) which may be prepared by reacting a compound of Structure 16 with ammonia in a solvent such as water, methanol, ethanol, THF, etc. at elevated temperatures.

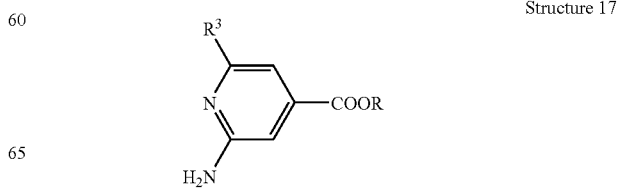

Structure 17

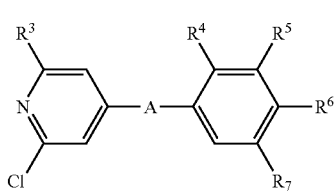
Structure 18

In case $R^1$ represents hydrogen, the corresponding monoalkylamino-pyridine derivatives that may occur in the course of the synthesis of compounds of formula (I), may require temporary protection at the secondary amine function.

The above described reaction sequences that allow the introduction of the two residues $R^3$ and —$NR^1R^2$ may also be applied to a compound in which the scaffold has already been further elaborated. For instance, the Buchwald reaction may also be applied to a compound of Structure 18 which can be obtained from the appropriate 2-chloro-isonicotinic acid derivative according to the methods described above.

EXAMPLES

The following examples illustrate the invention but do not at all limit the scope thereof.

All temperatures are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% acetonitrile in water, 1 min, with 0.04% trifluoroacetic acid, flow: 4.5 mL/min), $t_R$ is given in min; retention times or LC-MS marked with * refer to an LC run under basic conditions, i.e. eluting with a gradient of MeCN in water containing 13 mM of ammonium hydroxide, otherwise identical conditions; by TLC (TLC-plates from Merck, Silica gel 60 $F_{254}$); or by melting point. Compounds are purified by preparative HPLC (column: X-terra RP18, 50×19 mm, 5 µm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol). Racemates can be separated into their enantiomers by preparative HPLC (column: ChiralPaK AD 20×250 mm, 5 µm, 15% ethanol in hexane).

Abbreviations (as Used Herein):
aq. aqueous
atm atmosphere
BSA bovine serum albumin
BOC tert-butoxycarbonyl
Bu butyl
CC column chromatography
CDI carbonyl diimidazole
dba dibenzylidene acetone
DCC dicyclohexyl carbodiimide
DCM dichloromethane
DEAD diethyl azodicarboxylate
DIPEA diisopropyl-ethylamine, Hünig's base, ethyl-diisopropylamine
DMF dimethylformamide
DMSO dimethylsulfoxide
dppf 1,1'-bis(diphenylphosphino-KP)ferrocene
DPPP 1,3-bis-(diphenylphosphino)-propane
EA ethyl acetate
EDC N-(3-dimethylaminopropyl)-N'-ethyl-carbodiimide
Et ethyl
FC flash chromatography
Fe(acac)$_3$ iron (III) acetylacetone-complex
h hour(s)
HBTU O-(benzotriazol-1-yl)-N,N,N',N'-tetramethyluronium hexafluorophosphate
HOBt 1-hydroxybenzotriazole
HPLC high performance liquid chromatography
HV high vacuum conditions
KOtBu potassium tert-butoxide
LC-MS liquid chromatography mass spectrometry
Lit. literature
Me methyl
min minute(s)
MPLC medium pressure liquid chromatography
NaOAc sodium acetate
NMP N-methylpyrrolidin-2-one
OAc acetate
org. organic
Ph phenyl
PyBOP benzotriazol-1-yl-oxy-tris-pyrrolidino-phosphonium-hexafluoro-phosphate
prep. preparative
rt room temperature
sat. saturated
S1P sphingosine 1-phosphate
TBME tert butyl methyl ether
TBTU 2-(1H-benzotriazole-1-yl)-1,2,3,3-tetramethyluronium tetrafluoroborate
TFA trifluoroacetic acid
THF tetrahydrofuran
TLC thin layer chromatography
$t_R$ retention time
Xantphos 4,5-bis(diphenylphosphino)-9,9-dimethylxanthene 2-Dimethylamino-6-methyl-isonicotinic acid a) 2-Chloro-6-methyl-isonicotinic acid (7.55 g, 44.0 mmol) is suspended in toluene (150 mL) at 80° C. and then treated with N,N-dimethylformamide di-tert.-butyl acetal (50 mL, 209 mmol). The mixture is stirred at 80° C. for 3 h, then at rt for 72 h. The clear solution is diluted with diethyl ether (250 mL), washed with sat. aq. NaHCO$_3$ solution (4×50 mL), dried over MgSO$_4$, filtered and concentrated. The crude product is purified by MPLC on silica gel eluting with heptane:ethyl acetate to give 2-chloro-6-methyl-isonicotinic acid tert.-butyl ester (8.57 g) as a brownish oil which slowly solidifies; LC-MS: $t_R$=0.99 min, [M+H]$^+$=213.24 (−15); $^1$H NMR (D$_6$-DMSO): δ 1.56 (s, 9H), 2.54 (s, 3H), 7.59 (s, 1H), 7.66 (s, 1H).

b) Under argon, a solution of 2-chloro-6-methyl-isonicotinic acid tert.-butyl ester (625 mg 2.75 mmol), Na tert.-butylate (396 mg, 4.10 mmol), Xantphos (173 mg, 0.30 mmol) and Pd(OAc)$_2$ (83 mg, 0.37 mmol) in 2 M dimethylamine in THF (35 mL) is stirred at 110° C. for 18 h. The dark reaction mixture is cooled to rt, diluted with 6 N aq. HCl and extracted with diethyl ether (4×60 mL). The org. extracts are concentrated, the residue is dissolved in 6N aq. HCl and heated to 100° C. for 18 h. The orange suspension is concentrated, dissolved in 1 N aq. NaOH (40 mL) and concentrated again. The residue is dissolved in 1 N aq. NaOH (3 mL) and methanol and separated by MPLC on RP-C$_{18}$ silica gel to give 2-dimethylamino-6-methyl-isonicotinic acid (1.1 g) as a beige oil; LC-MS: $t_R$=0.44 min, [M+H]$^+$=181.07.

2-(Ethyl-methyl-amino)-6-methyl-isonicotinic acid

The title compound is obtained as yellow crystals (420 mg) in analogy to 2-dimethylamino-6-methyl-isonicotinic acid starting from 2-chloro-6-methyl-isonicotinic acid tert.-butyl ester (730 mg, 3.21 mmol) and ethyl-methylamine; LC-MS: $t_R$=0.50 min, [M+H]$^+$=195.05; $^1$H NMR (D$_6$-DMSO): δ 1.08 (t, J=6.8 Hz, 3H), 2.38 (s, 3H), 3.03 (s, 3H), 3.60 (q, J=6.8 Hz, 2H), 6.85 (s, 2H).

2-Diethylamino-6-methyl-isonicotinic acid a) A solution of 2,6-dichloroisonicotinic acid (20.0 g, 104 mmol) in ethanol (250 mL) and H$_2$SO$_4$ (5 mL) is stirred at 80° C. for 28 h. The solvent is removed in vacuo and the residue is dissolved in EA, washed with sat. aq. NaHCO$_3$ solution and water, dried over MgSO$_4$, filtered and evaporated to give 2,6-dichloroisonicotinic acid ethyl ester (17.7 g) as a brownish solid; LC-MS: $t_R$=1.31 min.

b) A solution of 2,6-dichloroisonicotinic acid ethyl ester (14.0 g, 63.6 mmol) in diethylamine (25 mL) is stirred at 100° C. for 7 h. The volatile compounds are evaporated and the residue is purified by CC on silica gel eluting with heptane:EA 9:1 to give 2-chloro-6-diethylamino-isonicotinic acid ethyl ester (10.1 g, contains 2-chloro-6-diethylamino-isonicotinic acid methyl ester which forms during the transfer of the reaction mixture into a round bottom flask using methanol); LC-MS: $t_R$=1.09 min.

c) To a solution of 2-chloro-6-diethylamino-isonicotinic acid ethyl ester (10.1 g, 31.6 mmol) in dioxane (120 mL), Pd(dppf) (262 mg, 0.322 mmol) is added. MeZnCl (8.40 g, 72.4 mmol) is added dropwise to the mixture before it is stirred at 75° C. for 18 h. The mixture is carefully diluted with water, then extracted with EA. The combined org. extracts are dried over MgSO$_4$, filtered and concentrated. The crude product is purified by CC on silica gel eluting with heptane:EA 9:1 to give 2-diethylamino-6-methyl-isonicotinic acid ethyl ester (6.39 g, containing some methyl ester) as a pale yellow oil; LC-MS: $t_R$=0.70 min, [M+H]$^+$=237.11.

d) A solution of 2-diethylamino-6-methyl-isonicotinic acid ethyl ester (6.39 g, 27.0 mmol) in 6 N aq. HCl (100 mL) is stirred at 80° C. for 72 h before the solvent is removed in vacuo. The remaining solid is dried under high vacuum to give 2-diethylamino-6-methyl-isonicotinic acid hydrochloride (6.96 g) as a yellow solid; LC-MS: $t_R$=0.53 min, [M+H]$^+$=209.09; $^1$H NMR (D$_6$-DMSO): δ 1.17 (t, J=6.8 Hz, 6H), 2.51 (s, 3H), 3.68 (q, J=6.3 Hz, 4H), 6.96 (s, 1H), 7.15 (s br, 1H).

2-(Isopropyl-methyl-amino)-6-methyl-isonicotinic acid

The title compound is prepared in analogy to 2-diethylamino-6-methyl-isonicotinic acid hydrochloride using isopropylmethylamine; LC-MS: $t_R$=0.54 min, [M+H]$^+$=209.09; $^1$H NMR δ 1.37 (d, J=6.3 Hz, 6H), 2.64 (s, 3H), 3.17 (s, 3H), 4.50-4.60 (m, 1H), 7.16 (s, 1H), 7.62 (s, 1H).

2-Methyl-6-pyrrolidin-1-yl-isonicotinic acid

A solution of 2-chloro-6-methyl-isonicotinic acid (1.03 g, 5.98 mmol) in pyrrolidine (5 mL) is stirred at 85° C. for 6 days. The mixture is diluted with 1 N aq. NaOH (40 mL) and the solvent is removed in vacuo. The crude product is again dissolved in 1 N aq. NaOH (3 mL) and methanol (1 mL) and purified by MPLC on RP-C$_{18}$-silica gel to give 2-methyl-6-pyrrolidin-1-yl-isonicotinic acid (1.18 g) as a beige solid; LC-MS: $t_R$=0.52 min, [M+H]$^+$=207.06; $^1$H NMR (D$_6$-DMSO): δ 1.89-1.94 (m, 4H), 2.27 (s, 3H), 3.33-3.38 (m, 4H), 6.61 (s, 1H), 6.77 (s, 1H).

2-(Isobutyl-methyl-amino)-6-methyl-isonicotinic acid

The title compound is prepared in analogy to 2-dimethylamino-6-methyl-isonicotinic acid starting from 2-chloro-6-methyl-isonicotinic acid and using isobutyl-methyl-amine; LC-MS: $t_R$=0.61 min, [M+H]$^+$=223.10.

2-Dimethylamino-6-ethyl-isonicotinic acid a) 2,6-Dichloro-isonicotinic acid (11.2 g, 57.1 mmol) is suspended in toluene (150 mL) at 80° C. and then treated with N,N-dimethylformamide di-tert.-butyl acetal (50 mL, 209 mmol). The dark mixture is stirred at 80° C. for 12 h, then at rt for 16 h. The dark solution is diluted with diethyl ether (400 mL), washed with sat. aq. NaHCO$_3$ solution (3×100 mL), dried over Na$_2$SO$_4$, filtered and concentrated. The crude product is purified by MPLC on silica gel eluting with heptane:ethyl acetate to give 2,6-dichloro-isonicotinic acid tert.-butyl ester (14.2 g) as a brownish oil which slowly solidifies; LC-MS: $t_R$=1.05 min; $^1$H NMR (D$_6$-DMSO): δ 1.56 (s, 9H), 7.85 (s, 2H).

b) A red to brown solution of 2,6-dichloro-isonicotinic acid tert.-butyl ester (1.49 g, 6.0 mmol) in 2 M dimethylamine in THF (20 mL) is stirred at 65° C. for 2 h, then at 80° C. for 2 h and finally at 110° C. for 12 h in an autoclave. The mixture is concentrated to give crude 2-chloro-6-dimethylamino-isonicotinic acid tert-butyl ester (2.0 g) as a brown residue; LC-MS: $t_R$=1.08 min, [M+H]$^+$=257.32; $^1$H NMR (D$_6$-DMSO): δ 1.54 (s, 9H), 3.06 (s, 6H), 6.85 (s, 1H), 6.92 (s, 1H).

c) To a solution of 2-chloro-6-dimethylamino-isonicotinic acid tert-butyl ester (770 mg, 3.00 mmol) in dioxane (45 mL), Cs$_2$CO$_3$ (1270 mg, 3.90 mmol) followed by P(tert.-Bu)$_3$ (30 mg, 0.15 mmol) and 2,4,6-trivinylcyclotriboroxane pyridine complex (722 mg, 3.00 mmol, prepared according to F. Kerins, D. F. O'Shea *J. Org. Chem.* 67 (2002) 4968-4971) is added. The mixture is degassed an put under argon before Pd$_2$(dba)$_3$ (82 mg, 0.09 mmol) is added. The mixture is stirred at 100° C. for 15 h before it is cooled to rt and, filtered over a short silica gel pad eluting with DCM. The filtrate is concentrated and purified on prep. TLC plates with DCM to give 2-dimethylamino-6-vinyl-isonicotinic acid tert-butyl ester (885 mg) as a red to brownish resin; LC-MS: $t_R$=0.82 min, [M+1]$^+$=249.37.

d) To a solution of 2-dimethylamino-6-vinyl-isonicotinic acid tert-butyl ester (877 mg), 3.53 mmol) in methanol (15 mL), Pd/C (150 mg, 10% Pd) is added and the mixture is stirred under 2 atm of H$_2$ at rt for 3 h. The catalyst is filtered off and the filtrate is evaporated to give crude 2-dimethylamino-6-ethyl-isonicotinic acid tert-butyl ester; LC-MS: $t_R$=0.76 min, [M+1]$^+$=251.10. This material is dissolved in 6 N aq. HCl (60 mL) and the mixture is stirred at 80° C. for 72 h before the solvent is evaporated. The crude product is purified by MPLC on RP-C$_{18}$-silica gel to give 2-dimethylamino-6-ethyl-isonicotinic acid (332 mg) as an orange oil, LC-MS: $t_R$=0.51 min, [M+1]$^+$=195.10.

2-Diethylamino-6-ethyl-isonicotinic acid

The title compound is prepared in analogy to 2-dimethylamino-6-ethyl-isonicotinic acid using diethylamine; LC-MS: $t_R$=0.55 min, $[M+1]^+$=223.37.

2-Ethyl-6-(isopropyl-methyl-amino)-isonicotinic acid

The title compound is prepared in analogy to 2-dimethylamino-6-ethyl-isonicotinic acid using isopropylmethylamine; LC-MS: $t_R$=0.54 min, $[M+1]^+$=223.37.

2-Dimethylamino-6-isobutyl-isonicotinic acid

The title compound is prepared in analogy to 2-dimethylamino-6-ethyl-isonicotinic acid using 2,4,6-tris-(2-methylpropenyl)-cyclotriboroxane pyridine complex in the Suzuki coupling reaction; LC-MS: $t_R$=0.54 min, $[M+1]^+$=223.37.

2-Isopropylamino-6-methyl-isonicotinic acid

The title compound is prepared in analogy to 2-dimethylamino-6-methyl-isonicotinic acid starting from 2-chloro-6-methyl-isonicotinic acid and isopropylamine; LC-MS: $t_R$=0.52 min, $[M+1]^+$=195.09.

2-Methyl-6-morpholin-4-yl-isonicotinic acid

The title compound is prepared in analogy to 2-diethylamino-6-methyl-isonicotinic acid starting from 2,6-dichloro-isonicotinic acid and morpholine; LC-MS: $t_R$=0.47 min, $[M+1]^+$=223.08.

2-Ethyl-6-(ethyl-methyl-amino)-isonicotinic acid

The title compound is prepared in analogy to 2-diethylamino-6-methyl-isonicotinic acid starting from 2,6-dichloro-isonicotinic acid and N-ethyl-N-methylamine; LC-MS: $t_R$=0.56 min, $[M+1]^+$=209.09; $^1$H NMR (D$_6$-DMSO): δ 1.16 (t, J=7.0 Hz, 3H), 1.24 (t, J=7.3 Hz, 3H), 2.95 (q, J=7.5 Hz, 2H), 3.57 (s, 3H), 3.76 (q, J=6.8 Hz, 2H), 6.98 (s, 1H), 7.23 (s, 1H).

2-(Isobutyl-methyl-amino)-6-methyl-isonicotinic acid

The title compound is prepared in analogy to 2-diethylamino-6-methyl-isonicotinic acid starting from 2,6-dichloro-isonicotinic acid and N-isobutyl-N-methylamine; LC-MS: $t_R$=0.50*min, $[M+1]^+$=223.28.

2-Chloro-6-(isopropyl-methyl-amino)-isonicotinic acid

A mixture of 2,6-dichloro-isonicotinic acid (572 mg, 2.98 mmol) in isopropyl-methylamine (2.18 g, 29.8 mmol) is stirred at 80° C. for 10 days. The mixture is cooled to rt, diluted with water (50 mL), and extracted with diethyl ether (6×50 mL). The aq. phase is acidified and extracted with diethyl ether (3×50 mL). The org. extracts are combined, dried over MgSO$_4$, filtered and concentrated. The crude product is purified by MPLC on silica gel eluting with a gradient of EA in heptane to give the title compound (461 mg) as a yellow powder; LC-MS: $t_R$=0.92 min, $[M+1]^+$=229.01; $^1$H NMR (CD$_3$OD): δ 1.19 (d, J=6.7 Hz, 6H), 2.88 (s, 3H), 4.78-4.87 (m, 1H), 6.94 (s, 1H), 7.01 (s, 1H).

2-(Ethyl-methyl-amino)-N-hydroxy-6-methyl-isonicotinamidine a) To a solution of 2-(ethyl-methyl-amino)-6-methyl-isonicotinic acid (2.03 g, 8.80 mmol) and DIPEA (3.41 g, 26.4 mmol) in DMF (80 mL) is added PyBOP (5.00 g, 9.61 mmol) at 0° C. The mixture is stirred for 15 min before 0.5 M NH$_3$ in dioxane (52 mL) is added. Stirring is continued at rt for 2 h before the mixture is again cooled to 0° C. Pyridine (4.35 g, 44.8 mmol) followed by trifluoroacetic anhydride (9.29 g, 44.2 mmol) is carefully added and the reaction mixture is stirred for 2 h while warming to rt. The mixture is then stirred at 70° C. for 15 h, cooled to rt, diluted with DCM and washed with 10% aq. citric acid solution followed by sat. aq. Na$_2$CO$_3$-solution. The org. extract is dried over MgSO$_4$, filtered and concentrated. The crude product is purified by CC on silica gel eluting with heptane:EA 4:1 to give 2-(ethyl-methyl-amino)-6-methyl-isonicotinonitrile (257 mg) as a pale yellow oil; LC-MS: $t_R$=0.58 min, $[M+1]^+$=176.09.

b) To a solution of K tert butylate (574 mg, 5.11 mL) in methanol (10 mL), hydroxylamine hydrochloride (304 mg, 4.38 mmol) is added. To the stirred suspension, a solution of 2-(ethyl-methyl-amino)-6-methyl-isonicotinonitrile (256 mg, 1.46 mmol) in methanol (10 mL) is added and the resulting mixture is stirred at 60° C. for 15 h. The mixture is filtered, and the filtrate is concentrated. The residue is treated with 1 N aq. HCl, washed with DCM and then basified by adding 1 N aq. NaOH. The mixture is extracted three times with EA. The combined EA extracts are dried over MgSO$_4$, filtered, concentrated and dried to give the title compound as a pale yellow oil; LC-MS: $t_R$=0.45 min, $[M+1]^+$=209.10; $^1$H NMR (D$_6$-DMSO): δ 1.06 (t, J=6.5 Hz, 3H), 2.29 (s, 3H), 2.98 (s, 3H), 3.56 (q, J=6.3 Hz, 2H), 5.82 (s, 2H), 6.64 (s, 1H), 6.69 (s, 1H), 9.74 (s, 1H).

2-(Diethylamino)-N-hydroxy-6-methyl-isonicotinamidine

The title compound is prepared in analogy to 2-(ethyl-methyl-amino)-N-hydroxy-6-methyl-isonicotinamidine from 2-(diethylamino)-6-methyl-isonicotinic acid; LC-MS: $t_R$=0.50 min, $[M+1]^+$=223.12.

N-Hydroxy-2-(isopropyl-methyl-amino)-6-methyl-isonicotinamidine

The title compound is prepared in analogy to 2-(ethyl-methyl-amino)-N-hydroxy-6-methyl-isonicotinamidine from 2-(isopropyl-methyl-amino)-6-methyl-isonicotinic acid; LC-MS: $t_R$=0.50 min, $[M+1]^+$=223.13.

4,N-Dihydroxy-3,5-dimethyl-benzamidine

The title compound is prepared from commercially available 4-hydroxy-3,5-dimethyl-benzonitrile according to literature procedures (e.g. E. Meyer, A. C. Joussef, H. Gallardo, *Synthesis* 2003, 899-905); $^1$H NMR (CD$_3$OD): δ 7.20 (s, 2H), 2.20 (s, 6H).

4-Allyloxy-N-hydroxy-3,5-dimethyl-benzamidine

The title compound is prepared by allylating commercially available 4-hydroxy-3,5-dimethyl-benzonitrile with allylbromide in the presence of NaOH in isopropanol at rt. The nitrile is then transformed to the hydroxyamidine according to literature procedures (e.g. E. Meyer, A. C. Joussef, H. Gallardo, *Synthesis* 2003, 899-905); ¹H NMR (CD₃OD): δ 7.27 (s, 2H), 6.10 (m, 1H), 5.42 (m, 1H), 5.26 (m, 1H), 4.31 (dt, J=5.6, 1.5 Hz, 2H), 2.29 (s, 6H).

3-Ethyl-4,N-dihydroxy-5-methyl-benzamidine

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; ¹H NMR (D₆-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

4-Allyloxy-3-ethyl-N-hydroxy-5-methyl-benzamidine

The title compound is prepared by allylating 3-ethyl-4-hydroxy-5-methyl-benzaldehyde which is prepared from 2-ethyl-6-methyl-phenol following literature procedures (see 3-ethyl-4,N-dihydroxy-5-methyl-benzamidine). The aldehyde is then transformed into the corresponding hydroxyamidine according to literature procedures (see 3-ethyl-4,N-dihydroxy-5-methyl-benzamidine); LC-MS: $t_R$=0.72 min; [M+1]⁺=235.09; ¹H NMR (CD₃OD): δ 7.31 (s, 1H), 7.29 (s, 1H), 6.10 (m, 1H), 5.43 (dd, J=17.0, 1.5 Hz, 1H), 5.27 (dd, J=10.3, 1.2 Hz, 1H), 4.81 (s br, 3H), 4.31 (d, J=5.6 Hz, 2H), 2.67 (q, J=7.6 Hz, 2H), 2.30 (s, 3H), 1.23 (t, J=7.6 Hz, 4H).

4,N-Dihydroxy-3-methyl-5-propyl-benzamidine

The title compound is prepared from commercially available 2-methyl-6-propyl-phenol in analogy to literature procedures (e.g. B. Roth et al. *J. Med. Chem.* 31 (1988) 122-129; and literature cited for 3-ethyl-4,N-dihydroxy-5-methyl-benzamidine); LC-MS: $t_R$=0.54 min; [M+1]⁺=209.43; ¹H NMR (D₆-DMSO): δ 0.90 (t, J=7.3 Hz, 3H), 1.48-1.59 (m, 3H), 2.19 (s, 3H), 2.56 (t, J=7.3 Hz, 2H), 7.37 (s, 1H), 7.40 (s, 1H), 9.34 (s, 1H).

3,5-Diethyl-4,N-dihydroxy-benzamidine

The title compound is prepared from commercially available 2,6-diethylaniline following literature procedures (G. G. Ecke, J. P. Napolitano, A. H. Filbey, A. J. Kolka, *J. Org. Chem.* 22 (1957) 639-642; and literature cited for 3-ethyl-4,N-dihydroxy-5-methyl-benzamidine).

3-Chloro-4,N-dihydroxy-5-methoxy-benzamidine

The title compound is prepared from commercially available 3-chloro-4-hydroxy-5-methoxybenzaldehyde in analogy to literature procedures (see 3-ethyl-4,N-dihydroxy-5-methyl-benzamidine); LC-MS: $t_R$=0.49 min; [M+1]⁺=216.96; ¹H NMR (D₆-DMSO): δ 3.84 (s, 3H), 5.78 (s, 1H), 7.22 (d, J=1.8 Hz, 1H), 7.26 (d, J=1.8 Hz, 1H), 9.52 (s br, 1H).

4-Allyloxy-3-chloro-N-hydroxy-5-methoxy-benzamidine

The title compound is prepared by allylating commercially available 3-chloro-4-hydroxy-5-methoxybenzaldehyde (see 4-allyloxy-3-ethyl-N-hydroxy-5-methyl-benzamidine). The aldehyde is then transformed into the corresponding hydroxyamidine according to literature procedures (see 3-ethyl-4,N-dihydroxy-5-methyl-benzamidine); LC-MS: $t_R$=0.69 min; [M+1]⁺=257.26.

4,N-Dihydroxy-3-methoxy-5-methyl-benzamidine

The title compound is prepared from commercially available 2-methoxy-6-methyl-phenol in analogy to literature procedures (see 3-ethyl-4,N-dihydroxy-5-methyl-benzamidine); LC-MS: $t_R$=0.50 min; [M+H]⁺=197.23.

3-Chloro-4,N-dihydroxy-5-methyl-benzamidine

The title compound is prepared from commercially available 2-chloro-6-methyl-phenol in analogy to literature procedures (e.g. B. Roth et al. *J. Med. Chem.* 31 (1988) 122-129; and literature cited for 3-ethyl-4,N-dihydroxy-5-methyl-benzamidine); 3-chloro-4-hydroxy-5-methyl-benzaldehyde: LC-MS: $t_R$=0.49 min; [M+1]⁺=201.00; ¹H NMR δ 2.24 (s, 2H), 2.35 (s, 4H), 5.98 (s br, 1H), 7.59 (d, J=1.8 Hz, 1H), 7.73 (d, J=1.8 Hz, 1H), 9.80 (s, 1H); 3-chloro-4,N-dihydroxy-5-methyl-benzamidine: ¹H NMR (D₆-DMSO): δ 2.21 (s, 3H), 5.72 (s br, 2H), 7.40 (s, 1H), 7.48 (s, 1H), 9.29 (s br, 1H), 9.48 (s br, 1H).

4-Allyloxy-3,5-dichloro-N-hydroxy-benzamidine

The title compound is prepared by allylating commercially available ethyl 3,5-dichloro-4-hydroxy-benzoate followed by transforming the benzoic acid obtained after saponification into the corresponding N-hydroxybenzamidine in analogy to the procedure described for 2-(ethyl-methyl-amino)-N-hydroxy-6-methyl-isonicotinamidine; LC-MS: $t_R$=0.71 min; [M+1]⁺=260.92.

4,N-Dihydroxy-2-methoxy-benzamidine

The title compound is prepared from commercially available 4-hydroxy-2-methoxybenzaldehyde in analogy to literature procedures (see 3-ethyl-4,N-dihydroxy-5-methyl-benzamidine); LC-MS: $t_R$=0.41 min; [M+1]⁺=183.06; ¹H NMR (D₆-DMSO): δ 3.74 (s, 3H), 5.47 (s, 2H), 6.35 (dd, J=8.3, 1.5 Hz, 1H), 6.45 (s, 1H), 7.21 (d, J=8.5 Hz, 1H), 9.42 (s, 2H).

N-Hydroxy-2,4-dimethoxy-benzamidine

The title compound is prepared from commercially available 2,4-dimethoxy-benzonitrile in analogy to literature procedures (e.g. E. Meyer, A. C. Joussef, H. Gallardo, *Synthesis* 2003, 899-905); LC-MS: $t_R$=0.59 min; [M+1]⁺=197.52; ¹H NMR (D₆-DMSO): δ 3.78 (s, 3H), 3.79 (s, 3H), 5.50 (s, 2H), 6.52 (d, J=8.5 Hz, 1H), 6.59 (s, 1H), 7.33 (d, J=8.5 Hz, 1H), 9.27 (s, 1H).

N-Hydroxy-2,3-dimethoxy-benzamidine

The title compound is prepared from commercially available 2,3-dimethoxy-benzonitrile in analogy to literature procedures (e.g. E. Meyer, A. C. Joussef, H. Gallardo, *Synthesis* 2003, 899-905); LC-MS: $t_R$=0.58*min; [M+1]⁺=197.25.

2-Chloro-4,N-dihydroxy-benzamidine

The title compound is prepared from commercially available 2-chloro-4-hydroxy-benzonitrile in analogy to literature procedures (e.g. E. Meyer, A. C. Joussef, H. Gallardo, Synthesis 2003, 899-905); LC-MS: $t_R$=0.29 min; $[M+1]^+$= 186.98.

4-Allyloxy-N-hydroxy-2-methyl-benzamidine a) To a dark yellow solution of 4-bromo-3-methyl-phenol (4.68 g, 25 mmol) in isopropanol (60 mL) and 3 N aq. NaOH (20 mL), allylchloride (8.18 g, 107 mmol) is added. The mixture is stirred at 70° C. for 3 h before it is cooled to rt, diluted with diethyl ether and washed with 1 N aq. NaOH solution (275 mL) and 1 M aq. HCl solution (70 mL) followed by brine (70 mL). The org. extract is dried over $MgSO_4$, filtered, concentrated and dried to give crude 4-allyloxy-1-bromo-2-methyl-benzene (5.67 g) as a yellow oil; LC-MS: $t_R$=0.59 min; $[M+1]^+$=not detectable; $^1$H NMR ($CDCl_3$): δ 2.38 (s, 3H), 4.52 (dt, J=5.3, 1.5 Hz, 2H), 5.29-5.34 (m, 1H), 5.39-5.46 (m, 1H), 6.00-6.11 (m, 1H), 6.65 (dd, J=8.8, 3.0 Hz, 1H), 6.83 (d, J=3.0 Hz, 1H), 7.41 (d, J=8.5 Hz, 1H).

b) To a solution of 4-allyloxy-1-bromo-2-methyl-benzene (10.87 g, 47.9 mmol) in THF (125 mL), a solution of n-butyl lithium (45 mL, 1.5 M in diethyl ether) is added at −75° C. The mixture is stirred at −75° C. for 30 min before it is transferred via a double-tip needle into a cooled (0° C.) solution of dimethylcarbonate (12.93 g, 144 mmol) in THF (45 mL). The mixture is stirred at 0° C. for 2 h, then at rt for 20 h before the solvents are removed in vacuo. The remaining oil is evaporated twice from ethanol (100 mL) before it is dissolved in 2 M aq. LiOH solution (75 mL) and ethanol (100 mL). The mixture is stirred at rt for 2 days and at 60° C. for 1 h. The org. solvent is evaporated and the remaining solution is diluted with 0.5 M aq. NaOH solution and extracted with diethyl ether (100 mL). The org. extract is washed with 1 M aq. NaOH solution (150 mL). The combined basic aq. extracts are washed with diethyl ether (100 mL), acidified with 25% aq. HCl and extracted with DCM (2×100 mL). The DCM extracts are combined, dried over $MgSO_4$, filtered, concentrated and dried under high vacuum to give 4-allyloxy-2-methyl-benzoic acid (5.83 g) as an orange solid; LC-MS: $t_R$=0.87 min; $[M+1]^+$=not detectable; $^1$H NMR ($CDCl_3$): δ 2.66 (s, 3H), 4.62 (dt, J=5.3, 1.5 Hz, 2H), 5.34 (dq, J=10.5, 1.5 Hz, 1H), 5.45 (dq, J=17.1, 1.5 Hz, 1H), 6.03-6.13 (m, 1H), 6.79-6.83 (m, 2H), 8.08 (d, J=9.5 Hz, 1H).

c) The above 4-allyloxy-2-methyl-benzoic acid is transformed to the title compound in analogy to the procedures given for 2-(ethyl-methyl-amino)-N-hydroxy-6-methyl-isonicotinamidine; LC-MS: $t_R$=60 min; $[M+1]^+$=207.09.

4-Amino-3-chloro-N-hydroxy-5-methyl-benzamidine

The title compound is prepared from commercially available 4-amino-3-chloro-5-methylbenzonitrile in analogy to 4,N-dihydroxy-3,5-dimethyl-benzamidine; LC-MS: $t_R$=0.50 min; $[M+1]^+$=200.01.

N-[2-Ethyl-4-(N-hydroxycarbamimidoyl)-phenyl]-acetamide

The title compound is prepared from commercially available N-(4-cyano-2-ethyl-phenyl)-acetamide in analogy to 4,N-dihydroxy-3,5-dimethyl-benzamidine; LC-MS: $t_R$=0.52 min; $[M+1]^+$=222.21.

4-Allyloxy-N-hydroxy-2-methoxy-benzamidine

The title compound is prepared from commercially available 4-hydroxy-2-methoxy-benzaldehyde following literature procedures (references cited for 3-ethyl-4,N-dihydroxy-5-methyl-benzamidine); LC-MS: $t_R$=0.64 min; $[M+1]^+$= 223.24; $^1$H NMR ($d^6$-DMSO): δ 9.33 (s br, 1H), 7.30 (d, J=8.2 Hz, 1H), 6.60 (d, J=2.3 Hz, 1H), 6.50 (dd, J=2.3, 8.2 Hz, 1H), 6.10-5.94 (m, 1H), 5.50 (s, 2H), 5.40 (d, J=17.0 Hz, 1H), 5.24 (d, J=10.6 Hz, 1H), 4.57 (d, J=4.7 Hz, 2H), 3.76 (s, 3H).

4-Allyloxy-3,5-dimethyl-benzoic acid hydrazide

To a solution of 4-allyloxy-3,5-dimethyl-benzoic acid (Lit.: see U.S. Pat. No. 3,262,946) (5.26 g, 25.5 mmol) in $CHCl_3$ (75 mL) is added thionylchloride (7.5 mL) and the mixture is heated at reflux for 2 h. The mixture is evaporated and the residue dissolved in DCM (50 mL), and added to a cooled (0° C.) solution of 1M hydrazine in THF (75 mL) in DCM (250 mL). The mixture is slowly warmed to rt during 15 h, diluted with diethyl ether (150 mL) and washed with 1M aq. HCl (5×50 mL). The aq. extracts are washed with diethyl ether (50 mL) and the org. phases are discarded. The aq. extracts are basified with 33% aq. KOH and extracted with DCM (5×50 mL). The org. extracts are dried ($Na_2SO_4$), filtered and evaporated to give the title compound (5.39 g) as a white solid; LC-MS: $t_R$=0.71 min; $[M+1]^+$=221.20.

3-[4-(N-Hydroxycarbamimidoyl)-2,6-dimethyl-phenyl]-propionic acid tert-butyl ester a) To an ice-cooled solution of 4-hydroxy-3,5-dimethyl-benzoic acid methyl ester (7.52 g, 41.7 mmol) in DCM (250 mL) and pyridine (10 mL), trifluoromethanesulfonic acid anhydride (13.0 g, 45.9 mmol) is added over a period of 20 min. Upon complete addition, the ice bath is removed and the reaction is stirred for further 1 h at rt. The mixture is diluted with DCM (150 mL), washed with 10% aq. citric acid solution followed by brine, dried over $MgSO_4$, filtered and evaporated. The residue is purified by FC on silica gel eluting with heptane:EA 9:1 to give 3,5-dimethyl-4-trifluoromethanesulfonyloxy-benzoic acid methyl ester (11.8 g) as colourless fine needles; LC-MS: $t_R$=1.08 min.

b) To a stirred solution of the above triflate (11.8 g, 37.8 mmol) in dry DMF (155 mL) is sequentially added triethylamine (7.6 g, 75.6 mmol), tert.-butyl acrylate (48.4 g, 378 mmol), DPPP (779 mg, 1.89 mmol) and $Pd(OAc)_2$ (424 mg, 1.89 mmol) under nitrogen. The mixture is stirred at 115° C. for 18 h before another portion of DPPP (160 mg, 0.39 mmol) and $Pd(OAc)_2$ (80 mg, 0.36 mmol) is added. Stirring is continued for 4 h at 115° C. before the mixture is cooled to rt, diluted with diethyl ether (350 mL) and washed with 1 N aq. HCl, followed by sat. aq. $NaHCO_3$ solution. The org. extract is dried over $MgSO_4$, filtered and evaporated. The residue is purified by FC on silica gel eluting with heptane:EA 4:1 to give 4-(2-tert-butoxycarbonyl-vinyl)-3,5-dimethyl-benzoic acid methyl ester (11.21 g) as a colourless solid; LC-MS: $t_R$=1.09 min.

c) To a solution of 4-(2-tert-butoxycarbonyl-vinyl)-3,5-dimethyl-benzoic acid methyl ester (11.2 g, 38.6 mmol) in ethanol (50 mL) and THF (50 mL), Pd/C (1.0 g, 10% Pd) is added. The mixture is stirred for 16 h at rt under 2.5 bar of $H_2$. The catalyst is filtered off and the filtrate is concentrated and dried under HV to give 4-(2-tert-butoxycarbonyl-ethyl)-3,5-dimethyl-benzoic acid methyl ester (10.8 g) as a colourless oil; LC-MS: $t_R$=1.08 min.

d) To a solution of 4-(2-tert-butoxycarbonyl-ethyl)-3,5-dimethyl-benzoic acid methyl ester (10.8 g, 37.0 mmol) in ethanol (100 mL) a 2 M aq. solution of LiOH (50 mL) is added at 0° C. The turbid mixture is stirred at 0° C. for 30 min, then at rt for 4 h. The mixture is diluted with 10% aq. citric acid solution and extracted three times with diethyl ether. The combined org. extracts are dried over MgSO$_4$, filtered and concentrated. The solid residue is suspended in diethyl ether/heptane, stirred at rt, and filtered. The slurry procedure in diethyl ether/heptane is repeated. The solid material is collected and dried under HV to give 4-(2-tert-butoxycarbonyl-ethyl)-3,5-dimethyl-benzoic acid (5.09 g) as a white crystalline powder; LC-MS: t$_R$=0.95 min, [M+1]$^+$=279.14; $^1$H NMR (CDCl$_3$): δ 1.47 (s, 9H), 2.30-2.40 (m, 2H), 2.39 (s, 6H), 2.94-3.03 (m, 2H), 7.75 (s, 2H).

e) To a suspension of 4-(2-tert-butoxycarbonyl-ethyl)-3,5-dimethyl-benzoic acid (8.00 g, 28.7 mmol) in isopropanol (100 mL), HOBt (4.27 g, 31.6 mmol) followed by EDC hydrochloride (6.34 g, 33.1 mmol) is added. After stirring at rt for 1 h, 25% aq. ammonia (16.1 mL) is added. Stirring is continued for 30 min before the isopropanol is evaporated under reduced pressure. The remaining solution is diluted with isopropyl acetate (200 mL), washed three times with approximately 0.5 N aq. NaHCO$_3$ solution (100 mL) followed by water (50 mL), dried over MgSO$_4$, filtered, concentrated and dried to give 3-(4-carbamoyl-2,6-dimethyl-phenyl)-propionic acid tert-butyl ester (7.5 g) as an off-white solid.

f) To an ice-cooled solution of 3-(4-carbamoyl-2,6-dimethyl-phenyl)-propionic acid tert-butyl ester (7.00 g, 25.2 mmol) and triethylamine (7.66 g, 75.7 mmol) in DCM (100 mL), trifluoroacetic anhydride (6.06 g, 28.8 mmol) is added slowly so that the reaction temperature stays below 15° C. The clear yellow solution is stirred at rt for 1 h before it is washed twice with water (100 mL) and concentrated. The crude product is purified by recrystallisation from methanol to give 3-(4-cyano-2,6-dimethyl-phenyl)-propionic acid tert-butyl ester (4.2 g) as a white solid, $^1$H NMR (CDCl$_3$): δ 1.48 (s, 9H), 2.33-2.37 (m, 2H), 2.38 (s, 6H), 2.94-3.01 (m, 2H), 7.31 (s, 2H).

g) A solution of 3-(4-cyano-2,6-dimethyl-phenyl)-propionic acid tert-butyl ester (4.1 g, 15.8 mmol), hydroxylamine hydrochloride (1.65 g, 23.7 mmol) and triethylamine (3.20 g, 31.6 mmol) in methanol (40 mL) is refluxed for 2 h before the solvent is removed in vacuo. The residue is taken up in isopropyl acetate (50 mL) and washed twice with water (50 mL). The org. extract is dried over MgSO$_4$, filtered, evaporated and dried to give 3-[4-(N-hydroxycarbamimidoyl)-2,6-dimethyl-phenyl]-propionic acid tert-butyl ester (4.4 g) as a white solid.

3-[2-Ethyl-4-(N-hydroxycarbamimidoyl)-6-methyl-phenyl]-propionic acid tert-butyl ester The title compound is prepared in analogy to 3-[4-(N-hydroxycarbamimidoyl)-2,6-dimethyl-phenyl]-propionic acid tert-butyl ester; $^1$H NMR (CDCl$_3$): δ 1.26 (t, J=7.5 Hz, 3H), 2.34-2.41 (m, 5H), 2.70 (q, J=7.8 Hz, 2H), 2.94-3.01 (m, 2H), 4.85 (s br, 1H), 7.28 (s, 1H), 7.32 (s, 1H).

4-(N-Hydroxycarbamimidoyl)-benzoic acid ethyl ester

The title compound is prepared in analogy to 3-[4-(N-hydroxycarbamimidoyl)-2,6-dimethyl-phenyl]-propionic acid tert-butyl ester (step g) starting from ethyl 4-cyanobenzoate; LC-MS: t$_R$=0.55 min, [M+1]$^+$=209.05; $^1$H NMR (D$_6$-DMSO): δ 1.33 (t, J=7.0 Hz, 3H), 4.32 (q, J=7.0 Hz, 2H), 5.94 (s, 2H), 7.83 (d, J=8.0 Hz, 2H), 7.95 (d, J=7.8 Hz, 2H), 9.91 (s, 1H).

[4-(N-Hydroxycarbamimidoyl)-phenyl]-acetic acid a) [4-(N-Hydroxycarbamimidoyl)-phenyl]-acetic acid methyl ester is prepared from methyl (4-cyanophenyl)acetate in analogy to 3-[4-(N-hydroxycarbamimidoyl)-2,6-dimethyl-phenyl]-propionic acid tert-butyl ester (step g); LC-MS: t$_R$=0.59 min, [M+1]$^+$=209.06.

b) A solution of the above [4-(N-hydroxycarbamimidoyl)-phenyl]-acetic acid methyl ester (2.0 g, 9.61 mmol) in 2 M aq. HCl is stirred at 65° C. for 16 h, then at 80° C. for 24 h before it is concentrated and dried to give sufficiently pure title compound (2.0 g) as a white solid; LC-MS: t$_R$=0.34 min, [M+1]$^+$=195.07.

N-Hydroxy-4-hydroxymethyl-benzamidine

The title compound is prepared in analogy to 3-[4-(N-hydroxycarbamimidoyl)-2,6-dimethyl-phenyl]-propionic acid tert-butyl ester (step g) starting from 4-hydroxymethyl-benzonitrile; LC-MS: t$_R$=0.21 min, [M+1]$^+$=167.04.

N-Hydroxy-4-(2-hydroxy-ethyl)-benzamidine

The title compound is prepared in analogy to 3-[4-(N-hydroxycarbamimidoyl)-2,6-dimethyl-phenyl]-propionic acid tert-butyl ester (step g) starting from 4-(2-hydroxy-ethyl)-benzonitrile; LC-MS: t$_R$=0.50*min, [M+1]+=181.27.

N-Hydroxy-4-propoxy-benzamidine

The title compound is prepared in analogy to 3-[4-(N-hydroxycarbamimidoyl)-2,6-dimethyl-phenyl]-propionic acid tert-butyl ester (step g) starting from 4-propoxy-benzonitrile; LC-MS: t$_R$=0.71*min, [M+1]$^+$=195.28.

N-Hydroxy-4-vinyl-benzamidine

The title compound is prepared in analogy to 3-[4-(N-hydroxycarbamimidoyl)-2,6-dimethyl-phenyl]-propionic acid tert-butyl ester (step g) starting from 4-vinyl-benzonitrile; LC-MS: t$_R$=0.66*min, [M+1]$^+$=162.92.

3-Ethyl-4-hydroxy-5-methyl-benzoic acid a) To an ice-cold solution of H$_2$SO$_4$ (150 mL) in water (250 mL), 2-ethyl-6-methylaniline (15.0 g, 111 mmol) is added. The solution is treated with ice (150 g) before a solution of NaNO$_2$ (10.7 g, 155 mmol) in water (150 mL) and ice (50 g) is added dropwise. The mixture is stirred at 0° C. for 1 h. 50% aq. H$_2$SO$_4$ (200 mL) is added and stirring is continued at rt for 18 h. The mixture is extracted with DCM, the org. extracts are dried over MgSO$_4$ and evaporated. The crude product is purified by CC on silica gel eluting with heptane:EA 9:1 to give 2-ethyl-6-methyl-phenol (8.6 g) as a crimson oil; LC-MS: t$_R$=0.89 min; $^1$H NMR (CDCl$_3$): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condensor and the mixture is refluxed for 3 h. The mixture is cooled to rt, diluted with water (100 mL) and extracted with EA. The org. extract is washed with sat. aq. NaHCO$_3$, dried over MgSO$_4$ and evaporated. The remaining solid is dissolved in EA and treated with heptane to initialize crystallisation. The solid material is collected and dried to give 3-ethyl-4-hydroxy-5-methyl-benzaldehyde (3.13 g) as a colourless crystalline powder, $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

c) To a solution of 3-ethyl-4-hydroxy-5-methyl-benzaldehyde (78.8 g, 0.48 mol) in DMSO (585 mL), a solution of $NaH_2PO_4$ dihydrate (17.3 g, 0.144 mol) in water (160 mL) is added over a period of 13 min. The mixture is stirred at rt and a solution of $NaClO_2$ (65.17 g, 0.577 mol) in water (160 mL) is added while the mixture is cooled with an ice-bath. The mixture is stirred for 1 h before a second portion of $NaClO_2$ (43.44 g, 0.480 mol) in water (100 mL) is added while the temperature is kept between 25 and 40° C. with an ice-bath. The yellow suspension is stirred at rt for 24 h before it is acidified with 32% aq. HCl to pH 2-3. The mixture is extracted with TBME (250 mL), the org. extract is washed with water, and the washings are extracted back with TBME. The solvent of the combined org. extracts is evaporated to give crude 3-ethyl-4-hydroxy-5-methyl-benzoic acid (80.3 g) as a yellow solid.

4-Benzyloxy-3-ethyl-5-methyl-benzoic acid hydrazide a) To a solution of 3-ethyl-4-hydroxy-5-methyl-benzaldehyde (34.9 g, 0.213 mol, prepared from 2-ethyl-6-methyl-phenol according to the literature cited for 3-ethyl-4,N-dihydroxy-5-methyl-benzamidine) in MeCN (350 mL), $K_2CO_3$ (58.7 g, 0.425 mol) and benzylbromide (36.4 g, 0.213 mol) is added. The mixture is stirred at 60° C. for 2 h before it is cooled to rt, diluted with water and extracted twice with EA. The org. extracts are washed with water and concentrated to give crude 4-benzyloxy-3-ethyl-5-methyl-benzaldehyde (45 g) as an orange oil. $^1$H NMR (CDCl$_3$): δ 1.29 (t, J=7.5 Hz, 3H), 2.40 (s, 3H), 2.77 (q, J=7.8 Hz, 2H), 4.90 (s, 2H), 7.31-7.52 (m, 5H), 7.62 (d, J=1.5 Hz, 1H), 7.66 (d, J=1.8 Hz, 1H), 9.94 (s, 1H).

b) To a mixture of 4-benzyloxy-3-ethyl-5-methyl-benzaldehyde (132 g, 0.519 mol) and 2-methyl-2-butene (364 g, 5.19 mol) in tert.-butanol (1500 mL), a solution of $NaH_2PO_4$ dihydrate (249 g, 2.08 mol) in water (1500 mL) is added. To this mixture, $NaClO_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The org. layer is separated and washed with 20% aq. NaHS solution (1500 mL) and water (500 mL). The org. phase is then extracted three times with 0.5 N aq. NaOH (1000 mL), the aq. phase is acidified with 25% aq. HCl (500 mL) and extracted twice with TBME (1000 mL). These org. extracts are combined and evaporated to dryness to give 4-benzyloxy-3-ethyl-5-methyl-benzoic acid; $^1$H NMR (D$_6$-DMSO): δ 1.17 (t, J=7.5 Hz, 3H), 2.31 (s, 3H), 2.67 (q, J=7.5 Hz, 2H), 4.86 (s, 2H), 7.34-7.53 (m, 5H), 7.68 (s, 2H), 12.70 (s, 1H).

c) 4-Benzyloxy-3-ethyl-5-methyl-benzoic acid is converted to 4-benzyloxy-3-ethyl-5-methyl-benzoic acid hydrazide following step c) of the preparation of 4-allyloxy-3,5-dimethyl-benzoic acid hydrazide; LC-MS: $t_R$=0.82 min, [M+1]$^+$=285.44.

Methanesulfonic acid 2,2-dimethyl-[1,3]dioxan-5-yl methyl ester

The title compound is prepared following the procedures given in B. Xu, A. Stephens, G. Kirschenheuter, A. F. Greslin, X. Cheng, J. Sennelo, M. Cattaneo, M. L. Zighetti, A. Chen, S.-A. Kim, H. S. Kim, N. Bischofberger, G. Cook, K. A. Jacobson, *J. Med. Chem.* 45 (2002) 5694-5709.

Example 1 rac-3-{4-[5-(2-Dimethylamino-6-methyl-pyridin-4-yl)-[1,2,4]oxadiazol-3-yl]-2-ethyl-6-methyl-phenoxy}-propane-1,2-diol a) To a suspension of 2-dimethylamino-6-methyl-isonicotinic acid (331 mg, 1.64 mmol) in DCM (40 mL) and Hünig's base (2.85 mL, 16.4 mmol), PyBOP (1.16 g, 2.22 mmol) followed by 4-allyloxy-3-ethyl-N-hydroxy-5-methyl-benzamidine (225 mg, 0.96 mmol) is added. The beige suspension is stirred at rt for 1 h before it is diluted with DCM (150 mL), washed with 1 N aq. $KHSO_4$ solution and brine, dried over $Na_2SO_4$, filtered and concentrated. The crude product is purified by MPLC on silica gel eluting with EA to give the hydroxyamidine ester intermediate; LC-MS: $t_R$=0.85 min; [M+1]$^+$=397.17. This material is dissolved in dioxane (30 mL) and the resulting solution is stirred at 95° C. for 16 h. The solvent is evaporated and the crude product is purified by MPLC on silica gel eluting with EA to give {4-[3-(4-allyloxy-3-ethyl-5-methyl-phenyl)-[1,2,4]oxadiazol-5-yl]-6-methyl-pyridin-2-yl}-dimethyl-amine (81 mg) as a beige resin; LC-MS: $t_R$=0.95 min; [M+1]$^+$=379.15.

b) To a solution of {4-[3-(4-allyloxy-3-ethyl-5-methyl-phenyl)-[1,2,4]oxadiazol-5-yl]-6-methyl-pyridin-2-yl}-dimethyl-amine (81 mg, 0.193 mmol) in acetone (15 mL), a solution of 4-methylmorpholine-4-oxyde hydrate (114 mg, 0.845 mmol) in water (3 mL) followed by $OsO_4$ (15 mg, 0.06 mmol) is added. The mixture is stirred at 45° C. for 16 h before the solvent is removed in vacuo. The crude product is first purified on prep. TLC plates with DCM containing 25% of methanol followed by prep. HPLC to give rac-3-{4-[5-(2-dimethylamino-6-methyl-pyridin-4-yl)-[1,2,4]oxadiazol-3-yl]-2-ethyl-6-methyl-phenoxy}-propane-1,2-diol (7 mg) as a colourless resin; LC-MS: $t_R$=0.74 min; [M+1]$^+$=413.20; $^1$H NMR (CDCl$_3$): δ 1.33 (t, J=7.5 Hz, 3H), 2.05 (s br, 1H), 2.41 (s, 3H), 2.53 (s, 3H), 2.77 (q, J=7.5 Hz, 2H), 3.20 (s, 6H), 3.81-4.00 (m, 4H), 4.13-4.20 (m, 1H), 7.08 (s, 1H), 7.16 (s, 1H), 7.88 (s, 1H), 7.89 (s, 1H).

Example 2

4-{5-[2-(Ethyl-methyl-amino)-6-methyl-pyridin-4-yl]-[1,2,4]oxadiazol-3-yl}-2,6-dimethyl-phenol a) To a cooled solution (0° C.) of 4,N-dihydroxy-3,5-dimethyl-benzamidine (1.12 g, 6.19 mmol), 2-chloro-6-methyl-isonicotinic acid (1.06 g, 6.19 mmol) and Hünig's base (1.20 g, 9.29 mmol) in DCM (30 mL), PyBOP (3.55 g, 6.81 mmol) is added. The mixture is stirred at 0° C. and is warmed to rt overnight. The white suspension is diluted with EA (200 mL), washed four times with 1 N aq. $KHSO_4$ (50 mL), dried over $MgSO_4$, filtered and concentrated to give the hydroxyamidine ester intermediate as a yellow-beige solid; LC-MS: $t_R$=0.91 min; [M+1]$^+$=334.01. This material is dissolved in dioxane (60 mL) and the resulting solution is stirred at 95° C. for 4 h. The mixture is cooled and the solvent is removed in vacuo. The crude product is purified by MPLC on silica gel to give 4-[5-(2-chloro-6-methyl-pyridin-4-yl)-[1,2,4]oxadiazol-3-yl]-2,6-dimethyl-phenol (935 mg) as a yellow solid; LC-MS: $t_R$=1.03 min; [M+1]$^+$=316.20.

b) To a solution of 4-[5-(2-chloro-6-methyl-pyridin-4-yl)-[1,2,4]oxadiazol-3-yl]-2,6-dimethyl-phenol (549 mg, 1.74 mmol) and Na tert.-butylate (346 mg, 3.60 mmol) in ethyl-methylamine (10 mL), Xantphos (106 mg, 0.18 mmol) and Pd(OAc)$_2$ (47 mg, 0.21 mmol) is added. The mixture is stirred in an autoclave at 80° C. for 24 h. The dark mixture is cooled to rt, diluted with EA (200 mL), washed three times with sat. aq. NaHCO$_3$-solution, dried over MgSO$_4$, filtered and concentrated. The crude product is purified by MPLC on silica gel eluting with EA containing 20% of methanol to give 4-{5-[2-(ethyl-methyl-amino)-6-methyl-pyridin-4-yl]-[1,2,4]oxadiazol-3-yl}-2,6-dimethyl-phenol (119 mg) as a yellow solid; LC-MS: $t_R$=0.83 min; [M+1]$^+$=339.10; $^1$H NMR (D$_6$-DMSO): δ 1.12 (m, 3H), 2.26 (s, 6H), 2.43 (s, 3H), 2.88-2.98 (m, 2H), 3.07 (s, 3H), 7.00 (s, 1H), 7.08 (s, 1H), 7.67 (s br, 1H), 7.68 (s, 1H), 8.94 (s br, 1H).

Example 3

(R)-3-(4-{5-[2-(Ethyl-methyl-amino)-6-methyl-pyridin-4-yl]-[1,2,4]oxadiazol-3-yl}-2,6-dimethyl-phenoxy)-propane-1,2-diol To a solution of 4-{5-[2-(ethyl-methyl-amino)-6-methyl-pyridin-4-yl]-[1,2,4]oxadiazol-3-yl}-2,6-dimethyl-phenol (55 mg, 0.163 mmol) in isopropanol (3 mL) and 3 N aq. NaOH (0.5 mL), (R)-3-chloro-1,2-propanediol (98 mg, 0.894 mmol) is added. The mixture is stirred at 65° C. for 72 h before another portion of (R)-3-chloro-1,2-propanediol (98 mg, 0.894 mmol) is added. Stirring is continued at 65° C. for 4 days before a third portion of (R)-3-chloro-1,2-propanediol (98 mg, 0.894 mmol) is added. After stirring for another 48 h, the mixture is diluted with EA (50 mL) and washed with 1 N aq. NaOH (10 mL) followed by brine (10 mL), dried over MgSO$_4$, filtered and concentrated. The crude product is purified on prep. TLC plates with DCM containing 10% of 7 N NH$_3$ in methanol and 5% of methanol to give (R)-3-(4-{5-[2-(ethyl-methyl-amino)-6-methyl-pyridin-4-yl]-[1,2,4]oxadiazol-3-yl}-2,6-dimethyl-phenoxy)-propane-1,2-diol (25 mg) as a yellow solid; LC-MS: $t_R$=0.73 min; [M+1]$^+$=413.14.

Example 4

(S)-3-(4-{5-[2-(Ethyl-methyl-amino)-6-methyl-pyridin-4-yl]-[1,2,4]oxadiazol-3-yl}-2,6-dimethyl-phenoxy)-propane-1,2-diol (S)-3-(4-{5-[2-(ethyl-methyl-amino)-6-methyl-pyridin-4-yl]-[1,2,4]oxadiazol-3-yl}-2,6-dimethyl-phenoxy)-propane-1,2-diol is prepared in analogy to (R)-3-(4-{5-[2-(ethyl-methyl-amino)-6-methyl-pyridin-4-yl]-[1,2,4]oxadiazol-3-yl}-2,6-dimethyl-phenoxy)-propane-1,2-diol using (S)-3-chloro-1,2-propanediol; LC-MS: $t_R$=0.75 min; [M+1]$^+$=413.18.

Example 5

2-Ethyl-4-{5-[2-(ethyl-methyl-amino)-6-methyl-pyridin-4-yl]-[1,2,4]oxadiazol-3-yl}-6-methyl-phenol To a cooled solution (0° C.) of 3-ethyl-4,N-dihydroxy-5-methyl-benzamidine (420 mg, 2.16 mmol), 2-(ethyl-methyl-amino)-6-methyl-isonicotinic acid (420 mg, 2.16 mmol) and Hünig's base (1.40 g, 10.8 mmol) in DCM (30 mL), PyBOP (1.13 g, 2.16 mmol) is added. The mixture is stirred at 0° C. for 1 h. The mixture is diluted with EA (200 mL), washed three times with sat. aq. NaHCO$_3$-solution (50 mL), dried over MgSO$_4$, filtered and concentrated to give the hydroxyamidine ester intermediate as a yellow-beige solid; LC-MS: $t_R$=0.74 min; [M+1]$^+$=371.09. This material is dissolved in dioxane (60 mL) and the resulting solution is stirred at 95° C. for 4 h. The mixture is cooled and the solvent is removed in vacuo. The crude product is purified by MPLC on silica gel to give 2-ethyl-4-{5-[2-(ethyl-methyl-amino)-6-methyl-pyridin-4-yl]-[1,2,4]oxadiazol-3-yl}-6-methyl-phenol (420 mg) as a brownish solid; LC-MS: $t_R$=0.85 min; [M+1]$^+$=353.12.

Examples 6 and 7

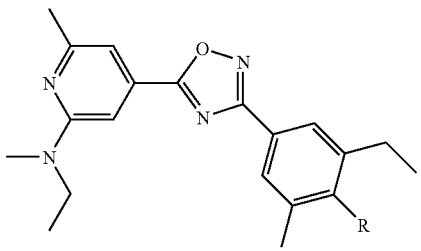

The following Examples are prepared starting from 2-ethyl-4-{5-[2-(ethyl-methyl-amino)-6-methyl-pyridin-4-yl]-[1,2,4]oxadiazol-3-yl}-6-methyl-phenol in analogy to previous Examples:

| Example | In analogy to Example | R | LC-MS $t_R$ (min) | [M + H]$^+$ |
|---|---|---|---|---|
| 6 | 3 | O⌒⌒OH / OH | 0.77 | 427.08 |
| 7 | 4 | O⌒⌒OH / OH | 0.76 | 427.43 |

Example 8 (Reference Example)

3-(2-Ethyl-4-{5-[2-(ethyl-methyl-amino)-6-methyl-pyridin-4-yl]-[1,2,4]oxadiazol-3-yl}-6-methyl-phenyl)-propionic acid To a solution of 2-(ethyl-methyl-amino)-6-methyl-isonicotinic acid (106 mg, 0.459 mmol) and DIPEA (178 mg, 1.38 mmol) in DMF (2 mL) is added PyBOP (253 mg, 0.486 mmol) at 0° C. The mixture is stirred for 15 min at 0° C. before 3-[2-ethyl-4-(N-hydroxycarbamimidoyl)-6-methyl-phenyl]-propionic acid tert-butyl ester (140 mg, 0.459 mmol) is added. Stirring is continued for 1 h at 0° C. The reaction mixture is diluted with water (2 mL) and sat. aq. NaHCO$_3$-solution and extracted three times with diethyl ether. The combined org. extracts are dried over MgSO$_4$, filtered and concentrated to give the crude hydroxyamidine ester intermediate; LC-MS: $t_R$=0.92 min; [M+1]$^+$=483.22. This material is dissolved in dioxane and then stirred at 80° C. for 15 h. The solvent is removed in vacuo to give crude 3-(2-ethyl-4-{5-[2-(ethyl-methyl-amino)-6-methyl-pyridin-4-yl]-[1,2,4]oxadiazol-3-yl}-6-methyl-phenyl)-propionic acid tert-butyl ester; LC-MS: $t_R$=1.03 min; [M+1]$^+$=463.31. The crude ester is dissolved in 6 N aq. HCl (10 mL) and stirred at 65° C. for 18 h. The mixture is concentrated and the crude product is purified by prep. TLC using DCM containing 11% of methanol as eluent to give 3-(2-ethyl-4-{5-[2-(ethyl-methyl-amino)-6-methyl-pyridin-4-yl]-[1,2,4]oxadiazol-3-yl}-6-methyl-phenyl)-propionic acid (5 mg) as a yellow resin; LC-MS: $t_R$=0.89 min; [M+1]$^+$=409.19.

Example 9

4-[5-(2-Diethylamino-6-methyl-pyridin-4-yl)-[1,2,4]oxadiazol-3-yl]-2,6-dimethyl-phenol 4-[5-(2-Diethylamino-6-methyl-pyridin-4-yl)-[1,2,4]oxadiazol-3-yl]-2,6-dimethyl-phenol (519 mg) is obtained as a beige powder in analogy to Example 5 starting from 2-diethylamino-6-methyl-isonicotinic acid (479 mg, 2.30 mmol) and 4,N-dihydroxy-3,5-dimethyl-benzamidine (435 mg, 2.42 mmol); LC-MS: $t_R$=0.86 min; [M+1]$^+$=353.12.

Examples 10 and 11

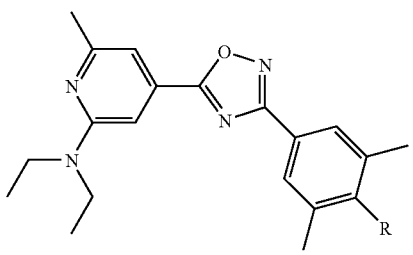

The following Examples are prepared starting from 4-[5-(2-diethylamino-6-methyl-pyridin-4-yl)[1,2,4]oxadiazol-3-yl]-2,6-dimethyl-phenol in analogy to previous Examples:

| Example | In analogy to Example | R | LC-MS $t_R$ (min) | [M + H]$^+$ |
|---|---|---|---|---|
| 10 | 3 | O~~OH, OH | 0.78 | 427.09 |
| 11 | 4 | O~~OH, OH | 0.78 | 427.07 |

Example 12

4-[5-(2-Diethylamino-6-methyl-pyridin-4-yl)-[1,2,4]oxadiazol-3-yl]-2-ethyl-6-methyl-phenol 4-[5-(2-Diethylamino-6-methyl-pyridin-4-yl)-[1,2,4]oxadiazol-3-yl]-2-ethyl-6-methyl-phenol (309 mg) is obtained in analogy to Example 5 starting from 2-diethylamino-6-methyl-isonicotinic acid (865 mg, 4.15 mmol) and 3-ethyl-4,N-dihydroxy-5-methyl-benzamidine (962 mg, 4.91 mmol); LC-MS: $t_R$=0.87 min; [M+1]$^+$=367.46.

Examples 13 and 14

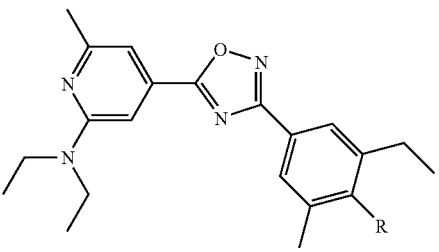

The following Examples are prepared starting from 4-[5-(2-diethylamino-6-methyl-pyridin-4-yl)-[1,2,4]oxadiazol-3-yl]-2-ethyl-6-methyl-phenol in analogy to previous Examples:

| Example | In analogy to Example | R | LCMS $t_R$ (min) | [M + H]$^+$ |
|---|---|---|---|---|
| 13 | 3 | O~~OH, OH | 0.81 | 441.19 |
| 14 | 4 | O~~OH, OH | 0.81 | 441.18 |

Example 15 rac-3-{4-[5-(2-Diethylamino-6-methyl-pyridin-4-yl)-[1,2,4]oxadiazol-3-yl]-2-ethyl-6-methyl-phenoxy}-propane-1,2-diol rac-3-{4-[5-(2-Diethylamino-6-methyl-pyridin-4-yl)-[1,2,4]oxadiazol-3-yl]-2-ethyl-6-methyl-phenoxy}-propane-1,2-diol is prepared in analogy to Example 1 starting from 2-diethylamino-6-methyl-isonicotinic acid and 4-allyloxy-3-ethyl-N-hydroxy-5-methyl-benzamidine; LC-MS: $t_R$=0.81 min; [M+1]$^+$=441.27; $^1$H NMR (CDCl$_3$): δ 1.25 (t, J=7.0 Hz, 6H), 1.33 (t, J=7.5 Hz, 3H), 2.41 (s, 3H), 2.50 (s, 3H), 2.77 (q, J=7.5 Hz, 2H), 3.63 (q, J=7.0 Hz, 4H), 3.85 (dd, J=11.3, 5.5 Hz, 1H), 3.91 (dd, J=11.5, 4.3 Hz, 1H), 3.94-3.99 (m, 2H), 4.14-4.20 (m, 1H), 7.01 (s, 1H), 7.10 (s, 1H), 7.88 (s, 1H), 7.89 (s, 1H).

Example 16

(R)-1-Amino-3-{4-[5-(2-diethylamino-6-methyl-pyridin-4-yl)-[1,2,4]oxadiazol-3-yl]-2-ethyl-6-methyl-phenoxy}-propan-2-ol a) To a solution of 4-[5-(2-diethylamino-6-methyl-pyridin-4-yl)-[1,2,4]oxadiazol-3-yl]-2-ethyl-6-methyl-phenol (500 mg, 1.36 mmol) in isopropanol (15 mL) and 3 N aq. NaOH (6 mL), (S)-epichlorohydrine (378 mg, 4.09 mmol) is added. The orange solution is stirred at rt for 24 h before another portion of (S)-epichlorohydrine is added. Stirring is continued for 24 h, the mixture is diluted with EA, washed with sat. aq. NaHCO$_3$-solution, dried over MgSO$_4$, filtered and concentrated. The crude product is purified by CC on silica gel eluting with heptane:EA 4:1 to give diethyl-{4-[3-((R)-3-ethyl-5-methyl-4-oxiranylmethoxy-phenyl)-[1,2,4]oxadiazol-5-yl]-6-methyl-pyridin-2-yl}-amine (430 mg) as a yellow oil; LC-MS: t$_R$=0.96 min; [M+1]$^+$=423.21.

b) The above epoxide is dissolved in 7 N NH$_3$ in methanol (20 mL) and the solution is stirred at 45° C. for 18 h. The solvent is evaporated and the crude product is purified by CC on silica gel eluting with DCM containing 5% of 7 N NH$_3$ in methanol to give (R)-1-amino-3-{4-[5-(2-diethylamino-6-methyl-pyridin-4-yl)-[1,2,4]oxadiazol-3-yl]-2-ethyl-6-methyl-phenoxy}-propan-2-ol (310 mg) as a yellow oil; LC-MS: t$_R$=0.71 min; [M+1]$^+$=440.26.

Example 17

N-(3-{4-[5-(2-Diethylamino-6-methyl-pyridin-4-yl)-[1,2,4]oxadiazol-3-yl]-2-ethyl-6-methyl-phenoxy}-(R)-2-hydroxy-propyl)-2-hydroxy-acetamide To a solution of (R)-1-amino-3-{4-[5-(2-diethylamino-6-methyl-pyridin-4-yl)-[1,2,4]oxadiazol-3-yl]-2-ethyl-6-methyl-phenoxy}-propan-2-ol (310 mg, 0.705 mmol), glycolic acid (59 mg, 0.776 mmol) and HOBt (114 mg, 0.846 mmol), EDC hydrochloride (149 mg, 0.776 mmol) is added. The mixture is stirred at rt for 1 h before it is diluted with sat. aq. NaHCO$_3$ and extracted twice with EA. The combined org. extracts are dried over MgSO$_4$, filtered and concentrated. The crude product is purified on prep. TLC plates with DCM containing 12% of methanol to give N-(3-{4-[5-(2-diethylamino-6-methyl-pyridin-4-yl)-[1,2,4]oxadiazol-3-yl]-2-ethyl-6-methyl-phenoxy}-(R)-2-hydroxy-propyl)-2-hydroxy-acetamide (296 mg) as an off-white powder; LC-MS: t$_R$=0.78 min; [M+1]$^+$=498.19.

Example 18

(S)-1-Amino-3-{4-[5-(2-diethylamino-6-methyl-pyridin-4-yl)-[1,2,4]oxadiazol-3-yl]-2-ethyl-6-methyl-phenoxy}-propan-2-ol a) To a solution of 4-[5-(2-diethylamino-6-methyl-pyridin-4-yl)-[1,2,4]oxadiazol-3-yl]-2-ethyl-6-methyl-phenol (110 mg, 0.30 mmol) in THF (9 mL), PPh$_3$ (150 mg, 0.57 mmol) and (R)-glycidol (42 mg, 0.57 mmol) are added. The mixture is cooled to 0° C. before DEAD (248 mg, 0.57 mmol) is added. The mixture stirred for 1 h and is warmed to rt. The solvent is evaporated and the crude product is purified by CC on silica gel eluting with heptane:EA 7:3 to give diethyl-{4-[3-((S)-3-ethyl-5-methyl-4-oxiranylmethoxy-phenyl)-[1,2,4]oxadiazol-5-yl]-6-methyl-pyridin-2-yl}-amine (119 mg) as a yellow oil; LC-MS: t$_R$=0.95 min; [M+1]$^+$=423.21.

b) The above epoxide is dissolved in 7 N NH$_3$ in methanol (20 mL) and the solution is stirred at 45° C. for 18 h. The solvent is evaporated to give crude (S)-1-amino-3-{4-[5-(2-diethylamino-6-methyl-pyridin-4-yl)-[1,2,4]oxadiazol-3-yl]-2-ethyl-6-methyl-phenoxy}-propan-2-ol (129 mg) as a yellow oil; LC-MS: t$_R$=0.71 min; [M+1]$^+$=440.30.

Example 19

N-(3-{4-[5-(2-Diethylamino-6-methyl-pyridin-4-yl)-[1,2,4]oxadiazol-3-yl]-2-ethyl-6-methyl-phenoxy}-(S)-2-hydroxy-propyl)-2-hydroxy-acetamide N-(3-{4-[5-(2-Diethylamino-6-methyl-pyridin-4-yl)-[1,2,4]oxadiazol-3-yl]-2-ethyl-6-methyl-phenoxy}-(S)-2-hydroxy-propyl)-2-hydroxy-acetamide is prepared in analogy to N-(3-{4-[5-(2-diethylamino-6-methyl-pyridin-4-yl)-[1,2,4]oxadiazol-3-yl]-2-ethyl-6-methyl-phenoxy}-(R)-2-hydroxy-propyl)-2-hydroxy-acetamide starting from (S)-1-amino-3-{4-[5-(2-diethylamino-6-methyl-pyridin-4-yl)-[1,2,4]oxadiazol-3-yl]-2-ethyl-6-methyl-phenoxy}-propan-2-ol; LC-MS: t$_R$=0.78 min; [M+1]$^+$=498.20; $^1$H NMR (CDCl$_3$): δ 1.24 (t, J=7.0 Hz, 6H), 1.32 (t, J=7.3 Hz, 3H), 2.39 (s, 3H), 2.49 (s, 3H), 2.75 (q, J=7.5 Hz, 2H), 2.83 (s br, 1H), 3.44 (s br, 1H), 3.48-3.57 (m, 1H), 3.62 (q, J=6.8 Hz, 4H), 3.75-3.94 (m, 3H), 4.17-4.25 (m, 3H), 7.00 (s, 1H), 7.05 (t, J=4.5 Hz, 1H), 7.09 (s, 1H), 7.87 (s, 1H), 7.88 (s, 1H).

Example 20 rac-3-{4-[5-(2-Diethylamino-6-ethyl-pyridin-4-yl)-[1,2,4]oxadiazol-3-yl]-2-ethyl-6-methyl-phenoxy}-propane-1,2-diol rac-3-{4-[5-(2-Diethylamino-6-ethyl-pyridin-4-yl)-[1,2,4]oxadiazol-3-yl]-2-ethyl-6-methyl-phenoxy}-propane-1,2-diol is prepared in analogy to Example 1 starting from 2-diethylamino-6-ethyl-isonicotinic acid and 4-allyloxy-3-ethyl-N-hydroxy-5-methyl-benzamidine; LC-MS: t$_R$=0.86 min; [M+1]$^+$=455.30; $^1$H NMR (CDCl$_3$): δ 1.25 (t, J=7.0 Hz, 6H), 1.33 (q, J=7.3 Hz, 6H), 2.40 (s, 3H), 2.77 (q, J=7.5 Hz, 4H), 3.63 (q, J=7.0 Hz, 4H), 3.84 (dd, J=11.3, 5.5 Hz, 1H), 3.88-3.99 (m, 3H), 4.14-4.20 (m, 1H), 7.01 (s, 1H), 7.10 (s, 1H), 7.88 (s, 1H), 7.89 (s, 1H).

Example 21

4-{5-[2-(Isopropyl-methyl-amino)-6-methyl-pyridin-4-yl]-[1,2,4]oxadiazol-3-yl}-2,6-dimethyl-phenol 4-{5-[2-(Isopropyl-methyl-amino)-6-methyl-pyridin-4-yl]-[1,2,4]oxadiazol-3-yl}-2,6-dimethyl-phenol is prepared in analogy to Example 2 using isopropylmethylamine; LC-MS: t$_R$=0.86 min; [M+1]$^+$=353.12.

Example 22

(S)-3-(4-{5-[2-(Isopropyl-methyl-amino)-6-methyl-pyridin-4-yl]-[1,2,4]oxadiazol-3-yl}-2,6-dimethyl-phenoxy)-propane-1,2-diol (S)-3-(4-{5-[2-(Isopropyl-methyl-amino)-6-methyl-pyridin-4-yl]-[1,2,4]oxadiazol-3-yl}-2,6-dimethyl-phenoxy)-propane-1,2-diol is prepared in analogy to Example 3 from 4-{5-[2-(isopropyl-methyl-amino)-6-methyl-pyridin-4-yl]-[1,2,4]oxadiazol-3-yl}-2,6-dimethyl-phenol using (S)-3-chloro-1,2-propanediol; LC-MS: t$_R$=0.78 min; [M+1]$^+$=427.08.

Example 23

2-Ethyl-4-{5-[2-(isopropyl-methyl-amino)-6-methyl-pyridin-4-yl]-[1,2,4]oxadiazol-3-yl}-6-methyl-phenol 2-Ethyl-4-{5-[2-(isopropyl-methyl-amino)-6-methyl-pyridin-4-yl]-[1,2,4]oxadiazol-3-yl}-6-methyl-phenol is obtained as a yellow crystalline solid in analogy to Example 5 starting from 2-(isopropyl-methyl-amino)-6-methyl-isonicotinic acid and 3-ethyl-4,N-dihydroxy-5-methyl-benzamidine; LC-MS: t$_R$=0.88 min; [M+1]$^+$=367.49.

Example 24

(S)-3-(2-Ethyl-4-{5-[2-(isopropyl-methyl-amino)-6-methyl-pyridin-4-yl]-[1,2,4]oxa-diazol-3-yl}-6-methyl-phenoxy)-propane-1,2-diol (S)-3-(2-Ethyl-4-{5-[2-(isopropyl-methyl-amino)-6-methyl-pyridin-4-yl]-[1,2,4]oxa-diazol-3-yl}-6-methyl-phenoxy)-propane-1,2-diol is prepared from 2-ethyl-4-{5-[2-(isopropyl-methyl-amino)-6-methyl-pyridin-4-yl]-[1,2,4]oxadiazol-3-yl}-6-methyl-phenol and (S)-3-chloro-1,2-propanediol in analogy to Example 3; LC-MS: $t_R$=1.07 min; [M+1]$^+$=441.37; $^1$H NMR (CDCl$_3$): δ 1.24 (d, J=6.5 Hz, 6H), 1.33 (t, J=7.5 Hz, 3H), 2.05 (t, J=5.1 Hz, 1H), 2.41 (s, 3H), 2.51 (s, 3H), 2.73 (d, J=5.5 Hz, 1H), 2.78 (q, J=7.5 Hz, 2H), 2.97 (s, 3H), 3.81-4.00 (m, 4H), 4.12-4.21 (m, 1H), 4.95-5.05 (m, 1H), 7.06 (s, 1H), 7.13 (s, 1H), 7.88 (s, 1H), 7.89 (s, 1H).

Example 25 (Reference Example)

3-(2-Ethyl-4-{5-[2-(isopropyl-methyl-amino)-6-methyl-pyridin-4-yl]-[1,2,4]oxadiazol-3-yl}-6-methyl-phenyl)-propionic acid 3-(2-Ethyl-4-{5-[2-(isopropyl-methyl-amino)-6-methyl-pyridin-4-yl]-[1,2,4]oxadiazol-3-yl}-6-methyl-phenyl)-propionic acid (85 mg) is obtained as a pale yellow solid starting from 2-(isopropyl-methyl-amino)-6-methyl-isonicotinic acid (102 mg, 0.416 mmol) and 3-[2-ethyl-4-(N-hydroxycarbamimidoyl)-6-methyl-phenyl]-propionic acid tert-butyl ester (128 mg, 0.416 mmol) in analogy to Example 8; LC-MS: $t_R$=0.88 min; [M+1]$^+$=423.20; $^1$H NMR (CDCl$_3$): δ 1.15-1.26 (m, 9H), 2.34-2.44 (m, 5H), 2.55 (s, 3H), 2.68-2.77 (m, 2H), 2.90-2.97 (m, 2H), 3.02 (s, 3H), 4.82-4.94 (m, 1H), 7.22 (s, 1H), 7.33 (s, 1H), 7.74 (s, 2H).

Example 26

3-[3-(2-Ethyl-4-{5-[2-(isopropyl-methyl-amino)-6-methyl-pyridin-4-yl]-[1,2,4]oxadiazol-3-yl}-6-methyl-phenyl)-propionylamino]-propionic acid To a solution of 3-(2-ethyl-4-{5-[2-(isopropyl-methyl-amino)-6-methyl-pyridin-4-yl]-[1,2,4]oxadiazol-3-yl}-6-methyl-phenyl)-propionic acid (43 mg, 0.101 mmol) and DIPEA (40 mg, 0.304 mmol) in DMF (3 mL) is added PyBOP (58 mg, 0.111 mmol) at 0° C. The mixture is stirred for 15 min at 0° C. before β-alanine tert.-butyl ester (20 mg, 0.111 mmol) is added and stirring is continued for 1 h at 0° C. The reaction is quenched with 2 mL water, and the mixture is diluted in sat. aq. NaHCO$_3$-solution, and extracted three times with diethyl ether. The combined org. extracts are dried over MgSO$_4$, filtered and dried to give crude 3-[3-(2-ethyl-4-{5-[2-(isopropyl-methyl-amino)-6-methyl-pyridin-4-yl]-[1,2,4]oxadiazol-3-yl}-6-methyl-phenyl)-propionylamino]-propionic acid tert-butyl ester (46 mg). This material is dissolved in 4 N HCl in dioxane (5 mL) and the mixture is stirred at rt for 18 h. The solvent is evaporated and the crude product is purified on prep. TLC plates with DCM containing 18% of 7 N NH$_3$ in methanol to give 3-[3-(2-ethyl-4-{5-[2-(isopropyl-methyl-amino)-6-methyl-pyridin-4-yl]-[1,2,4]oxadiazol-3-yl}-6-methyl-phenyl)-propionylamino]-propionic acid (37 mg) as a yellow solid; LC-MS: $t_R$=0.86 min; [M+1]+=494.24.

Example 27

N-(2-Amino-ethyl)-3-(2-ethyl-4-{5-[2-(isopropyl-methyl-amino)-6-methyl-pyridin-4-yl]-[1,2,4]oxa-diazol-3-yl}-6-methyl-phenyl)-propionamide To a solution of 3-(2-ethyl-4-{5-[2-(isopropyl-methyl-amino)-6-methyl-pyridin-4-yl]-[1,2,4]oxadiazol-3-yl}-6-methyl-phenyl)-propionic acid (41 mg, 0.097 mmol) and DIPEA (38 mg, 0.291 mmol) in DMF (3 mL) is added PyBOP (56 mg, 0.107 mmol) at 0° C. The mixture is stirred for 15 min at 0° C. before N-BOC-ethylenediamine (17 mg, 0.107 mmol) is added and stirring is continued for 1 h at 0° C. The reaction is quenched with 2 mL water, and the mixture is diluted in sat. aq. NaHCO$_3$-solution, and extracted three times with diethyl ether. The combined org. extracts are dried over MgSO$_4$, filtered and dried to give crude {2-[3-(2-ethyl-4-{5-[2-(isopropyl-methyl-amino)-6-methyl-pyridin-4-yl]-[1,2,4]oxadiazol-3-yl}-6-methyl-phenyl)-propionylamino]-ethyl}-carbamic acid tert-butyl ester (44 mg). This material is dissolved in 4 N HCl in dioxane (5 mL) and the mixture is stirred at rt for 18 h. The solvent is evaporated and the crude product is purified on prep. TLC plates with DCM containing 6% of 7 N NH$_3$ in methanol to give N-(2-amino-ethyl)-3-(2-ethyl-4-{5-[2-(isopropyl-methyl-amino)-6-methyl-pyridin-4-yl]-[1,2,4]oxadiazol-3-yl}-6-methyl-phenyl)-propionamide (23 mg) as a yellow solid; LC-MS: $t_R$=0.72 min; [M+1]$^+$=465.32.

Example 28 rac-3-(2-Ethyl-4-{5-[2-ethyl-6-(isopropyl-methyl-amino)-pyridin-4-yl]-[1,2,4]oxadiazol-3-yl}-6-methyl-phenoxy)-propane-1,2-diol rac-3-(2-Ethyl-4-{5-[2-ethyl-6-(isopropyl-methyl-amino)-pyridin-4-yl]-[1,2,4]oxadiazol-3-yl}-6-methyl-phenoxy)-propane-1,2-diol is prepared in analogy to Example 1 starting from 2-ethyl-6-(isopropyl-methyl-amino)-isonicotinic acid and 4-allyloxy-3-ethyl-N-hydroxy-5-methyl-benzamidine; LC-MS: $t_R$=0.85 min; [M+1]$^+$=455.25.

Example 29 rac-3-{2,6-Dimethyl-4-[5-(2-methyl-6-pyrrolidin-1-yl-pyridin-4-yl)-[1,2,4]oxadiazol-3-yl]-phenoxy}-propane-1,2-diol rac-3-{2,6-Dimethyl-4-[5-(2-methyl-6-pyrrolidin-1-yl-pyridin-4-yl)-[1,2,4]oxadiazol-3-yl]-phenoxy}-propane-1,2-diol is prepared in analogy to Example 1 starting from 2-methyl-6-pyrrolidin-1-yl-isonicotinic acid and 4-allyloxy-N-hydroxy-3,5-dimethyl-benzamidine; LC-MS: $t_R$=0.74 min; [M+1]$^+$=425.25; $^1$H NMR δ 1.92-2.02 (m, 4H), 2.35 (s, 6H), 2.43 (s, 3H), 3.42-3.54 (m, 6H), 3.71-3.79 (m, 1H), 3.79-3.90 (m, 2H), 4.64 (t, J=5.5 Hz, 1H), 4.96 (d, J=5.0 Hz, 1H), 6.86 (s, 1H), 7.08 (s, 1H), 7.77 (s, 2H).

Example 30 rac-3-{2-Ethyl-6-methyl-4-[5-(2-methyl-6-pyrrolidin-1-yl-pyridin-4-yl)-[1,2,4]oxadiazol-3-yl]-phenoxy}-propane-1,2-diol rac-3-{2-Ethyl-6-methyl-4-[5-(2-methyl-6-pyrrolidin-1-yl-pyridin-4-yl)-[1,2,4]oxadiazol-3-yl]-phenoxy}-propane-1,2-diol is prepared in analogy to Example 1 starting from 2-methyl-6-pyrrolidin-1-yl-isonicotinic acid and 4-allyloxy-3-ethyl-N-hydroxy-5-methyl-benzamidine; LC-MS: $t_R$=0.77 min; [M+1]⁺=439.24; ¹H NMR (D₆-DMSO): δ 1.22 (t, J=7.5 Hz, 3H), 1.94-2.02 (tm, 4H), 2.36 (s, 3H), 2.43 (s, 3H), 2.75 (q, J=7.5 Hz, 2H), 3.43-3.53 (m, 6H), 3.71-3.79 (m, 1H), 3.80-3.89 (m, 2H), 4.64 (t, J=5.5 Hz, 1H), 4.97 (d, J=5.0 Hz, 1H), 6.86 (s, 1H), 7.08 (s, 1H), 7.78 (s, 2H).

Example 31 rac-3-{4-[5-(2-Dimethylamino-6-ethyl-pyridin-4-yl)-[1,2,4]oxadiazol-3-yl]-2-ethyl-6-methyl-phenoxy}-propane-1,2-diol rac-3-{4-[5-(2-Dimethylamino-6-ethyl-pyridin-4-yl)-[1,2,4]oxadiazol-3-yl]-2-ethyl-6-methyl-phenoxy}-propane-1,2-diol is prepared in analogy to Example 1 starting from 2-dimethylamino-6-ethyl-isonicotinic acid and 4-allyloxy-3-ethyl-N-hydroxy-5-methyl-benzamidine; LC-MS: $t_R$=0.79 min; [M+1]⁺=427.16.

Example 32 rac-N-(3-{4-[5-(2-Dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide To a solution of rac-3-{4-[5-(2-dimethylamino-6-ethyl-pyridin-4-yl)-[1,2,4]oxadiazol-3-yl]-2-ethyl-6-methyl-phenoxy}-propane-1,2-diol (78 mg, 0.183 mmol) and DIPEA (47 mg, 0.365 mmol) in THF (5 mL) is added methanesulfonylchloride (23 mg, 0.201 mmol) at 0° C. The mixture is stirred at 0° C. for 3 h (Mesylate: LC-MS: $t_R$=0.88 min; [M+1]⁺=505.12) before it is added to 7 N NH₃ in methanol (10 mL). The mixture is stirred at 65° C. for 16 h. The solvent is removed in vacuo and the crude product is purified on prep. TLC plates with DCM containing 5% of methanol and 10% of 7 N NH₃ in methanol to give rac-1-amino-3-{4-[5-(2-dimethylamino-6-ethyl-pyridin-4-yl)-[1,2,4]oxadiazol-3-yl]-2-ethyl-6-methyl-phen-oxy}-propan-2-ol as a yellow resin. This material is dissolved in DCM and to the solution glycolic acid (29 mg, 0.375 mmol) and DIPEA (70 mg, 0.540 mmol) is added. The mixture is cooled to 0° C. before TBTU (71 mg, 0.221 mmol) is added. The mixture is stirred at 0° C. for 1 h before it is diluted with EA (100 mL), washed twice with sat. aq. NaHCO₃-solution (25 mL), dried over Na₂SO₄, filtered and concentrated. The crude product is purified on prep. TLC plates with heptane:EA 7:3 to give rac-N-(3-{4-[5-(2-dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide (32 mg) as a yellow resin; LC-MS: $t_R$=0.76 min; [M+1]⁺=484.19.

Example 33 rac-3-{4-[5-(2-Dimethylamino-6-isobutyl-pyridin-4-yl)-[1,2,4]oxadiazol-3-yl]-2-ethyl-6-methyl-phenoxy}-propane-1,2-diol rac-3-{4-[5-(2-Dimethylamino-6-isobutyl-pyridin-4-yl)-[1,2,4]oxadiazol-3-yl]-2-ethyl-6-methyl-phenoxy}-propane-1,2-diol is prepared in analogy to Example 1 from 2-dimethylamino-6-isobutyl-isonicotinic acid and 4-allyloxy-3-ethyl-N-hydroxy-5-methyl-benzamidine; LC-MS: $t_R$=0.86 min; [M+1]⁺=455.22.

Example 34 rac-3-(2-Ethyl-4-{5-[2-(isobutyl-methyl-amino)-6-methyl-pyridin-4-yl]-[1,2,4]oxadiazol-3-yl}-6-methyl-phenoxy)-propane-1,2-diol rac-3-(2-Ethyl-4-{5-[2-(isobutyl-methyl-amino)-6-methyl-pyridin-4-yl]-[1,2,4]oxadiazol-3-yl}-6-methyl-phenoxy)-propane-1,2-diol is prepared in analogy to Example 1 from 2-(isobutyl-methyl-amino)-6-methyl-isonicotinic acid and 4-allyloxy-3-ethyl-N-hydroxy-5-methyl-benzamidine; LC-MS: $t_R$=0.85 min; [M+1]⁺=455.26; ¹H NMR (CDCl₃): δ 0.96 (d, J=6.8 Hz, 6H), 1.32 (t, J=7.5 Hz, 3H), 2.08-2.19 (m, 1H), 2.41 (s, 3H), 2.50 (s, 3H), 2.77 (q, J=7.5 Hz, 2H) 3.17 (s, 3H), 3.45 (d, J=7.3 Hz, 2H), 3.82-3.97 (m, 4H), 4.13-4.20 (m, 1H), 7.02 (s, 1H), 7.12 (s, 1H), 7.87 (s, 1H), 7.88 (s, 1H).

Examples 35 and 36

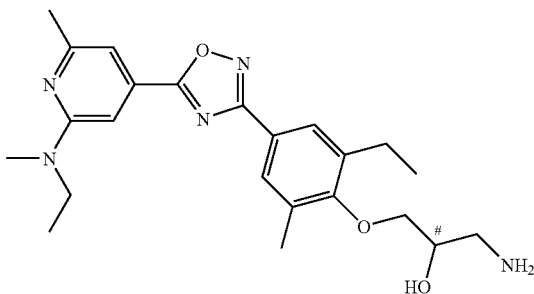 [SMILES: CCc1cc(-c2noc(-c3cc(C)nc(N(C)CC)c3)n2)cc(C)c1OCC(O)CN]

The following Examples are prepared starting from Example 5 in analogy to the procedure given in Example 16.

| Example | # Chirality | LC-MS* $t_R$ (min) | [M + H]⁺ |
|---|---|---|---|
| 35 | R | 1.48 | 425.87 |
| 36 | S | 1.40 | 425.85 |

Examples 37 and 38

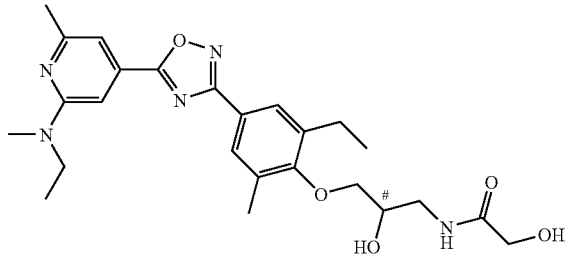 [SMILES: CCc1cc(-c2noc(-c3cc(C)nc(N(C)CC)c3)n2)cc(C)c1OCC(O)CNC(=O)CO]

The following Examples are prepared starting in analogy to the procedure given in Example 17 starting from previous Examples.

| Example | starting from Example | # Chirality | LC-MS* $t_R$ (min) | [M + H]⁺ |
|---|---|---|---|---|
| 37 | 35 | R | 0.95 | 484.11 |
| 38 | 36 | S | 0.95 | 484.07 |

Example 37

¹H NMR (CDCl₃): δ 1.20 (t, J=7.0 Hz, 3H), 1.29 (t, J=7.5 Hz, 3H), 2.35 (s, 3H), 2.48 (s, 3H), 2.71 (q, J=7.3 Hz, 2H), 3.11 (s, 3H), 3.45-3.54 (m, 1H), 3.66 (q, J=7.0 Hz, 2H), 3.71-3.89 (m, 3H), 4.13-4.22 (m, 3H), 6.98 (s, 1H), 7.07 (s, 1H), 7.39 (t, J=5.8 Hz, 1H), 7.80 (s, 1H), 7.83 (s, 1H).

Example 39

2-Ethyl-4-{3-[2-(ethyl-methyl-amino)-6-methyl-pyridin-4-yl]-[1,2,4]oxadiazol-5-yl}-6-methyl-phenol The title compound is obtained as a yellow oil (267 mg) from 3-ethyl-4-hydroxy-5-methyl-benzoic acid (260 mg, 1.44 mmol) and 2-(ethyl-methyl-amino)-N-hydroxy-6-methyl-isonicotinamidine (305 mg, 1.46 mmol) in analogy to the procedure given in Example 5; LC-MS: $t_R$=0.84 min; [M+1]$^+$=353.17.

Examples 40 to 45

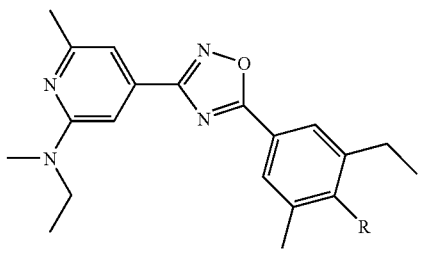

The following Examples are prepared starting from Example 39 in analogy to previous Examples.

Example 41

$^1$H NMR (CDCl$_3$): δ 1.21 (t, J=7.3 Hz, 3H), 1.33 (t, J=7.5 Hz, 3H), 2.42 (s, 3H), 2.50 (s, 3H), 2.78 (q, J=7.5 Hz, 2H), 3.14 (s, 3H), 3.69 (q, J=7.0 Hz, 2H), 3.81-4.00 (m, 4H), 4.15-4.21 (m, 1H), 7.05 (s, 1H), 7.12 (s, 1H), 7.93 (s, 1H), 7.94 (s, 1H).

Example 46

1-((S)-3-{4-[5-(2-Diethylamino-6-methyl-pyridin-4-yl)-[1,2,4]oxadiazol-3-yl]-2-ethyl-6-methyl-phenoxy}-2-hydroxy-propyl)-azetidine-3-carboxylic acid methyl ester A solution of azetidine-3-carboxylic acid methyl ester (40 mg, 0.355 mmol) and diethyl-{4-[3-((S)-3-ethyl-5-methyl-4-oxiranylmethoxy-phenyl)-[1,2,4]oxadiazol-5-yl]-6-methyl-pyridin-2-yl}-amine (300 mg, 0.71 mmol, Example 18 step a)) in methanol (5 mL) and triethylamine (0.1 mL) is stirred at 60° C. for 2 days. The mixture is dissolved with EA and washed with sat. aq. NaHCO$_3$-solution. The org. extract is collected and concentrated. The crude product is purified by prep. HPLC to give the title compound (60 mg) as pale yellow oil; LC-MS: $t_R$=0.79 min; [M+1]$^+$=538.04; $^1$H NMR (CDCl$_3$): δ 1.25 (t, J=6.8 Hz, 6H), 1.32 (t, J=7.5 Hz, 3H), 2.40 (s, 3H), 2.50 (s, 3H), 2.71-2.80 (m, 4H), 3.06 (s br, 1H), 3.35-3.46 (m, 2H), 3.48-3.54 (m, 2H), 3.58-3.72 (m, 6H), 3.75 (s, 3H), 3.81-3.86 (m, 2H), 3.93-4.00 (m, 1H), 7.01 (s, 1H), 7.10 (s, 1H), 7.87 (s, 1H), 7.88 (s, 1H).

| | prepared in analogy | | LC-MS | |
|---|---|---|---|---|
| Example | to Example | R | $t_R$ (min) | [M + H]$^+$ |
| 40 | 3 | ![structure] | 0.76 | 427.15 |
| 41 | 4 | ![structure] | 0.76 | 427.13 |
| 42 | 16 | ![structure] | 0.67 | 426.21 |
| 43 | 16 | ![structure] | 0.66 | 426.19 |
| 44 | 17 | ![structure] | 0.74 | 484.30 |
| 45 | 17 | ![structure] | 0.73 | 484.30 |

Example 47

1-((S)-3-{4-[5-(2-Diethylamino-6-methyl-pyridin-4-yl)-[1,2,4]oxadiazol-3-yl]-2-ethyl-6-methyl-phenoxy}-2-hydroxy-propyl)-azetidine-3-carboxylic acid A solution of 1-((S)-3-{4-[5-(2-diethylamino-6-methyl-pyridin-4-yl)-[1,2,4]oxadiazol-3-yl]-2-ethyl-6-methyl-phenoxy}-2-hydroxy-propyl)-azetidine-3-carboxylic acid methyl ester (60 mg, 0.113 mmol) in methanol (2 mL), THF (2 mL) and 2 M aq. LiOH solution (1 mL) is stirred at rt for 2 h before the reaction mixture is neutralized by adding formic acid. The mixture is concentrated and the crude product is purified by prep. HPLC followed by precipitation of the product from EA/heptane to give the title compound (7 mg) as a pale yellow solid; LC-MS: $t_R$=0.72 min; $[M+1]^+$=524.24.

Example 48

(S)-1-((S)-3-{4-[5-(2-Diethylamino-6-methyl-pyridin-4-yl)-[1,2,4]oxadiazol-3-yl]-2-ethyl-6-methyl-phenoxy}-2-hydroxy-propyl)-pyrrolidine-2-carboxylic acid methyl ester The title compound is prepared in analogy to Example 46 using (S)-pyrrolidine-2-carboxylic acid methyl ester; LC-MS: $t_R$=0.78 min; $[M+1]^+$=552.38.

Example 49

(S)-1-((S)-3-{4-[5-(2-Diethylamino-6-methyl-pyridin-4-yl)-[1,2,4]oxadiazol-3-yl]-2-ethyl-6-methyl-phenoxy}-2-hydroxy-propyl)-pyrrolidine-2-carboxylic acid The title compound is prepared in analogy to Example 47 from Example 48; LC-MS: $t_R$=0.73 min; $[M+1]^+$=538.32.

Example 50

1-((S)-3-{4-[5-(2-Diethylamino-6-methyl-pyridin-4-yl)-[1,2,4]oxadiazol-3-yl]-2-ethyl-6-methyl-phenoxy}-2-hydroxy-propyl)-pyrrolidine-3-carboxylic acid methyl ester The title compound is prepared in analogy to Example 46 using pyrrolidine-3-carboxylic acid methyl ester; LC-MS: $t_R$=0.76 min; $[M+1]^+$=552.28.

Example 51

1-((S)-3-{4-[5-(2-Diethylamino-6-methyl-pyridin-4-yl)-[1,2,4]oxadiazol-3-yl]-2-ethyl-6-methyl-phenoxy}-2-hydroxy-propyl)-pyrrolidine-3-carboxylic acid The title compound is prepared in analogy to Example 47 from Example 50; LC-MS: $t_R$=0.72 min; $[M+1]^+$=538.21.

Example 52

2-{4-[5-(2-Diethylamino-6-methyl-pyridin-4-yl)-[1,2,4]oxadiazol-3-yl]-2-ethyl-6-methyl-phenoxy}-propane-1,3-diol 4-[5-(2-Diethylamino-6-methyl-pyridin-4-yl)-[1,2,4]oxadiazol-3-yl]-2-ethyl-6-methyl-phenol (100 mg, 0.273 mmol, Example 12) is reacted with 2,2-dimethyl-[1,3]dioxan-5-ol (54 mg, 0.409 mmol) under Mitsunobu conditions as described in Example 18, step a) to give (4-{3-[4-(2,2-dimethyl-[1,3]dioxan-5-yloxy)-3-ethyl-5-methyl-phenyl]-[1,2,4]oxadiazol-5-yl}-6-methyl-pyridin-2-yl)-diethyl-amine (65 mg) as yellow oil; LC-MS: $t_R$=0.97 min; $[M+1]^+$=481.27. This material (65 mg, 0.135 mmol) is dissolved in 25% aq. HCl (3 mL) and the resulting mixture is stirred at rt for 2 h. The solvent is evaporated and the crude product is purified by prep. HPLC to give the title compound (23 mg) as yellow solid; LC-MS: $t_R$=0.80 min; $[M+1]^+$=441.24; $^1$H NMR (CD$_3$OD): δ 1.22 (t, J=7.0 Hz, 6H), 1.28 (t, J=7.5 Hz, 3H), 2.41 (s, 3H), 2.44 (s, 3H), 2.82 (q, J=7.5 Hz, 2H), 3.61 (q, J=7.0 Hz, 4H), 3.78 (dd, J=11.3, 4.8 Hz, 2H), 3.84 (dd, J=11.5, 5.0 Hz, 2H), 4.11-4.18 (m, 1H), 7.02 (s, 2H), 7.77 (s, 1H), 7.82 (s, 1H).

Example 53

2-{4-[5-(2-Diethylamino-6-methyl-pyridin-4-yl)-[1,2,4]oxadiazol-3-yl]-2-ethyl-6-methyl-phenoxymethyl}-propane-1,3-diol The title compound is prepared in analogy to Example 52 using (2,2-dimethyl-[1,3]dioxan-5-yl-methanol; LC-MS: $t_R$=0.81 min; $[M+1]^+$=455.28; $^1$H NMR (CDCl$_3$): δ 1.25 (t, J=7.0 Hz, 6H), 1.33 (t, J=7.5 Hz, 3H), 2.15 (s br, 1H), 2.28-2.35 (m, 1H), 2.41 (s, 3H), 2.51 (s, 3H), 2.77 (q, J=7.5 Hz, 2H), 3.26 (t br, J=4.3 Hz, 1H), 3.64 (q, J=6.8 Hz, 4H), 4.00 (d, J=5.5 Hz, 2H), 4.05 (d, J=5.5 Hz, 4H), 7.02 (s, 1H), 7.11 (s, 1H), 7.88 (s, 1H), 7.89 (s, 1H).

Example 54

2-{4-[5-(2-Diethylamino-6-methyl-pyridin-4-yl)-[1,2,4]oxadiazol-3-yl]-2-ethyl-6-methyl-phenoxy}-ethanol The title compound is prepared by alkylating the compound of Example 12 with 2-bromoethanol in analogy to Example 3; LC-MS: $t_R$=0.90 min; $[M+1]^+$=411.01; $^1$H NMR (CDCl$_3$): δ 1.25 (t, J=6.8 Hz, 6H), 1.33 (t, J=7.5 Hz, 3H), 2.42 (s, 3H), 2.50 (s, 3H), 2.79 (q, J=7.3 Hz, 2H), 3.63 (q, J=7.0 Hz, 4H), 3.97-4.05 (m, 4H), 7.01 (s, 1H), 7.11 (s, 1H), 7.88 (s, 1H), 7.89 (s, 1H).

Example 55

(4-{3-[4-(2-Amino-ethoxy)-3-ethyl-5-methyl-phenyl]-[1,2,4]oxadiazol-5-yl}-6-methyl-pyridin-2-yl)-diethyl-amine a) To a solution of 2-{4-[5-(2-diethylamino-6-methyl-pyridin-4-yl)-[1,2,4]oxadiazol-3-yl]-2-ethyl-6-methyl-phenoxy}-ethanol (850 mg, 2.07 mmol) and DIPEA (401 mg, 3.11 mmol) in DCM (20 mL), methane sulfonylchloride (285 mg, 2.49 mmol) is slowly added. The mixture is stirred at rt for 30 min before it is diluted with EA and washed with sat. aq. NaHCO$_3$-solution. The washing is extracted back three times with EA. The combined org. extracts are dried over MgSO$_4$, filtered, concentrated and dried to give crude methanesulfonic acid 2-{4-[5-(2-diethylamino-6-methyl-pyridin-4-yl)-[1,2,4]oxadiazol-3-yl]-2-ethyl-6-methyl-phenoxy}-ethyl ester (925 mg) as a yellow solid; LC-MS: $t_R$=0.94 min; $[M+1]^+$=489.18.

b) To a solution of the above methane sulfonic acid ester (300 mg, 0.614 mmol) in DMF (5 mL), NaN$_3$ (200 mg, 3.07 mmol) is added. The mixture is stirred at rt for 2 days before it is diluted with EA and washed with water followed by brine. The combined washings are extracted back three times with EA, the combined org. extracts are dried over MgSO$_4$, filtered, concentrated and dried to give crude (4-{3-[4-(2-azido-ethoxy)-3-ethyl-5-methyl-phenyl]-[1,2,4]oxadiazol-5-yl}-6-methyl-pyridin-2-yl)-diethyl-amine (285 mg) as a yellow solid; LC-MS: $t_R$=1.00 min; [M+1]$^+$=436.19.

c) To a solution of the above azide (285 mg, 0.654 mmol) in THF (15 mL), triphenylphosphine (251 mg, 0.982 mmol) is added. The mixture is stirred at rt for 1 day before the solvent is evaporated under reduced pressure to give the crude title compound. A portion (30 mg) is purified by prep. HPLC to give the pure title compound as a pale yellow oil; LC-MS: $t_R$=0.70 min; [M+1]$^+$=410.13; $^1$H NMR (CDCl$_3$): δ 1.24 (t, J=7.0 Hz, 6H), 1.32 (t, J=7.3 Hz, 3H), 2.39 (s, 3H), 2.49 (s, 3H), 2.75 (q, J=7.0 Hz, 2H), 3.31-3.42 (m, 2H), 3.62 (q, J=7.0 Hz, 4H), 4.02-4.09 (m, 2H), 4.77 (s br, 2H), 6.99 (s, 1H), 7.07 (s, 1H), 7.85 (s, 1H), 7.87 (s, 1H).

Example 56

N-(2-{4-[5-(2-Diethylamino-6-methyl-pyridin-4-yl)-[1,2,4]oxadiazol-3-yl]-2-ethyl-6-methyl-phenoxy}-ethyl)-2-hydroxy-acetamide The title compound is prepared from Example 55 in analogy to Example 17; LC-MS: $t_R$=0.82 min; [M+1]$^+$=468.23; $^1$H NMR (CDCl$_3$): δ 1.25 (t, J=6.8 Hz, 6H), 1.32 (t, J=7.5 Hz, 3H), 2.38 (s, 3H), 2.49 (s, 3H), 2.74 (q, J=7.5 Hz, 2H), 3.63 (q, J=7.0 Hz, 4H), 3.79 (q, J=5.3 Hz, 2H), 3.96 (t, J=4.8 Hz, 2H), 4.22 (s, 2H), 7.00 (s, 1H), 7.10 (s, 1H), 7.87 (s, 1H), 7.88 (s, 1H).

Example 57

2-Amino-N-(2-{4-[5-(2-diethylamino-6-methyl-pyridin-4-yl)-[1,2,4]oxadiazol-3-yl]-2-ethyl-6-methyl-phenoxy}-ethyl)-acetamide a) [(2-{4-[5-(2-Diethylamino-6-methyl-pyridin-4-yl)-[1,2,4]oxadiazol-3-yl]-2-ethyl-6-methyl-phenoxy}-ethylcarbamoyl)-methyl]-carbamic acid tert-butyl ester (110 mg) is obtained as a yellow oil starting from Example 55 (140 mg, 0.342 mmol) and tert-butoxycarbonyl glycine (120 mg, 0.684 mmol) following the procedure given in Example 17; LC-MS: $t_R$=0.92 min; [M+1]$^+$=567.31.

b) To a solution of [(2-{4-[5-(2-diethylamino-6-methyl-pyridin-4-yl)-[1,2,4]oxadiazol-3-yl]-2-ethyl-6-methyl-phenoxy}-ethylcarbamoyl)-methyl]-carbamic acid tert-butyl ester (65 mg, 0.115 mmol) in DCM (30 mL), trifluoroacetic acid (262 mg, 2.29 mmol) is added. The mixture is stirred at rt for 16 h before it is diluted with EA and washed with sat. aq. NaHCO$_3$-solution and brine. The org. extract is dried over Na$_2$SO$_4$, filtered and concentrated. The crude product is purified on prep. TLC plates using DCM containing 10% of 7 N NH$_3$ in methanol to give the title compound (32 mg) as a yellow resin; LC-MS: $t_R$=0.70 min; [M+1]$^+$=467.19; $^1$H NMR (CDCl$_3$): δ 1.24 (t, J=7.0 Hz, 6H), 1.32 (t, J=7.5 Hz, 3H), 2.01 (s br, 2H), 2.39 (s, 3H), 2.49 (s, 3H), 2.76 (q, J=7.5 Hz, 2H), 3.45 (s, 2H), 3.62 (q, J=7.0 Hz, 4H), 3.73-3.80 (m, 2H), 3.95 (t, J=5.0 Hz, 2H), 7.00 (s, 1H), 7.10 (s, 1H), 7.87 (s, 1H), 7.88 (s, 1H), 7.90 (s br, 1H).

Example 58

N-(2-{4-[5-(2-Diethylamino-6-methyl-pyridin-4-yl)-[1,2,4]oxadiazol-3-yl]-2-ethyl-6-methyl-phenoxy}-ethyl)-2-methylamino-acetamide The title compound is prepared in analogy to Example 57 using BOC-sarcosine; LC-MS: $t_R$=0.72 min; [M+1]$^+$=481.29.

Example 59

N-(2-{4-[5-(2-Diethylamino-6-methyl-pyridin-4-yl)-[1,2,4]oxadiazol-3-yl]-2-ethyl-6-methyl-phenoxy}-ethyl)-methanesulfonamide To a solution of crude (4-{3-[4-(2-amino-ethoxy)-3-ethyl-5-methyl-phenyl]-[1,2,4]oxadiazol-5-yl}-6-methyl-pyridin-2-yl)-diethyl-amine (70 mg, 0.17 mmol) and DIPEA (44 mg, 0.342 mmol) in DCM (2 mL), methane sulfonyl chloride (23 mg, 0.205 mmol) is added. The mixture is stirred at rt for 30 min before it is diluted with EA and washed with sat. aq. NaHCO$_3$-solution. The washing is extracted back three times with EA. The combined org. extracts are dried over MgSO$_4$, filtered and concentrated. The crude product is purified on prep. TLC plates using heptane:EA 1:1 to give the title compound (34 mg) as a pale yellow oil; LC-MS*: $t_R$=1.12 min; [M+1]$^+$=488.05; $^1$H NMR (CDCl$_3$): δ 1.25 (t, J=6.8 Hz, 6H), 1.33 (t, J=7.5 Hz, 3H), 2.40 (s, 3H), 2.50 (s, 3H), 2.76 (q, J=7.5 Hz, 2H), 3.09 (s, 3H), 3.57-3.67 (m, 6H), 3.99 (t, J=4.8 Hz, 2H), 4.91 (t, J=5.5 Hz, 1H), 7.01 (s, 1H), 7.10 (s, 1H), 7.88 (s, 1H), 7.89 (s, 1H).

Example 60

N-(2-{4-[5-(2-Diethylamino-6-methyl-pyridin-4-yl)-[1,2,4]oxadiazol-3-yl]-2-ethyl-6-methyl-phenoxy}-ethyl)-N',N'-dimethyl-sulfamic acid amide The title compound is prepared in analogy to Example 59 using dimethylsulfamoyl chloride; LC-MS*: $t_R$=0.96 min; [M+1]$^+$=517.06.

Example 61

Diethyl-(4-{3-[3-ethyl-5-methyl-4-(2-methylamino-ethoxy)-phenyl]-[1,2,4]oxadiazol-5-yl}-6-methyl-pyridin-2-yl)-amine A solution of crude methanesulfonic acid 2-{4-[5-(2-diethylamino-6-methyl-pyridin-4-yl)-[1,2,4]oxadiazol-3-yl]-2-ethyl-6-methyl-phenoxy}-ethyl ester (110 mg, 0.225 mmol, Example 55 step a)) in 8 M methylamine in methanol (4 mL) is stirred in a sealed glass vial at 70° C. for 15 h. The solvent is evaporated and the crude product is purified on prep. TLC plates using DCM containing 10% of 7 N NH$_3$ in methanol to give the title compound (93 mg) as a pale yellow oil; LC-MS: $t_R$=0.71 min; [M+1]$^+$=424.19.

Example 62

2-(2-{4-[5-(2-Diethylamino-6-methyl-pyridin-4-yl)-[1,2,4]oxadiazol-3-yl]-2-ethyl-6-methyl-phenoxy}-ethylamino)-ethanol The title compound is prepared in analogy to Example 61 using ethanolamine; LC-MS: $t_R$=0.70 min; [M+1]$^+$=454.24.

Example 63

1-(2-{4-[5-(2-Diethylamino-6-methyl-pyridin-4-yl)-[1,2,4]oxadiazol-3-yl]-2-ethyl-6-methyl-phenoxy}-ethyl)-azetidine-3-carboxylic acid methyl ester The title compound is prepared in analogy to Example 61 using azetidine-3-carboxylic acid methyl ester; LC-MS: $t_R$=0.76 min; [M+1]$^+$=508.27; $^1$H NMR (CDCl$_3$): δ 1.24 (t, J=7.0 Hz, 6H), 1.32 (t, J=7.5 Hz, 3H), 2.39 (s, 3H), 2.49 (s, 3H), 2.76 (q, J=7.5 Hz, 2H), 2.92 (t, J=5.5 Hz, 2H), 3.40-3.52 (m, 3H), 3.62 (q, J=7.0 Hz, 4H), 3.70-3.75 (m, 2H), 3.75 (s, 3H), 3.83 (t, J=5.5 Hz, 2H), 7.00 (s, 1H), 7.10 (s, 1H), 7.85 (s, 1H), 7.87 (s, 1H).

Example 64

1-(2-{4-[5-(2-Diethylamino-6-methyl-pyridin-4-yl)-[1,2,4]oxadiazol-3-yl]-2-ethyl-6-methyl-phenoxy}-ethyl)-azetidine-3-carboxylic acid The title compound is prepared from Example 63 in analogy to Example 47; LC-MS: $t_R$=0.73 min; [M+1]$^+$=494.32.

Example 65 rac-1-(2-{4-[5-(2-Diethylamino-6-methyl-pyridin-4-yl)-[1,2,4]oxadiazol-3-yl]-2-ethyl-6-methyl-phenoxy}-ethyl)-pyrrolidine-3-carboxylic acid methyl ester The title compound is prepared in analogy to Example 61 using pyrrolidine-3-carboxylic acid methyl ester; LC-MS: $t_R$=0.78 min; [M+1]$^+$=522.20.

Example 66 rac-1-(2-{4-[5-(2-Diethylamino-6-methyl-pyridin-4-yl)-[1,2,4]oxadiazol-3-yl]-2-ethyl-6-methyl-phenoxy}-ethyl)-pyrrolidine-3-carboxylic acid The title compound is prepared from Example 65 in analogy to Example 47; LC-MS: $t_R$=0.74 min; [M+1]$^+$=508.25.

Example 67 (Reference Example)

3-{4-[5-(2-Diethylamino-6-methyl-pyridin-4-yl)-[1,2,4]oxadiazol-3-yl]-2-ethyl-6-methyl-phenyl}-propionic acid The title compound is prepared in analogy to Example 8 starting from 2-(diethylamino)-6-methyl-isonicotinic acid and 3-[2-ethyl-4-(N-hydroxycarbamimidoyl)-6-methyl-phenyl]-propionic acid tert-butyl ester; LC-MS: $t_R$=0.88 min; [M+1]$^+$=423.17.

Example 68

3-{4-[5-(2-Diethylamino-6-methyl-pyridin-4-yl)-[1,2,4]oxadiazol-3-yl]-2-ethyl-6-methyl-phenyl}-N-(2-hydroxy-ethyl)-propionamide The title compound is prepared by coupling 3-{4-[5-(2-diethylamino-6-methyl-pyridin-4-yl)-[1,2,4]oxadiazol-3-yl]-2-ethyl-6-methyl-phenyl}-propionic acid with ethanolamine as described in Example 26 omitting the treatment with HCl; LC-MS: $t_R$=0.80 min; [M+1]$^+$=466.26.

Examples 69 to 73

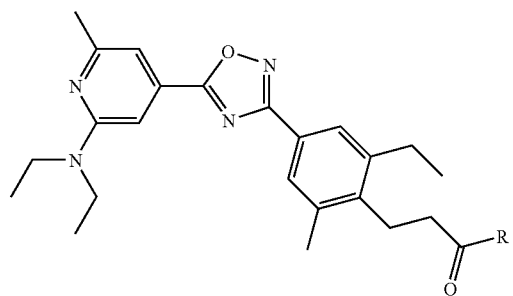

The following Examples are prepared by coupling 3-{4-[5-(2-diethylamino-6-methyl-pyridin-4-yl)-[1,2,4]oxadiazol-3-yl]-2-ethyl-6-methyl-phenyl}-propionic acid with the appropriate amino acids following the procedure given in Example 26.

| Example | R | LC-MS $t_R$ (min) | [M + H]$^+$ |
|---|---|---|---|
| 69 | HN~~COOH | 0.82 | 480.26 |
| 70 | HN~~~COOH | 0.83 | 494.26 |
| 71 | N(azetidine)-COOH | 0.82 | 506.23 |
| 72 | pyrrolidine-2-COOH | 0.85 | 520.24 |
| 73 | pyrrolidine-3-COOH | 0.84 | 520.26 |

Example 69

$^1$H NMR (CDCl$_3$): δ 1.25 (t, J=7.0 Hz, 6H), 1.32 (t, J=7.5 Hz, 3H), 2.43-2.48 (m, 5H), 2.50 (s, 3H), 2.77 (q, J=7.3 Hz, 2H), 3.07-3.14 (m, 2H), 3.63 (q, J=7.0 Hz, 4H), 4.12-4.17 (m, 2H), 6.04 (s br, 1H), 7.02 (s, 1H), 7.10 (s, 1H), 7.84 (s, 1H), 7.85 (s, 1H).

Example 74

4-[3-(2-Diethylamino-6-methyl-pyridin-4-yl)-[1,2,4]oxadiazol-5-yl]-2-ethyl-6-methyl-phenol The title compound is obtained as a yellow solid (589 mg) from 3-ethyl-4-hydroxy-5-methyl-benzoic acid (504 mg, 2.80 mmol) and 2-(diethylamino)-N-hydroxy-6-methyl-isonicotinamidine (622 mg, 2.80 mmol) in analogy to the procedure given in Example 5; LC-MS: $t_R$=0.89 min; [M+1]$^+$=367.18.

Examples 75 to 80

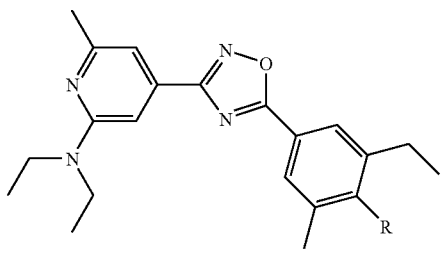

The following Examples are prepared starting from Example 74 in analogy to previous Examples.

| Example | prepared in analogy to Example | R | LC-MS $t_R$ (min) | [M + H]$^+$ |
|---|---|---|---|---|
| 75 | 3 | ![](O^OH with OH, S) | 0.79 | 441.26 |
| 76 | 4 | ![](O^OH with OH, R) | 0.79 | 441.26 |
| 77 | 16 | ![](O^NH2 with OH) | 0.68 | 440.28 |
| 78 | 16 | ![](O^NH2 with OH) | 0.69 | 440.27 |
| 79 | 17 | ![](O^NH-CO-CH2OH with OH) | 0.76 | 498.20 |
| 80 | 17 | ![](O^NH-CO-CH2OH with OH) | 0.77 | 498.21 |

Example 78

$^1$H NMR (CDCl$_3$): δ 1.24 (t, J=7.0 Hz, 6H), 1.33 (t, J=7.5 Hz, 3H), 2.42 (s, 3H), 2.48 (s, 3H), 2.79 (q, J=7.5 Hz, 2H), 2.94 (dd, J=12.5, 7.0 Hz), 3.05 (dd, J=12.8, 4.0 Hz), 3.63 (q, J=7.0 Hz, 4H), 3.89 (d, J=5.0 Hz, 2H), 3.98-4.06 (m, 1H), 7.02 (s, 1H), 7.09 (s, 1H), 7.93 (s, 1H), 7.94 (s, 1H).

Example 81

4-[5-(2-Diethylamino-6-methyl-pyridin-4-yl)-[1,3,4]oxadiazol-2-yl]-2-ethyl-6-methyl-phenol a) To a solution of 2-diethylamino-6-methyl-isonicotinic acid (1.50 g, 6.13 mmol) and DIPEA (2.38 g, 18.4 mmol) in DCM (25 mL), TBTU (2.16 g, 6.74 mmol) is added. The mixture is stirred at rt for 10 min before a solution of 4-benzyloxy-3-ethyl-5-methyl-benzoic acid hydrazide (3.32 g, 6.13 mmol) in DMF (10 mL) is added. The mixture is stirred at rt for 1 h before it is diluted with DCM and washed with sat. aq. NaHCO$_3$-solution. The org. extract is dried over MgSO$_4$, filtered and concentrated. The crude product is purified by CC on silica gel eluting with a gradient of EA in heptane to give 4-benzyloxy-3-ethyl-5-methyl-benzoic acid N'-(2-diethylamino-6-methyl-pyridine-4-carbonyl)-hydrazide (2.1 g) as a gum; LC-MS: $t_R$=0.88 min, [M+1]$^+$=not detectable. This material (2.10 g, 4.42 mmol) is dissolved in THF (40 mL) and Burgess reagent (1.16 g, 4.87 mmol) is added. The mixture is stirred at 110° C. for 5 min under microwave irradiation. The mixture is cooled to rt, diluted with diethyl ether and washed with water. The org. extract is dried over MgSO$_4$, filtered and concentrated. The crude product is purified by CC on silica gel eluting with heptane:EA 4:1 to give {4-[5-(4-benzyloxy-3-ethyl-5-methyl-phenyl)-[1,3,4]oxadiazol-2-yl]-6-methyl-pyridin-2-yl}-diethyl-amine (1.03 g) as a pale yellow gum; LC-MS: $t_R$=0.99 min, [M+1]$^+$=457.27.

b) To a solution of the above material (1.03 g, 2.26 mmol) in THF/ethanol (20 mL), Pd/C (200 mg, 10% Pd) is added as a suspension in ethanol. The mixture is stirred at rt under 1 bar of H$_2$ for 5 h before the catalyst is filtered off and the filtrate is concentrated. The crude product is purified by CC on silica gel eluting with heptane:EA 4:1 to give the title compound (530 mg) as a yellow solid; LC-MS: t$_R$=0.84 min, [M+1]$^+$=367.18.

Examples 82 to 87

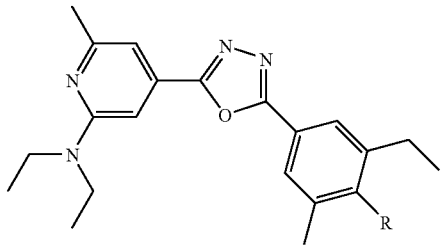

The following Examples are prepared starting from Example 81 in analogy to previous Examples.

|  |  |  | LC-MS | |
|---|---|---|---|---|
| Example | prepared in analogy to Example | R | t$_R$ (min) | [M + H]$^+$ |
| 82 | 3 | O~~~OH / OH | 0.76 | 441.27 |
| 83 | 4 | O~~~OH / OH | 0.76 | 441.27 |
| 84 | 16 | O~~~NH$_2$ / OH | 0.67 | 440.28 |
| 85 | 16 | O~~~NH$_2$ / OH | 0.67 | 440.29 |
| 86 | 17 | O~~~N(H)C(O)CH$_2$OH / OH | 0.74 | 498.29 |
| 87 | 17 | O~~~N(H)C(O)CH$_2$OH / OH | 0.74 | 498.23 |

Example 82

$^1$H NMR (CDCl$_3$): δ 1.25 (t, J=6.8 Hz, 6H), 1.33 (t, J=7.5 Hz, 3H), 2.06 (t br, J=5.3 Hz, 1H), 2.43 (s, 3H), 2.50 (s, 3H), 2.72 (d, J=4.0 Hz, 1H), 2.78 (q, J=7.0 Hz, 2H), 3.63 (q, J=6.5 Hz, 4H), 3.81-4.00 (m, 4H), 4.15-4.22 (m, 1H), 7.00 (s, 2H), 7.84 (s, 1H), 7.87 (s, 1H).

Example 87

$^1$H NMR (CDCl$_3$): δ 1.24 (t, J=7.0 Hz, 6H), 1.33 (t, J=7.3 Hz, 3H), 2.41 (s, 3H), 2.50 (s, 3H), 2.76 (q, J=7.3 Hz, 2H), 3.38 (s br, 1H), 3.50-3.58 (m, 1H), 3.62 (q, J=7.0 Hz, 4H), 3.77-3.94 (m, 3H), 4.18-4.26 (m, 3H), 7.00 (s, 2H), 7.83 (s, 1H), 7.86 (s, 1H).

Example 88

4-[5-(2-Diethylamino-6-methyl-pyridin-4-yl)-[1,3,4] thiadiazol-2-yl]-2-ethyl-6-methyl-phenol a) To a solution of 4-benzyloxy-3-ethyl-5-methyl-benzoic acid N'-(2-diethylamino-6-methyl-pyridine-4-carbonyl)-hydrazide (1.29 g, 2.72 mmol, intermediate from Example 81 step a)) in THF (15 mL), Lawesson reagent (1.21 g, 2.99 mmol) is added. The mixture is stirred at 110° C. for 15 min under microwave irradiation (300 W, external cooling). The mixture is cooled to rt, diluted with EA (100 mL) and washed with sat. aq. Na$_2$CO$_3$-solution (3×50 mL) followed by brine (1×50 mL). The org. extract is dried over MgSO$_4$, filtered, concentrated and dried to give crude {4-[5-(4-benzyloxy-3-ethyl-5-methyl-phenyl)-[1,3,4]thiadiazol-2-yl]-6-methyl-pyridin-2-yl}-diethyl-amine (2.43 g) as a yellow oil; LC-MS: t$_R$=1.01 min, [M+1]$^+$=473.20.

b) A solution of the above crude material (2.43 g, 2.72 mmol) in EA (15 mL) and 33% HBr in acetic acid (6 mL) is stirred at rt for 16 h. The suspension is diluted with EA (20 mL) and 33% HBr in acetic acid (6 mL) and stirring is continued at rt for 24 h, then at 45° C. for 16 h followed by 60° C. for further 16 h. The mixture is diluted with EA (250 mL) and washed with sat. aq. Na$_2$CO$_3$-solution. The org. extract is dried over MgSO₄, filtered and concentrated. The crude product is purified by prep. MPLC on silica gel eluting with a gradient of EA in heptane to give the title compound (827 mg) as a yellow solid; LC-MS: $t_R$=0.90 min, [M+1]⁺=383.00.

Examples 89 to 94

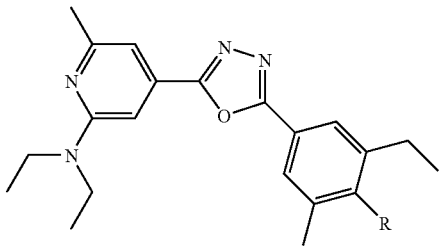

The following Examples are prepared starting from Example 88 in analogy to previous Examples.

Example 95

(S)-1-{4-[5-(2-Diethylamino-6-methyl-pyridin-4-yl)-[1,2,4]oxadiazol-3-yl]-2-ethyl-6-methyl-phenoxy}-3-methoxy-propan-2-ol A solution of diethyl-{4-[3-((S)-3-ethyl-5-methyl-4-oxiranylmethoxy-phenyl)-[1,2,4]oxadiazol-5-yl]-6-methyl-pyridin-2-yl}-amine (100 mg, 0.229 mmol) in 5.4 M NaOMe in methanol (5 mL) is stirred at 70° C. for 72 h. The mixture is diluted with EA and washed with water and brine. The org. extract is dried over Na₂SO₄, filtered and concentrated. The crude product is purified on prep. TLC plates with heptane: EA 1:1 to give the title compound (91 mg) as a yellow solid; LC-MS*: $t_R$=1.21 min, [M+1]⁺=455.09; ¹H NMR (CDCl₃): δ 1.25 (t, J=7.0 Hz, 6H), 1.33 (t, J=7.5 Hz, 3H), 2.41 (s, 3H), 2.50 (s, 3H), 2.58 (d, J=5.0 Hz, 1H), 2.77 (q, J=7.8 Hz, 2H),

| Example | prepared in analogy to Example | R | LC-MS $t_R$ (min) | [M + H]⁺ |
|---|---|---|---|---|
| 89 | 3 | 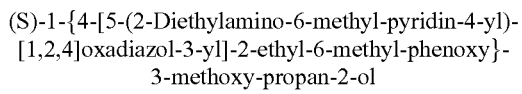 | 0.76 | 457.25 |
| 90 | 4 | ![R group] | 0.76 | 457.25 |
| 91 | 16 | ![R group] | 0.67 | 456.25 |
| 92 | 16 | ![R group] | 0.65 | 456.24 |
| 93 | 17 | ![R group] | 0.74 | 514.20 |
| 94 | 17 | 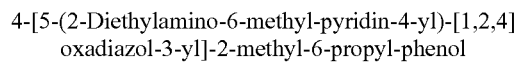 | 0.74 | 514.18 |

Example 89

¹H NMR (CDCl₃): δ 1.24 (t, J=6.8 Hz, 6H), 1.32 (t, J=7.3 Hz, 3H), 2.12 (s br, 1H), 2.40 (s, 3H), 2.47 (s, 3H), 2.76 (q, J=7.0 Hz, 2H), 3.62 (q, J=6.5 Hz, 4H), 3.82-3.98 (m, 4H), 4.14-4.21 (m, 1H), 6.85 (s, 1H), 6.93 (s, 1H), 7.71 (s, 1H), 7.74 (s, 1H).

Example 94

¹H NMR (CDCl₃): δ 1.23 (t, J=6.8 Hz, 6H), 1.30 (t, J=7.5 Hz, 3H), 2.37 (s, 3H), 2.46 (s, 3H), 2.73 (q, J=7.5 Hz, 2H), 3.48-3.57 (m, 1H), 3.61 (q, J=6.8 Hz, 4H), 3.74-3.91 (m, 3H), 4.17-4.24 (m, 3H), 6.83 (s, 1H), 6.90 (s, 1H), 7.15 (s br, 1H), 7.67 (s, 1H), 7.70 (s, 1H).

3.47 (s, 3H), 3.59-3.70 (m, 6H), 3.92 (d, J=5.3 Hz, 2H), 4.19-4.27 (m, 1H), 7.01 (s, 1H), 7.10 (s, 1H), 7.87 (s, 1H), 7.88 (s, 1H).

Example 96

4-[5-(2-Diethylamino-6-methyl-pyridin-4-yl)-[1,2,4]oxadiazol-3-yl]-2-methyl-6-propyl-phenol The title compound is obtained as a yellow solid (775 mg) from 4,N-dihydroxy-3-methyl-5-propyl-benzamidine (1.02 g, 4.90 mmol) and 2-(diethylamino)-6-methyl-isonicotinic acid (1.00 g, 4.09 mmol) in analogy to the procedure given in Example 5; LC-MS*: $t_R$=1.23 min; [M+1]⁺=381.43; ¹H NMR (CDCl₃): δ 1.04 (t, J=7.0 Hz, 3H), 1.25 (t, J=7.0 Hz, 6H), 1.74 (h, J=7.0 Hz, 2H), 2.36 (s, 3H), 2.50 (s, 3H), 2.68 (t, J=7.3 Hz, 2H), 3.63 (q, J=6.8 Hz, 4H), 4.97 (s, 1H), 7.01 (s, 1H), 7.10 (s, 1H), 7.83 (s, 1H), 7.84 (s, 1H).

Examples 97 to 102

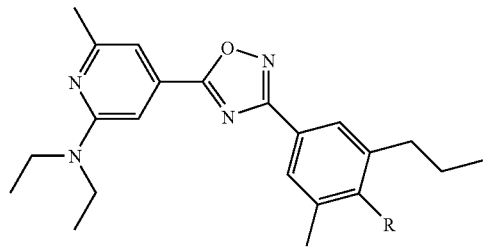

The following Examples are prepared starting from Example 96 in analogy to previous Examples.

Example 101

$^1$H NMR (CDCl$_3$): δ 1.02 (t, J=7.3 Hz, 3H), 1.24 (t, J=7.0 Hz, 6H), 1.68-1.78 (m, 2H), 2.39 (s, 3H), 2.49 (s, 3H), 2.69 (t, J=7.3 Hz, 2H), 3.47-3.57 (m, 4H), 3.62 (q, J=6.8 Hz, 4H), 3.76-3.93 (m, 3H), 4.17-4.24 (m, 3H), 7.00 (s, 1H), 7.06 (t br, J=5.0 Hz), 7.09 (s, 1H), 7.86 (s, 2H).

Example 103

2-Chloro-4-[5-(2-diethylamino-6-methyl-pyridin-4-yl)-[1,2,4]oxadiazol-3-yl]-6-methyl-phenol The title compound is obtained as a yellow solid (991 mg) from 3-chloro-4,N-dihydroxy-5-methyl-benzamidine (0.82 g, 4.09 mmol) and 2-(diethylamino)-6-methyl-isonicotinic acid (1.00 g, 4.09 mmol) in analogy to the procedure given in Example 5; LC-MS: t$_R$=0.88 min; [M+1]$^+$=373.13; $^1$H NMR (D$_6$-DMSO): δ 1.16 (t, J=6.5 Hz, 6H), 2.32 (s, 3H), 2.42 (s, 3H), 3.58 (q, J=6.8 Hz, 4H), 6.98 (s, 1H), 7.05 (s, 1H), 7.81 (s, 1H), 7.88 (s, 1H), 9.97 (s br, 1H).

| Example | prepared in analogy to Example | R | LC-MS t$_R$ (min) | [M + H]$^+$ |
|---|---|---|---|---|
| 97 | 3 | ![](O\~\~OH, OH) | 1.12* | 455.52 |
| 98 | 4 | ![](O\~\~OH, OH) | 1.12* | 455.41 |
| 99 | 16 | ![](O\~\~NH$_2$, OH) | 0.73 | 454.26 |
| 100 | 16 | ![](O\~\~NH$_2$, OH) | 0.73 | 454.23 |
| 101 | 17 | CH$_2$OH, OH) | 1.04* | 512.53 |
| 102 | 17 | CH$_2$OH, OH) | 1.04* | 512.50 |

Examples 104 to 109

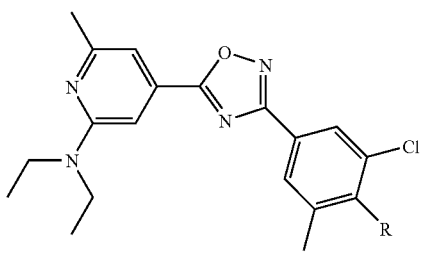

The following Examples are prepared starting from Example 103 in analogy to previous Examples.

| Example | prepared in analogy to Example | R | LC-MS $t_R$ (min) | $[M + H]^+$ |
|---|---|---|---|---|
| 104 | 3 | ![structure] O-CH2-CH(OH)-CH2OH (S) | 1.08* | 447.08 |
| 105 | 4 | O-CH2-CH(OH)-CH2OH (R) | 1.08* | 447.12 |
| 106 | 16 | O-CH2-CH(OH)-CH2NH2 (S) | 1.07* | 446.07 |
| 107 | 16 | O-CH2-CH(OH)-CH2NH2 (R) | 0.70 | 446.22 |
| 108 | 17 | O-CH2-CH(OH)-CH2-NH-C(O)-CH2OH (S) | 1.01* | 504.06 |
| 109 | 17 | O-CH2-CH(OH)-CH2-NH-C(O)-CH2OH (R) | 1.01* | 504.09 |

Example 105

$^1$H NMR (CDCl$_3$): δ 1.25 (t, J=7.0 Hz, 6H), 2.44 (s, 3H), 2.50 (s, 3H), 3.63 (q, J=7.0 Hz, 4H), 3.83-3.94 (m, 2H), 4.09-4.14 (m, 2H), 4.15-4.22 (m, 1H), 6.99 (s, 1H), 7.08 (s, 1H), 7.94 (s, 1H), 8.08 (s, 1H).

Example 109

$^1$H NMR (CDCl$_3$): δ 1.24 (t, J=7.0 Hz, 6H), 2.42 (s, 3H), 2.48 (s, 3H), 3.17 (s br, 1H), 3.52-3.58 (m, 1H), 3.62 (q, J=7.0 Hz, 4H), 3.72 (s br, 1H), 3.77-3.85 (m, 1H), 3.97-4.03 (m, 1H), 4.03-4.08 (m, 1H), 4.17-4.26 (m, 3H), 6.97 (s, 1H), 7.05 (s, 1H), 7.15 (t br, J=5.5 Hz, 1H), 7.91 (s, 1H), 8.05 (s, 1H).

Example 110

{4-[3-(4-Amino-3-chloro-5-methyl-phenyl)-[1,2,4] oxadiazol-5-yl]-6-methyl-pyridin-2-yl}-diethyl-amine The title compound is obtained as a yellow solid (1.72 g) from 4-amino-3-chloro-N-hydroxy-5-methyl-benzamidine (1.21 g, 6.06 mmol) and 2-(diethylamino)-6-methyl-isonicotinic acid (1.52 g, 5.77 mmol) in analogy to the procedure given in Example 5; LC-MS: $t_R$=0.90 min; [M+1]$^+$=372.09; $^1$H NMR (CDCl$_3$): δ 1.25 (t, J=6.8 Hz, 6H), 2.31 (s, 3H), 2.49 (s, 3H), 3.63 (q, J=7.0 Hz, 4H), 4.37 (s, 2H), 7.00 (s, 1H), 7.09 (s, 1H), 7.81 (s, 1H), 8.01 (s, 1H).

Example 111

2-Chloro-4-[5-(2-diethylamino-6-methyl-pyridin-4-yl)-[1,2,4]oxadiazol-3-yl]-6-methoxy-phenol The title compound is obtained as a yellow solid (675 g) from 3-chloro-4,N-dihydroxy-5-methoxy-benzamidine (785 mg, 3.62 mmol) and 2-(diethylamino)-6-methyl-isonicotinic acid (900 mg, 3.43 mmol) in analogy to the procedure given in Example 5; LC-MS: $t_R$=0.86 min; [M+1]$^+$=389.06; $^1$H NMR (CDCl$_3$): δ 1.25 (t, J=6.8 Hz, 6H), 2.50 (s, 3H), 3.63 (q, J=7.0 Hz, 4H), 4.06 (s, 3H), 6.17 (s br, 1H), 7.00 (s, 1H), 7.09 (s, 1H), 7.60 (s, 1H), 7.89 (s, 1H).

Examples 112 to 117

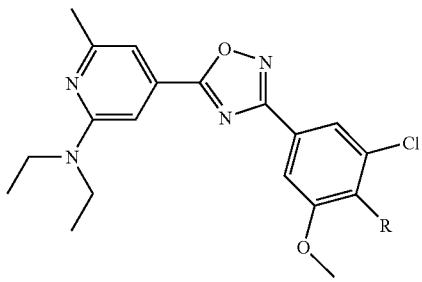

The following Examples are prepared starting from Example 111 in analogy to previous Examples.

Example 118 rac-3-{2,6-Dichloro-4-[5-(2-diethylamino-6-methyl-pyridin-4-yl)-[1,2,4]oxadiazol-3-yl]-phenoxy}-propane-1,2-diol The title compound is prepared in analogy to Example 1 starting from 4-allyloxy-3,5-dichloro-N-hydroxy-benzamidine and 2-(diethylamino)-6-methyl-isonicotinic acid; LC-MS: $t_R$=0.81 min; $[M+1]^+$=467.02; $^1$H NMR (CDCl$_3$): δ 1.25 (t, J=7.0 Hz, 6H), 2.04 (t br, J=6.0 Hz, 1H), 2.50 (s, 3H), 2.88 (d, J=3.8 Hz, 1H), 3.63 (q, J=6.8 Hz, 4H), 3.82-3.96 (m, 2H), 4.17-4.26 (m, 2H), 4.27-4.34 (m, 1H), 6.99 (s, 1H), 7.07 (s, 1H), 8.18 (s, 2H).

| Example | prepared in analogy to Example | R | LC-MS $t_R$ (min) | $[M+H]^+$ |
|---|---|---|---|---|
| 112 | 3 | ![](O~~~OH, OH) | 0.78 | 463.16 |
| 113 | 4 | ![](O~~~OH, OH) | 0.78 | 463.15 |
| 114 | 16 | ![](O~~~NH$_2$, OH) | 0.68 | 462.16 |
| 115 | 16 | ![](O~~~NH$_2$, OH) | 0.68 | 462.16 |
| 116 | 17 | CH$_2$OH, OH) | 0.76 | 520.16 |
| 117 | 17 | CH$_2$OH, OH) | 0.76 | 520.18 |

Example 115

$^1$H NMR (CDCl$_3$): δ 1.25 (t, J=6.5 Hz, 6H), 2.49 (s, 3H), 2.89-3.01 (m, 2H), 3.62 (q, J=6.5 Hz, 4H), 3.94-4.10 (m, 5H), 4.22-4.30 (m, 1H), 6.99 (s, 1H), 7.08 (s, 1H), 7.63 (s, 1H), 7.88 (s, 1H).

Example 116

$^1$H NMR (CDCl$_3$): δ 1.25 (t, J=6.8 Hz, 6H), 2.50 (s, 3H), 2.72 (s br, 1H), 3.46-3.58 (m, 2H), 3.63 (q, J=6.8 Hz, 4H), 3.71-3.80 (m, 2H), 4.02 (s, 3H), 4.14 (s br, 1H), 4.18 (s, 2H), 4.24 (dd, J=9.8, 3.8 Hz, 1H), 6.97-7.03 (m, 2H), 7.08 (s, 1H), 7.64 (s, 1H), 7.88 (s, 1H).

Example 119

4-[5-(2-Diethylamino-6-methyl-pyridin-4-yl)-[1,2,4]oxadiazol-3-yl]-3-methoxy-phenol The title compound is obtained (135 mg) in analogy to Example 5 starting from 4,N-dihydroxy-2-methoxy-benzamidine (123 mg, 0.674 mmol) and 2-(diethylamino)-6-methyl-isonicotinic acid (150 mg, 0.613 mmol); LC-MS: $t_R$=0.75 min; $[M+1]^+$=355.12.

Example 120

(S)-3-{4-[5-(2-Diethylamino-6-methyl-pyridin-4-yl)-[1,2,4]oxadiazol-3-yl]-3-methoxy-phenoxy}-propane-1,2-diol The title compound is prepared from Example 119 in analogy to Example 4; LC-MS: $t_R$=0.71 min; [M+1]$^+$=429.18; $^1$H NMR (CDCl$_3$): δ 1.24 (t, J=7.0 Hz, 6H), 2.49 (s, 3H), 3.62 (q, J=6.8 Hz, 4H), 3.78-3.86 (m, 1H), 3.88-3.94 (m, 1H), 4.00 (s, 3H), 4.14-4.22 (m, 3H), 6.63-6.69 (m, 2H), 7.01 (s, 1H), 7.09 (s, 1H), 8.10 (d, J=8.3 Hz, 1H).

Example 121

{4-[3-(2,4-Dimethoxy-phenyl)-[1,2,4]oxadiazol-5-yl]-6-methyl-pyridin-2-yl}-diethyl-amine The title compound is obtained (125 mg) in analogy to Example 5 starting from N-hydroxy-2,4-dimethoxy-benzamidine (110 mg, 0.562 mmol) and 2-(diethylamino)-6-methyl-isonicotinic acid (125 mg, 0.511 mmol); LC-MS*: $t_R$=1.12 min; [M+1]$^+$=369.09; $^1$H NMR (CDCl$_3$): δ 1.23 (t, J=7.0 Hz, 6H), 2.49 (s, 3H), 3.61 (q, J=6.8 Hz, 4H), 3.90 (s, 3H), 4.00 (s, 3H), 6.62 (s, 1H), 6.65 (d, J=8.5 Hz, 1H), 7.01 (s, 1H), 7.09 (s, 1H), 8.09 (d, J=8.8 Hz, 1H).

Example 122

3-Chloro-4-[5-(2-diethylamino-6-methyl-pyridin-4-yl)-[1,2,4]oxadiazol-3-yl]-phenol The title compound is obtained (122 mg) in analogy to Example 5 starting from 2-chloro-4,N-dihydroxy-benzamidine (800 mg, 4.29 mmol) and 2-(diethylamino)-6-methyl-isonicotinic acid (1.13 g, 4.29 mmol); LC-MS: $t_R$=0.82 min; [M+1]$^+$=359.04.

Example 123

(S)-3-{3-Chloro-4-[5-(2-diethylamino-6-methyl-pyridin-4-yl)-[1,2,4]oxadiazol-3-yl]-phenoxy}-propane-1,2-diol The title compound is prepared from Example 122 in analogy to Example 4; LC-MS: $t_R$=0.75 min; [M+1]$^+$=427.13; $^1$H NMR (CDCl$_3$): δ 1.24 (t, J=7.0 Hz, 6H), 2.03 (s br, 1H), 2.49 (s, 3H), 2.62 (s br, 1H), 3.62 (q, J=7.0 Hz, 4H), 3.77-3.84 (m, 1H), 3.86-3.93 (m, 1H), 4.12-4.22 (m, 3H), 6.96-7.02 (m, 2H), 7.09 (s, 1H), 7.14 (s, 1H), 8.01 (d, J=8.8 Hz, 1H).

Example 124 rac-3-{4-[5-(2-Diethylamino-6-methyl-pyridin-4-yl)-[1,2,4]oxadiazol-3-yl]-3-methyl-phenoxy}-propane-1,2-diol The title compound is prepared in analogy to Example 1 starting from 2-(diethylamino)-6-methyl-isonicotinic acid and 4-allyloxy-N-hydroxy-2-methyl-benzamidine; LC-MS: $t_R$=0.75 min; [M+1]$^+$=413.26; $^1$H NMR (CD$_3$OD): δ 1.24 (t, J=7.0 Hz, 6H), 2.46 (s, 3H), 2.64 (s, 3H), 3.64 (q, J=7.0 Hz, 4H), 3.67-3.77 (m, 2H), 3.99-4.09 (m, 2H), 4.16 (dd, J=9.5, 4.3 Hz, 1H), 6.95-7.00 (m, 2H), 7.06 (d, J=3.3 Hz, 2H), 8.02 (d, J=8.5 Hz, 1H).

Example 125 rac-N-(3-{4-[5-(2-Diethylamino-6-methyl-pyridin-4-yl)-[1,2,4]oxadiazol-3-yl]-3-methyl-phenoxy}-2-hydroxy-propyl)-2-hydroxy-acetamide The title compound is prepared in analogy to Example 32 starting from Example 124; LC-MS: $t_R$=0.73 min; [M+1]$^+$=470.27; $^1$H NMR (CD$_3$OD): δ 1.23 (t, J=7.0 Hz, 6H), 2.45 (s, 3H), 2.64 (s, 3H), 3.44 (dd, J=13.8, 6.5 Hz, 1H), 3.58-3.67 (m, 5H), 4.04 (s, 2H), 4.05-4.15 (m, 3H), 6.94-6.99 (m, 2H), 7.04 (d, J=2.8 Hz, 2H), 8.01 (d, J=8.3 Hz, 1H).

Examples 126 to 130

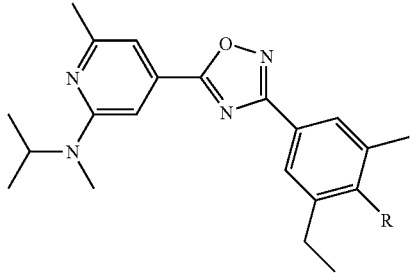

The following Examples are prepared in analogy to previous Examples starting from Example 23.

| Example | prepared in analogy to Example | R | LC-MS $t_R$ (min) | [M + H]$^+$ |
|---|---|---|---|---|
| 126 | 3 | O∼∼OH, OH | 0.81 | 441.27 |
| 127 | 16 | O∼∼NH$_2$, OH | 071 | 440.28 |

-continued

| Example | prepared in analogy to Example | R | LC-MS $t_R$ (min) | $[M + H]^+$ |
|---|---|---|---|---|
| 128 | 16 | 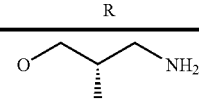 | 0.71 | 440.26 |
| 129 | 17 | 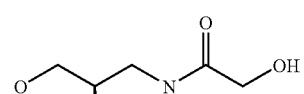 | 0.78 | 498.23 |
| 130 | 17 |  | 0.78 | 498.21 |

Example 127

$^1$H NMR (CDCl$_3$): δ 1.22 (d, J=6.5 Hz, 6H), 1.29 (t, J=7.5 Hz, 3H), 2.35 (s, 2H), 2.48 (s, 3H), 2.72 (q, J=7.5 Hz, 2H), 2.94 (s, 3H), 3.14-3.33 (m, 2H), 3.84-3.92 (m, 3H), 3.99 (s br, 2H), 4.25-4.35 (m, 1H), 4.97 (hept, J=6.5 Hz), 5.58 (s br, 1H), 7.00 (s, 1H), 7.06 (s, 1H), 7.79 (s, 1H), 7.82 (s, 1H).

Example 130

$^1$H NMR (CDCl$_3$): δ 1.24 (d, J=6.8 Hz, 6H), 1.32 (t, J=7.5 Hz, 3H), 2.39 (s, 3H), 2.51 (s, 3H), 2.75 (q, J=7.5 Hz, 2H), 2.93 (s br, 1H), 2.97 (s, 3H), 3.45-3.57 (m, 2H), 3.76-3.93 (m, 3H), 4.17-4.24 (m, 3H), 4.93-5.06 (m, 1H), 7.05 (s, 1H), 7.08 (t br, J=5.3 Hz, 1H), 7.12 (s, 1H), 7.87 (s, 1H), 7.88 (s, 1H).

Examples 131 to 132

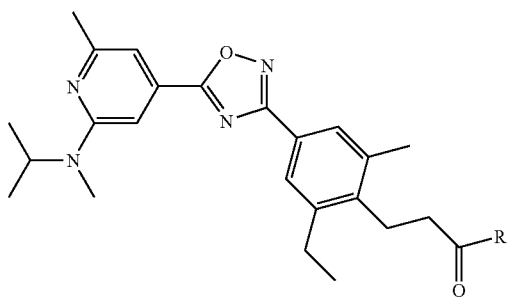

The following Examples are prepared starting from Example 25 in analogy to Example 68.

| Example | R | LC-MS $t_R$ (min) | $[M + H]^+$ |
|---|---|---|---|
| 131 | HN— | 0.87 | 436.26 |
| 132 | HN—OH | 0.81 | 466.24 |

Example 131

$^1$H NMR (CDCl$_3$): δ 1.24 (d, J=6.5 Hz, 6H), 1.32 (t, J=7.5 Hz, 3H), 2.34-2.40 (m, 2H), 2.45 (s, 3H), 2.51 (s, 3H), 2.77 (q, J=7.3 Hz, 2H), 2.85 (d, J=4.5 Hz, 3H), 2.97 (s, 3H), 3.07-3.14 (m, 2H), 4.95-5.05 (m, 1H), 5.37 (s br, 1H), 7.06 (s, 1H), 7.14 (s, 1H), 7.84 (s, 1H), 7.86 (s, 1H).

Examples 133 to 139

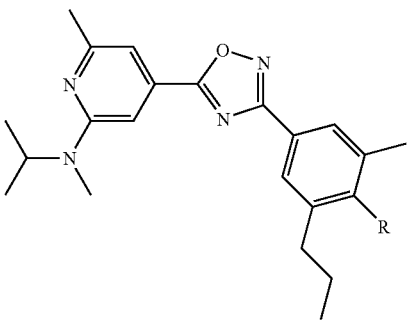

The following Examples are prepared in analogy to previous Examples starting from 2-(isopropyl-methyl-amino)-6-methyl-isonicotinic acid and 4,N-dihydroxy-3-methyl-5-propyl-benzamidine.

| Example | prepared in analogy to Example | R | LC-MS $t_R$ (min) | $[M + H]^+$ |
|---|---|---|---|---|
| 133 | 5 | OH | 1.21* | 381.44 |
| 134 | 3 | ![structure] | 0.83 | 455.25 |
| 135 | 4 | ![structure] | 0.83 | 455.27 |
| 136 | 16 | ![structure] | 0.73 | 454.15 |
| 137 | 16 | ![structure] | 0.73 | 454.33 |
| 138 | 17 | ![structure] | 1.04* | 512.55 |
| 139 | 17 | ![structure] | 1.04* | 512.55 |

Example 133

$^1$H NMR (D$_6$-DMSO): δ 0.94 (t, J=7.0 Hz, 3H), 1.16 (d, J=6.5 Hz, 6H), 1.54-1.65 (m, 2H), 2.27 (s, 3H), 2.43 (s, 3H), 2.64 (t, J=7.0 Hz, 2H), 2.89 (s, 3H), 4.91-5.02 (m, 1H), 5.76 (s, 1H), 7.01 (s, 1H), 7.08 (s, 1H), 7.66 (s, 1H), 7.69 (s, 1H).

The following Examples are prepared in analogy to previous Examples starting from 2-(isopropyl-methyl-amino)-6-methyl-isonicotinic acid and 3-chloro-4,N-dihydroxy-5-methyl-benzamidine.

Examples 140 to 146

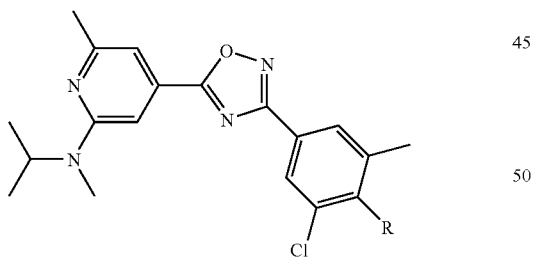

| Example | prepared in analogy to Example | R | LC-MS $t_R$ (min) | $[M + H]^+$ |
|---|---|---|---|---|
| 140 | 5 | OH | 0.88 | 373.11 |
| 141 | 3 | ![structure] | 1.08* | 447.08 |

-continued

| Example | prepared in analogy to Example | R | LC-MS $t_R$ (min) | [M + H]$^+$ |
|---|---|---|---|---|
| 142 | 4 | ![structure: O-CH2-CH(OH)-CH2-OH (S)] | 1.08* | 447.04 |
| 143 | 16 | ![structure: O-CH2-CH(OH)-CH2-NH2 (S)] | 1.00 | 446.07 |
| 144 | 16 | ![structure: O-CH2-CH(OH)-CH2-NH2 (R)] | 1.07* | 446.07 |
| 145 | 17 | ![structure: O-CH2-CH(OH)-CH2-NH-C(O)-CH2-OH (S)] | 0.77 | 504.23 |
| 146 | 17 | ![structure: O-CH2-CH(OH)-CH2-NH-C(O)-CH2-OH (R)] | 1.00* | 504.06 |

Example 146

$^1$H NMR (CDCl$_3$): δ 1.24 (d, J=6.5 Hz, 6H), 2.42 (s, 3H), 2.50 (s, 3H), 2.96 (s, 3H), 3.04 (s br, 1H), 3.53-3.62 (m, 1H), 3.67 (s br, 1H), 3.77-3.85 (m, 1H), 3.96-4.03 (m, 1H), 4.03-4.08 (m, 1H), 4.19-4.26 (m, 3H), 4.93-5.04 (m, 1H), 7.02 (s, 1H), 7.08 (s, 1H), 7.12 (t br, J=5.3 Hz, 1H), 7.91 (s, 1H), 8.05 (s, 1H).

The following Examples are prepared in analogy to previous Examples starting from 2-(isopropyl-methyl-amino)-6-methyl-isonicotinic acid and 3-chloro-4,N-dihydroxy-5-methoxy-benzamidine.

Examples 147 to 153

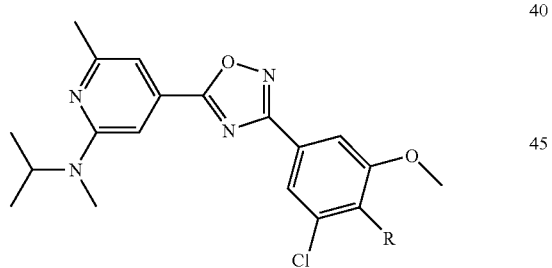

| Example | prepared in analogy to Example | R | LC-MS $t_R$ (min) | [M + H]$^+$ |
|---|---|---|---|---|
| 147 | 5 | OH | 0.85 | 389.06 |
| 148 | 3 | ![structure: O-CH2-CH(OH)-CH2-OH (S)] | 0.78 | 463.14 |
| 149 | 4 | ![structure: O-CH2-CH(OH)-CH2-OH (R)] | 0.78 | 463.16 |

-continued

| Example | prepared in analogy to Example | R | LC-MS $t_R$ (min) | $[M + H]^+$ |
|---|---|---|---|---|
| 150 | 16 | ![O~~~OH~~~NH2 (S)] | 0.68 | 462.18 |
| 151 | 16 | ![O~~~OH~~~NH2 (R)] | 0.68 | 462.12 |
| 152 | 17 | ![O~~~OH~~~NH-C(O)-CH2OH (S)] | 0.79 | 519.96 |
| 153 | 17 | ![O~~~OH~~~NH-C(O)-CH2OH (R)] | 0.79 | 519.96 |

Example 149

$^1$H NMR (CDCl$_3$): δ 1.24 (d, J=6.5 Hz, 6H), 2.21 (t, J=5.8 Hz, 1H), 2.52 (s, 3H), 2.97 (s, 3H), 3.36 (d, J=3.5 Hz, 1H), 3.76-3.90 (m, 2H), 4.03 (s, 3H), 4.06-4.18 (m, 2H), 4.35 (dd, J=9.8, 2.0 Hz, 1H), 4.95-5.06 (m, 1H), 7.04 (s, 1H), 7.11 (s, 1H), 7.65 (s, 1H), 7.89 (s, 1H).

Examples 154 to 160

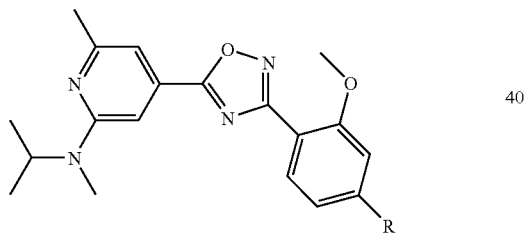

The following Examples are prepared in analogy to previous Examples starting from 2-(isopropyl-methyl-amino)-6-methyl-isonicotinic acid and 4,N-dihydroxy-2-methoxy-benzamidine.

| Example | prepared in analogy to Example | R | LC-MS $t_R$ (min) | $[M + H]^+$ |
|---|---|---|---|---|
| 154 | 5 | OH | 0.75 | 355.14 |
| 155 | 3 | ![O~~~OH~~~OH (S)] | 0.71 | 429.25 |
| 156 | 4 | ![O~~~OH~~~OH (R)] | 0.71 | 429.24 |
| 157 | 16 | ![O~~~OH~~~NH2] | 0.64 | 428.16 |

-continued

| Example | prepared in analogy to Example | R | LC-MS t_R (min) | [M + H]+ |
|---|---|---|---|---|
| 158 | 16 | 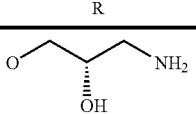 | 0.64 | 428.23 |
| 159 | 17 | 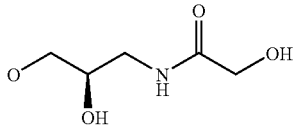 | 0.70 | 486.28 |
| 160 | 17 | 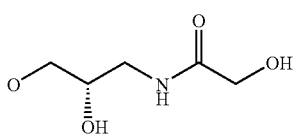 | 0.71 | 486.28 |

Example 158

$^1$H NMR (CDCl$_3$): δ 1.23 (d, J=6.8 Hz, 6H), 2.50 (s, 3H), 2.91 (dd, J=12.8, 7.0 Hz, 1H), 2.95 (s, 3H), 3.05 (dd, J=12.8, 4.0 Hz, 1H), 3.96-4.05 (m, 4H), 4.06-4.13 (m, 2H), 4.94-5.04 (m, 1H), 6.62-6.70 (m, 2H), 7.05 (s, 1H), 7.12 (s, 1H), 8.08 (d, J=9.3 Hz, 1H).

Examples 161 to 167

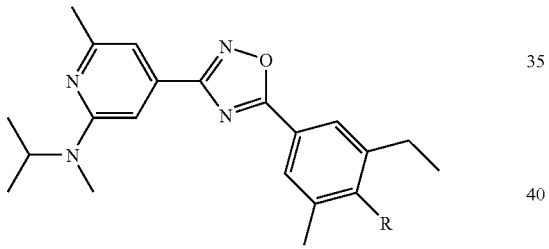

The following Examples are prepared in analogy to previous Examples starting from N-hydroxy-2-(isopropyl-methyl-amino)-6-methyl-isonicotinamidine and 3-ethyl-4-hydroxy-5-methyl-benzoic acid.

| Example | prepared in analogy to Example | R | LC-MS t_R (min) | [M + H]+ |
|---|---|---|---|---|
| 161 | 5 | OH | 0.88 | 367.16 |
| 162 | 3 | 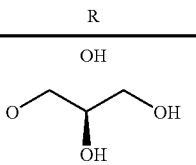 | 0.78 | 441.27 |
| 163 | 4 | 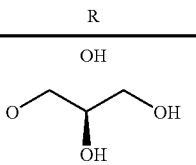 | 0.78 | 441.27 |
| 164 | 16 | 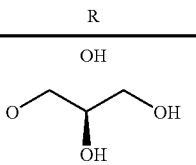 | 0.72 | 440.30 |
| 165 | 16 | 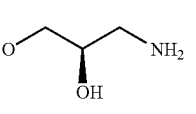 | 0.72 | 440.30 |

-continued

| Example | prepared in analogy to Example | R | LC-MS t$_R$ (min) | [M + H]$^+$ |
|---|---|---|---|---|
| 166 | 17 | 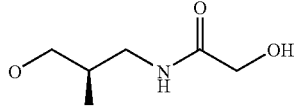 | 0.77 | 498.22 |
| 167 | 17 | 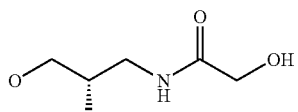 | 0.77 | 498.21 |

Example 162

$^1$H NMR (CDCl$_3$): δ 1.23 (d, J=6.8 Hz, 6H), 1.34 (t, J=7.5 Hz, 3H), 2.07 (s br, 1H), 2.43 (s, 3H), 2.50 (s, 3H), 2.72 (s br, 1H), 2.79 (q, J=7.5 Hz, 2H), 2.96 (s, 3H), 3.82-4.01 (m, 4H), 4.14-4.22 (m, 1H), 5.00 (hept, J=6.3 Hz, 1H), 7.06 (s, 1H), 7.12 (s, 1H), 7.94 (s, 1H), 7.95 (s, 1H).

Examples 168 to 174

The following Examples are prepared in analogy to previous Examples starting from 2-(isopropyl-methyl-amino)-6-methyl-isonicotinic acid and 4-benzyloxy-3-ethyl-5-methyl-benzoic acid hydrazide.

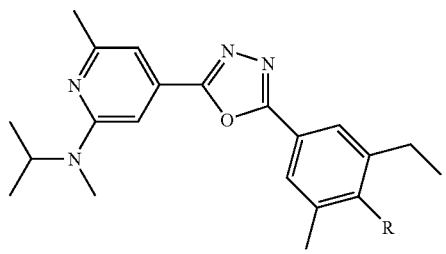

| Example | prepared in analogy to Example | R | LC-MS t$_R$ (min) | [M + H]$^+$ |
|---|---|---|---|---|
| 168 | 81 | OH | 0.87 | 367.50 |
| 169 | 3 | 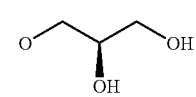 | 0.76 | 441.26 |
| 170 | 4 | 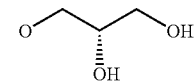 | 0.75 | 441.25 |
| 171 | 16 | 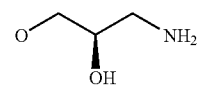 | 0.67 | 440.27 |
| 172 | 16 | 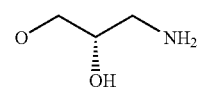 | 0.67 | 440.29 |

| Example | prepared in analogy to Example | R | LC-MS t$_R$ (min) | [M + H]$^+$ |
|---|---|---|---|---|
| 173 | 17 | C(O)CH2OH with OH on chain) | 0.73 | 498.26 |
| 174 | 17 | ![structure](same with stereochemistry) | 0.74 | 498.23 |

Example 174

$^1$H NMR (CDCl$_3$): δ 1.23 (d, J=6.5 Hz, 6H), 1.33 (t, J=7.5 Hz, 3H), 2.41 (s, 3H), 2.44 (s br, 1H), 2.51 (s, 3H), 2.77 (q, J=7.5 Hz, 2H), 2.96 (s, 3H), 3.32 (s br, 1H), 3.50-3.58 (m, 1H), 3.77-3.95 (m, 3H), 4.19-4.27 (m, 3H), 4.96-5.05 (m, 1H), 6.98 (s br, 1H), 7.03 (s, 1H), 7.05 (s, 1H), 7.84 (m, 1H), 7.87 (s, 1H).

Examples 175 to 181

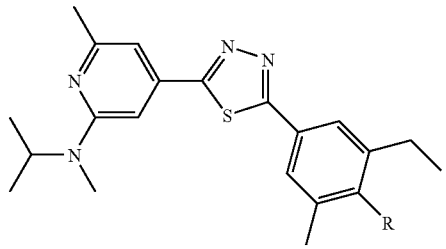

The following Examples are prepared in analogy to previous Examples starting from 2-(isopropyl-methyl-amino)-6-methyl-isonicotinic acid and 4-benzyloxy-3-ethyl-5-methyl-benzoic acid hydrazide.

| Example | prepared in analogy to Example | R | LC-MS t$_R$ (min) | [M + H]$^+$ |
|---|---|---|---|---|
| 175 | 88 | OH | 0.86 | 383.15 |
| 176 | 3 | O\~\~OH, OH | 0.77 | 457.26 |
| 177 | 4 | O\~\~OH, OH (stereo) | 0.78 | 457.28 |
| 178 | 16 | O\~\~NH$_2$, OH | 0.68 | 456.25 |
| 179 | 16 | O\~\~NH$_2$, OH (stereo) | | |

-continued

| Example | prepared in analogy to Example | R | LC-MS $t_R$ (min) | $[M + H]^+$ |
|---|---|---|---|---|
| 180 | 17 | 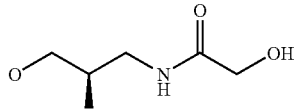 | 0.93* | 514.10 |
| 181 | 17 | 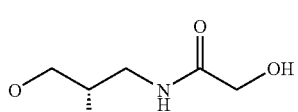 | 0.76 | 514.21 |

Example 179

$^1$H NMR (CDCl$_3$): δ 1.22 (d, J=6.8 Hz, 6H), 1.31 (t, J=7.5 Hz, 3H), 2.38 (s br, 1H), 2.40 (s, 3H), 2.48 (s, 3H), 2.76 (q, J=7.5 Hz, 2H), 2.89-2.97 (m, 4H), 3.04 (dd, J=12.8, 4.0 Hz, 1H), 3.85-3.89 (m, 2H), 3.97-4.04 (m, 1H), 4.99 (hept, J=6.0 Hz, 1H), 6.89 (s, 1H), 6.95 (s, 1H), 7.70 (s, 1H), 7.73 (s, 1H).

The following Examples are prepared in analogy to previous Examples starting from 2-methyl-6-pyrrolidin-1-yl-isonicotinic acid and 4,N-dihydroxy-3-ethyl-5-methyl-benzamidine.

Example 182 to 188

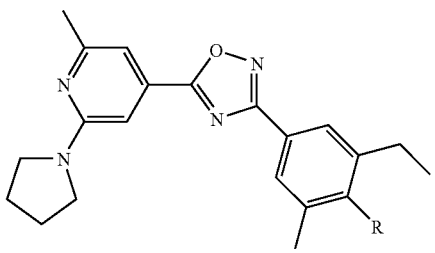

| Example | prepared in analogy to Example | R | LC-MS $t_R$ (min) | $[M + H]^+$ |
|---|---|---|---|---|
| 182 | 5 | OH | 1.12* | 365.07 |
| 183 | 3 | 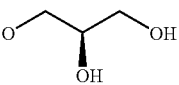 | 1.02* | 439.03 |
| 184 | 4 | 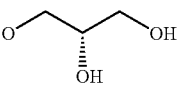 | 1.02* | 439.01 |
| 185 | 16 | 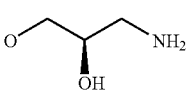 | 1.11* | 438.08 |

-continued

| Example | prepared in analogy to Example | R | LC-MS t$_R$ (min) | [M + H]$^+$ |
|---|---|---|---|---|
| 186 | 16 | ![structure with O-CH2-CH(OH)-CH2-NH2] | 1.10* | 438.05 |
| 187 | 17 | ![structure with O-CH2-CH(OH)-CH2-NH-C(O)-CH2-OH] | 0.94* | 496.02 |
| 188 | 17 | ![structure with O-CH2-CH(OH)-CH2-NH-C(O)-CH2-OH] | 0.94* | 496.02 |

Example 188

$^1$H NMR (CDCl$_3$): δ 1.32 (t, J=7.3 Hz, 3H), 2.02-2.11 (m, 4H), 2.38 (s, 3H), 2.52 (s, 3H), 2.74 (q, J=7.5 Hz, 2H), 3.12 (s br, 1H), 3.48-3.61 (m, 6H), 3.75-3.93 (m, 3H), 4.16-4.24 (m, 3H), 6.90 (s, 1H), 7.07-7.15 (m, 2H), 7.85 (s, 1H), 7.87 (s, 1H).

The following Examples are prepared in analogy to previous Examples starting from 2-ethyl-6-(dimethylamino)-isonicotinic acid and 4,N-dihydroxy-3-ethyl-5-methyl-benzamidine.

Examples 189 to 192

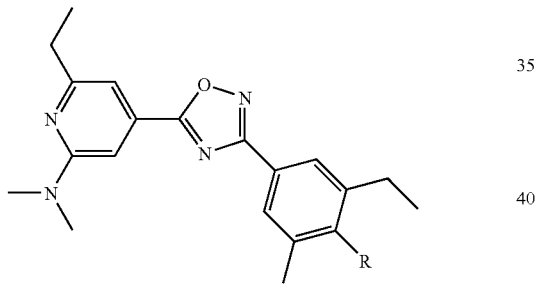

| Example | prepared in analogy to Example | R | LC-MS t$_R$ (min) | [M + H]$^+$ |
|---|---|---|---|---|
| 189 | 5 | OH | 0.88 | 353.14 |
| 190 | 4 | ![structure O-CH2-CH(OH)-CH2-OH] | 0.78 | 427.09 |
| 191 | 16 | ![structure O-CH2-CH(OH)-CH2-NH2] | 0.68 | 426.13 |
| 192 | 17 | ![structure O-CH2-CH(OH)-CH2-NH-C(O)-CH2-OH] | 0.75 | 484.24 |

Example 192

¹H NMR (CDCl₃): δ 1.31 (t, J=8.0 Hz, 3H), 1.35 (t, J=7.5 Hz, 3H), 2.38 (s, 3H), 2.70-2.83 (m, 4H), 3.19 (s, 6H), 3.47-3.55 (m, 1H), 3.74-3.92 (m, 4H), 4.16-4.23 (m, 3H), 7.06 (s, 1H), 7.14 (s, 1H), 7.22 (t, J=5.5 Hz, 1H), 7.85 (s, 1H), 7.87 (s, 1H).

Examples 193-196

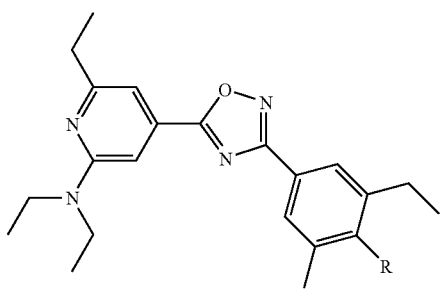

The following Examples are prepared in analogy to previous Examples starting from 2-ethyl-6-(diethylamino)-isonicotinic acid and 4,N-dihydroxy-3-ethyl-5-methyl-benzamidine.

Example 193

¹H NMR (CDCl₃): δ 1.26 (t, J=7.0 Hz, 6H), 1.30-1.39 (m, 6H), 2.36 (s, 3H), 2.70-2.81 (m, 4H), 3.63 (q, J=6.8 Hz, 4H), 5.00 (s, 1H), 7.02 (s, 1H), 7.11 (s, 1H), 7.85 (s, 2H)

Examples 197 to 204

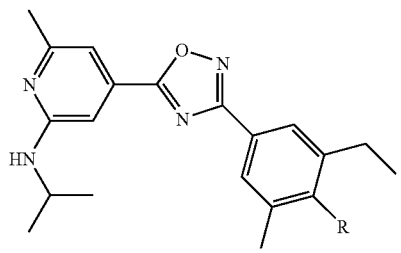

The following Examples are prepared in analogy to previous Examples starting from 2-methyl-6-(isopropylamino)-isonicotinic acid and 4,N-dihydroxy-3-ethyl-5-methyl-benzamidine or 3-[2-ethyl-4-(N-hydroxycarbamimidoyl)-6-methyl-phenyl]-propionic acid tert-butyl ester.

| Example | prepared in analogy to Example | R | LC-MS $t_R$ (min) | [M + H]⁺ |
|---|---|---|---|---|
| 193 | 5 | OH | 0.96 | 381.15 |
| 194 | 4 | 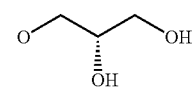 | 0.87 | 455.23 |
| 195 | 16 | 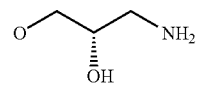 | 0.75 | 454.28 |
| 196 | 17 | 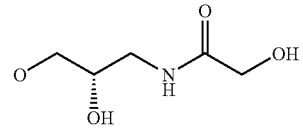 | 0.82 | 512.33 |

| Example | prepared in analogy to Example | R | $t_R$ (min) | $[M + H]^+$ |
|---|---|---|---|---|
| 197 | 5 | OH | 0.85 | 353.16 |
| 198 | 3 | ![structure] | 0.78 | 427.17 |
| 199 | 4 | ![structure] | 0.79 | 427.17 |
| 200 | 16 | ![structure] | 0.69 | 426.24 |
| 201 | 16 | ![structure] | 0.69 | 426.21 |
| 202 | 17 | ![structure] | 0.75 | 484.31 |
| 203 | 17 | ![structure] | 0.75 | 484.32 |
| 204++ | 8 | —CH₂—CH₂—COOH | 0.84 | 409.18 |

++Reference Example

Example 204

$^1$H NMR (D$_6$-DMSO): δ 1.18 (d, J=6.5 Hz, 6H), 1.23 (t, J=7.5 Hz, 3H), 2.36-2.43 (m, 8H), 2.74 (q, J=8.0 Hz, 2H), 2.90-2.98 (m, 2H), 4.03-4.13 (m, 1H), 6.82 (d, J=8.0 Hz, 1H), 6.98 (s, 1H), 7.00 (s, 1H), 7.73 (s, 1H), 7.74 (s, 1H), 12.28 (s).

Examples 205 to 211

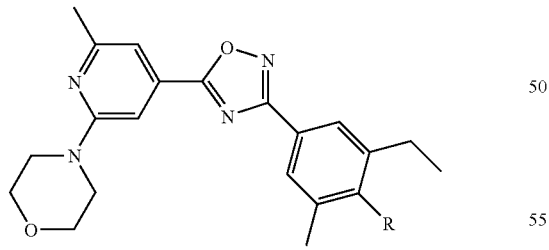

The following Examples are prepared in analogy to previous Examples starting from 2-methyl-6-morpholin-4-yl-isonicotinic acid and 4,N-dihydroxy-3-ethyl-5-methyl-benzamidine.

| Example | prepared in analogy to Example | R | $t_R$ (min) | $[M + H]^+$ |
|---|---|---|---|---|
| 205 | 5 | OH | 0.98 | 381.15 |

-continued

| Example | prepared in analogy to Example | R | LC-MS $t_R$ (min) | [M + H]$^+$ |
|---|---|---|---|---|
| 206 | 3 | (structure: glycerol ether, R-OH) | 0.89 | 455.26 |
| 207 | 4 | (structure: glycerol ether, S-OH) | 0.88 | 455.27 |
| 208 | 16 | (structure: amino-diol, R) | 0.77 | 454.28 |
| 209 | 16 | (structure: amino-diol, S) | 0.77 | 454.28 |
| 210 | 17 | (structure: glycolamide, R) | 0.85 | 512.28 |
| 211 | 17 | (structure: glycolamide, S) | 0.85 | 512.27 |

Example 207

$^1$H NMR (CDCl$_3$): δ 1.33 (t, J=7.5 Hz, 3H), 2.08 (s br, 1H), 2.41 (s, 3H), 2.54 (s, 3H), 2.73 (s, 1H), 2.77 (q, J=7.3 Hz, 2H), 3.62-3.70 (m, 4H), 3.81-3.99 (m, 8H), 4.13-4.21 (m, 1H), 7.20 (s, 1H), 7.28 (s, 1H), 7.87 (s, 1H), 7.89 (s, 1H).

Examples 212 and 213

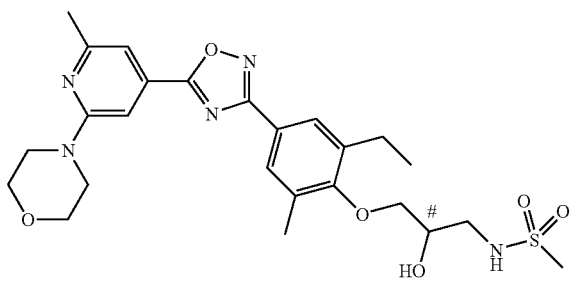 [SMILES: CCc1cc(-c2noc(-c3cc(C)nc(N4CCOCC4)c3)n2)cc(C)c1OCC(O)CNS(C)(=O)=O]

The following Examples are prepared in analogy to Example 59 starting from previous Examples.

| Example | starting from Example | # Chirality | LC-MS $t_R$ (min) | [M + H]$^+$ |
|---|---|---|---|---|
| 212 | 208 | R | 0.92 | 532.23 |
| 213 | 209 | S | 0.92 | 532.23 |

Example 214 (Reference Example)

3-{2-Ethyl-6-methyl-4-[5-(2-methyl-6-morpholin-4-yl-pyridin-4-yl)-[1,2,4]oxadiazol-3-yl]-phenyl}-propionic acid The title compound is prepared in analogy to Example 8 from 2-methyl-6-morpholin-4-yl-isonicotinic acid and 3-[2-ethyl-4-(N-hydroxycarbamimidoyl)-6-methyl-phenyl]-propionic acid tert-butyl ester; LC-MS: $t_R$=0.98 min; [M+1]$^+$ =437.25.

Examples 215 to 218

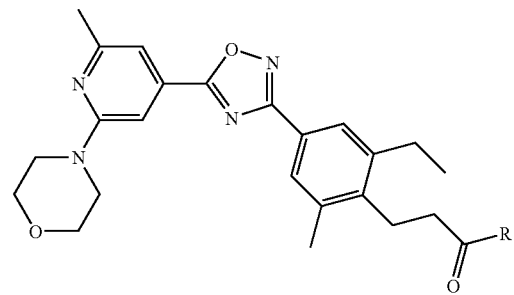

The following Examples are prepared in analogy to previous Examples staring from Example 214.

| Example | prepared in analogy to Example | R | LC-MS t$_R$ (min) | [M + H]$^+$ |
|---|---|---|---|---|
| 215 | 68 | HN–CH₂CH₃ | 0.96 | 450.20 |
| 216 | 68 | HN–CH₂CH₂OH | 0.88 | 480.32 |
| 217 | 27 | HN–CH₂CH₂NH₂ | 0.77 | 479.29 |
| 218 | 26 | HN–CH₂CH₂COOH | 0.89 | 508.27 |

Example 216

$^1$H NMR (D$_6$-DMSO): δ 1.23 (t, J=7.5 Hz, 3H), 2.23-2.30 (m, 2H), 2.41 (s, 3H), 2.46 (s, 3H), 2.75 (q, J=7.5 Hz, 2H), 2.86-2.93 (m, 2H), 3.11-3.18 (m, 2H), 3.39-3.44 (m, 2H), 3.54-3.61 (m, 4H), 3.70-3.77 (m, 4H), 4.60 (s br, 1H), 7.24 (s, 1H), 7.25 (s, 1H), 7.75 (s, 2H), 7.92 (t, J=5.3 Hz, 1H).

Examples 219 to 225

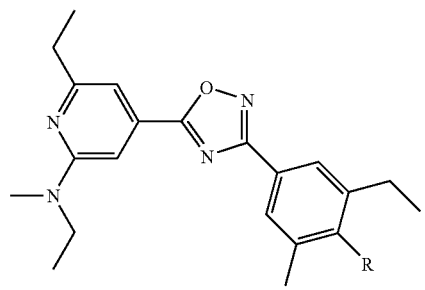

The following Examples are prepared in analogy to previous Examples starting from 2-ethyl-6-(ethyl-methyl-amino)-isonicotinic acid and 4, N-dihydroxy-3-ethyl-5-methyl-benzamidine.

| Example | prepared in analogy to Example | R | LC-MS t$_R$ (min) | [M + H]$^+$ |
|---|---|---|---|---|
| 219 | 5 | OH | 0.91 | 367.18 |
| 220 | 3 | O–CH₂CH(OH)CH₂OH | 1.09* | 441.03 |
| 221 | 4 | O–CH₂CH(OH)CH₂OH | 1.09* | 441.03 |
| 222 | 16 | O–CH₂CH(OH)CH₂NH₂ | 0.92* | 440.06 |
| 223 | 16 | O–CH₂CH(OH)CH₂NH₂ | 0.93 | 439.81 |
| 224 | 17 | O–CH₂CH(OH)CH₂NHC(O)CH₂OH | 1.02* | 498.02 |
| 225 | 17 | O–CH₂CH(OH)CH₂NHC(O)CH₂OH | 1.02* | 498.03 |

Example 225

¹H NMR (CDCl₃): δ 1.20 (t, J=7.0 Hz, 3H), 1.27-1.37 (m, 6H), 2.36 (s, 3H), 2.68-2.81 (m, 4H), 3.13 (s, 3H), 3.51 (m, 2H), 3.68 (q, J=7.0 Hz, 2H), 3.73-3.90 (m, 3H), 4.14-4.21 (m, 3H), 7.01 (s, 1H), 7.09 (s, 1H), 7.34 (t, J=5.8 Hz, 1H), 7.83 (s, 1H), 7.85 (s, 1H).

Example 226

¹H NMR (D₆-DMSO): δ 0.90 (d, J=6.5 Hz, 6H), 1.19 (t, J=7.3 Hz, 3H), 2.02-2.13 (m, 1H), 2.27 (s, 3H), 2.42 (s, 3H), 2.68 (q, J=7.3 Hz, 2H), 3.10 (s, 3H), 3.44 (d, J=7.0 Hz, 2H), 6.99 (s, 1H), 7.07 (s, 1H), 7.68 (s, 2H), 8.94 (s br, 1H).

Examples 226 to 232

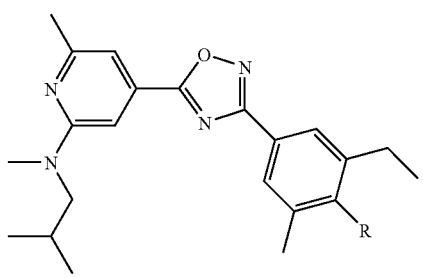

The following Examples are prepared in analogy to previous Examples starting from 2-(isobutyl-methyl-amino)-6-methyl-isonicotinic acid and 4,N-dihydroxy-3-ethyl-5-methyl-benzamidine.

Examples 233 to 235

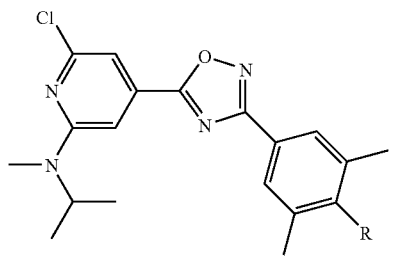

The following Examples are prepared in analogy to previous Examples starting from 2-chloro-6-(isopropyl-methyl-amino)-isonicotinic acid and 4-allyloxy-N-hydroxy-3,5-dimethyl-benzamidine.

| Example | prepared in analogy to Example | R | $t_R$ (min) | $[M + H]^+$ |
|---|---|---|---|---|
| 226 | 5 | OH | 1.24* | 381.18 |
| 227 | 3 | 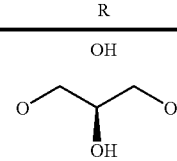 | 1.12* | 455.14 |
| 228 | 4 | 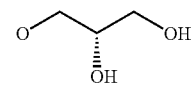 | 1.13* | 455.13 |
| 229 | 16 | 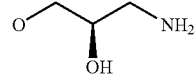 | 0.74 | 454.31 |
| 230 | 16 | 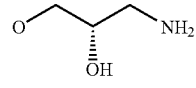 | 0.74 | 454.31 |
| 231 | 17 | 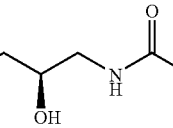 | 1.06* | 512.14 |
| 232 | 17 | 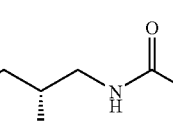 | 1.06* | 512.14 |

| Example | prepared in analogy to Example | R | LC-MS $t_R$ (min) | $[M + H]^+$ |
|---|---|---|---|---|
| 233 | 1 | ![structure: O-CH2-CH(OH)-CH2-OH] | 1.09 | 447.22 |
| 234 | 32 | ![structure: O-CH2-CH(OH)-CH2-NH2] | 0.82 | 445.34 |
| 235 | 32 | ![structure: O-CH2-CH(OH)-CH2-NH-C(O)-CH2-OH] | 1.05 | 504.16 |

Example 235

$^1$H NMR (CD$_3$OD): δ 1.25 (d, J=6.8 Hz, 6H), 2.37 (s, 6H), 2.96 (s, 3H), 3.47 (dd, J=13.6, 7.3 Hz, 1H), 3.66 (dd, J=13.8, 4.5 Hz, 1H), 3.82-3.90 (m, 2H), 4.04 (s, 2H), 4.10-4.17 (m, 1H), 4.84-4.93 (m, 1H), 7.12 (s, 1H), 7.14 (s, 1H), 7.76 (s, 2H).

Example 236 (Reference Example)

4-[5-(2-Diethylamino-6-methyl-pyridin-4-yl)-[1,2,4]oxadiazol-3-yl]-benzoic acid

The title compound is prepared in analogy to Example 8 starting from 4-(N-hydroxycarbamimidoyl)-benzoic acid ethyl ester and 2-diethylamino-6-methyl-isonicotinic acid except that in the final step, the ethyl ester is cleaved under basic conditions (3 N aq. NaOH in THF); LC-MS: $t_R$=0.77 min; [M+1]$^+$=353.09; $^1$H NMR (D$_6$-DMSO): δ 1.16 (t, J=6.8 Hz, 6H), 2.43 (s, 3H), 3.58 (q, J=6.5 Hz, 4H), 7.00 (s, 1H), 7.07 (s, 1H), 8.00 (d, J=8.0 Hz, 2H), 8.04 (d, J=8.0 Hz, 2H).

Examples 237 to 240

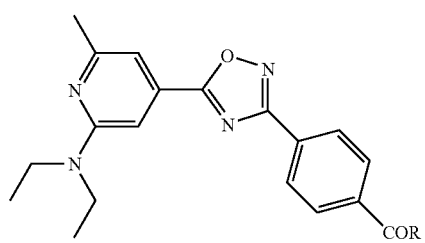

The following Examples are prepared starting from Example 236 in analogy to previous Examples.

| Example | prepared in analogy to Example | R | LC-MS $t_R$ (min) | $[M + H]^+$ |
|---|---|---|---|---|
| 237 | 68 | ![HN-CH2-CH2-OH] | 0.71 | 396.14 |
| 238 | 68 | ![HN-CH2-CH(OH)-CH2-OH] | 0.70 | 426.10 |
| 239 | 26 | ![HN-CH2-C(O)-O-ethyl] | 0.82 | 438.18 |
| 240 | 26 | ![HN-CH2-C(O)-OH] | 0.73 | 410.15 |

Example 241 (Reference Example)

{4-[5-(2-Diethylamino-6-methyl-pyridin-4-yl)-[1,2,4]oxadiazol-3-yl]-phenyl}-acetic acid The title compound is prepared in analogy to Example 5 starting from [4-(N-hydroxycarbamimidoyl)-phenyl]-acetic acid and 2-diethylamino-6-methyl-isonicotinic acid; LC-MS: $t_R$=0.78 min; [M+1]$^+$=367.13.

Examples 242 to 244

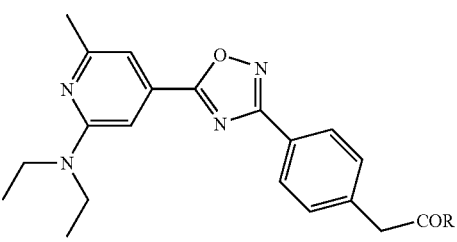

The following Examples are prepared starting from Example 241 in analogy to previous Examples.

| Example | prepared in analogy to Example | R | LC-MS t$_R$ (min) | [M + H]$^+$ |
|---|---|---|---|---|
| 242 | 68 |  | 0.71 | 410.11 |
| 243 | 68 |  | 0.74 | 450.17 |
| 244 | 68 |  | 0.75 | 464.23 |

Example 242

$^1$H NMR (D$_6$-DMSO): δ 1.16 (t, J=6.8 Hz, 6H), 2.43 (s, 3H), 3.15 (q, J=5.5 Hz, 2H), 3.42 (t, J=5.8 Hz, 2H), 3.54 (s, 2H), 3.58 (q, J=7.0 Hz, 4H), 4.69 (s br, 1H), 7.00 (s, 1H), 7.06 (s, 1H), 7.49 (d, J=7.8 Hz, 2H), 8.03 (d, J=7.8 Hz, 2H), 8.14 (t br, J=5.0 Hz, 1H).

Example 245

{4-[5-(2-Diethylamino-6-methyl-pyridin-4-yl)-[1,2,4]oxadiazol-3-yl]-phenyl}-methanol The title compound is prepared in analogy to Example 5 starting from N-hydroxy-4-hydroxymethyl-benzamidine and 2-diethylamino-6-methyl-isonicotinic acid; LC-MS: t$_R$=0.76 min; [M+1]$^+$=339.11.

Example 246

2-{4-[5-(2-Diethylamino-6-methyl-pyridin-4-yl)-[1,2,4]oxadiazol-3-yl]-phenyl}-ethanol The title compound is prepared in analogy to Example 5 starting from N-hydroxy-4-(2-hydroxy-ethyl)-benzamidine and 2-diethylamino-6-methyl-isonicotinic acid; LC-MS: t$_R$=1.07*min; [M+1]$^+$=353.11; $^1$H NMR (CDCl$_3$): δ 1.25 (t, J=6.8 Hz, 6H), 2.50 (s, 3H), 2.98 (t, J=6.3 Hz, 2H), 3.63 (q, J=7.0 Hz, 4H), 3.95 (q, J=6.0 Hz, 2H), 7.02 (s, 1H), 7.10 (s, 1H), 7.41 (d, J=7.5 Hz, 2H), 8.15 (d, J=7.5 Hz, 2H).

Example 247

(4-{3-[4-(2-Amino-ethyl)-phenyl]-[1,2,4]oxadiazol-5-yl}-6-methyl-pyridin-2-yl)-diethyl-amine The title compound is prepared from Example 246 via mesylation, and substitution with azide followed by Staudinger reaction as described for Example 55; LC-MS: t$_R$=0.64 min; [M+1]$^+$=352.11; $^1$H NMR (CDCl$_3$): δ 1.25 (t, J=6.8 Hz, 6H), 2.50 (s, 3H), 2.86 (t, J=6.5 Hz, 2H), 3.06 (t, J=6.5 Hz, 2H), 3.63 (q, J=7.0 Hz, 4H), 7.02 (s, 1H), 7.10 (s, 1H), 7.38 (d, J=7.8 Hz, 2H), 8.13 (d, J=7.5 Hz, 2H).

Examples 248 and 249

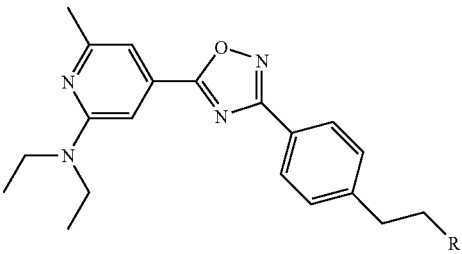

The following Examples are prepared in analogy to previous Examples starting from Example 246.

| Example | prepared in analogy to Example | R | LC-MS t$_R$ (min) | [M + H]$^+$ |
|---|---|---|---|---|
| 248 | 17 |  | 0.89 | 410.15 |
| 249 | 59 |  | 0.81 | 430.14 |

Example 249

$^1$H NMR (CDCl$_3$): δ 1.25 (t, J=7.0 Hz, 6H), 2.50 (s, 3H), 2.90 (s, 3H), 3.00 (t, J=6.5 Hz, 2H), 3.45-3.54 (m, 2H), 3.63 (q, J=7.0 Hz, 4H), 4.25 (t br, J=6.3 Hz, 1H), 7.01 (s, 1H), 7.10 (s, 1H), 7.40 (d, J=8.0 Hz, 2H), 8.17 (d, J=8.0 Hz, 2H).

Example 250

2-(2-{4-[5-(2-Diethylamino-6-methyl-pyridin-4-yl)-[1,2,4]oxadiazol-3-yl]-phenyl}-ethylamino)-ethanol The title compound is prepared from Example 246 in analogy to Example 55 by reacting the mesylate intermediate with ethanolamine rather than sodium azide; LC-MS: t$_R$=1.16*min; [M+1]$^+$=396.11; $^1$H NMR (CDCl$_3$): δ 1.25 (t, J=7.0 Hz, 6H), 1.90 (s br, 2H), 2.50 (s, 3H), 2.83 (t, J=4.8 Hz, 2H), 2.88-2.94 (m, 2H), 2.95-3.02 (m, 2H), 3.58-3.70 (m, 6H), 7.01 (s, 1H), 7.10 (s, 1H), 7.37 (d, J=7.8 Hz, 2H), 8.12 (d, J=7.5 Hz, 2H).

Example 251

(2-{4-[5-(2-Diethylamino-6-methyl-pyridin-4-yl)-[1,2,4]oxadiazol-3-yl]-phenyl}-ethylamino)-acetic acid ethyl ester The title compound is prepared from Example 246 in analogy to Example 55 by reacting the mesylate intermediate with glycine ethyl ester rather than sodium azide; LC-MS: t$_R$=0.69 min; [M+1]$^+$=438.20.

Example 252

(2-{4-[5-(2-Diethylamino-6-methyl-pyridin-4-yl)-[1,2,4]oxadiazol-3-yl]-phenyl}-ethylamino)-acetic acid The title compound is obtained as a hydrochloride salt upon treating Example 251 with 4 N HCl in dioxane; LC-MS: $t_R$=0.67*min; [M+1]$^+$=410.11; $^1$H NMR (D$_2$O): δ 1.26 (t, J=7.0 Hz, 6H), 2.53 (s, 3H), 3.12 (t, J=7.5 Hz, 2H), 3.40 (t, J=7.3 Hz, 2H), 3.67 (q, J=7.0 Hz, 4H), 3.78 (s, 2H), 7.18 (s, 1H), 7.50 (d, J=7.8 Hz, 2H), 7.58 (s, 1H), 8.01 (d, J=7.5 Hz, 2H).

Example 253

Diethyl-{6-methyl-4-[3-(4-propoxy-phenyl)-[1,2,4]oxadiazol-5-yl]-pyridin-2-yl}-amine The title compound is prepared in analogy to Example 5 starting from N-hydroxy-4-propoxy-benzamidine and 2-diethylamino-6-methyl-isonicotinic acid; LC-MS: $t_R$=1.41*min; [M+1]$^+$=367.09.

Example 254

{4-[3-(2,3-Dimethoxy-phenyl)-[1,2,4]oxadiazol-5-yl]-6-methyl-pyridin-2-yl}-diethyl-amine The title compound is prepared in analogy to Example 5 starting from N-hydroxy-2,3-dimethoxy-benzamidine and 2-diethylamino-6-methyl-isonicotinic acid; LC-MS: $t_R$=1.16*min; [M+1]$^+$=369.03.

Example 255 (Reference Example)

rac-1-{4-[5-(2-Diethylamino-6-methyl-pyridin-4-yl)-[1,2,4]oxadiazol-3-yl]-phenyl}-ethane-1,2-diol The title compound is prepared in analogy to Example 1 starting from N-hydroxy-4-vinyl-benzamidine and 2-diethylamino-6-methyl-isonicotinic acid; LC-MS: $t_R$=0.69 min, [M+1]$^+$=369.11.

Example 256 rac-1-{4-[5-(2-Diethylamino-6-methyl-pyridin-4-yl)-[1,2,4]oxadiazol-3-yl]-phenyl}-2-(2-hydroxy-ethylamino)-ethanol Example 255 is transformed into the corresponding mesylate and then reacted with ethanolamine in analogy to the procedures given in Example 55 to give the title compound; $t_R$=0.61 min, [M+1]$^+$=412.18.

Example 257 rac-N-(2-{4-[5-(2-Diethylamino-6-methyl-pyridin-4-yl)-[1,2,4]oxadiazol-3-yl]-phenyl}-2-hydroxy-ethyl)-methanesulfonamide Example 255 is transformed into the corresponding mesylate and then reacted with methane sulfonamide potassium salt in analogy to the procedures given in Example 55 to give the title compound; $t_R$=0.73 min, [M+1]$^+$=446.14.

Example 258

N-{4-[5-(2-Diethylamino-6-methyl-pyridin-4-yl)-[1,2,4]oxadiazol-2-ethyl-phenyl}-acetamide The title compound is prepared in analogy to Example 5 starting from N-[2-ethyl-4-(N-hydroxycarbamimidoyl)-phenyl]-acetamide and 2-diethylamino-6-methyl-isonicotinic acid; LC-MS: $t_R$=0.81 min, [M+1]$^+$=394.15; $^1$H NMR (CDCl$_3$): δ 1.25 (t, J=7.0 Hz, 6H), 1.36 (t, J=7.3 Hz, 3H), 2.28 (s, 3H), 2.50 (s, 3H), 2.73 (q, J=7.3 Hz, 2H), 3.63 (q, J=6.8 Hz, 4H), 7.01 (s, 1H), 7.08-7.16 (m, 2H), 8.03-8.09 (m, 2H), 8.13-8.21 (m, 1H).

Example 259

GTPγS Assay to Determine Ec$_{50}$ Values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$(Fluka, 63064), 0.1% BSA (Calbiochem, 126609), 1 µM GDP (Sigma, G-7127), 2.5% DMSO (Fluka, 41644), 50 µM $^{35}$S-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of $^{35}$S-GTPγS. After addition of 50 µl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 µl MicroScint20 (Packard Biosciences, order#6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay. Agonistic activities (EC$_{50}$ values) of 206 from 258 exemplified compounds have been measured (the compounds of Examples 16, 18, 35, 36, 39, 48, 74, 81, 84, 85, 88, 91, 92, 96, 99, 100, 106, 107, 119, 122, 136, 137, 143, 144, 154, 161, 168, 171, 172, 175, 182, 185, 186, 191, 195, 197, 200, 201, 205, 222, 223, 229, 230, and 234 have not been measured). The compounds of Examples 34, 90, 176, 178, 179, 208 and 209 showed EC$_{50}$ values of greater than 10 µM. All the other measured compounds exhibit EC$_{50}$ values in the range of 0.1 to 9180 nM with an average of 344 nM. Agonistic activities of some compounds of formula (I) are displayed in Table 1.

TABLE 1

| Compound of Example | EC$_{50}$ [nM] |
|---|---|
| 15 | 1.2 |
| 17 | 1.3 |
| 21 | 3.6 |
| 22 | 0.7 |
| 26 | 2.6 |
| 32 | 1.2 |
| 66 | 6.2 |
| 79 | 1.4 |
| 87 | 3.4 |

TABLE 1-continued

| Compound of Example | EC$_{50}$ [nM] |
|---|---|
| 109 | 0.5 |
| 116 | 2.0 |
| 130 | 0.1 |
| 139 | 2.0 |
| 146 | 0.8 |
| 159 | 5.1 |
| 192 | 0.2 |
| 198 | 2.4 |
| 203 | 0.5 |
| 232 | 4.1 |

Example 260

Assessment of In Vivo Efficacy

The efficacy of the compounds of formula (I) is assessed by measuring the circulating lymphocytes after oral administration of 3 to 30 mg/kg of a compound of formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of some compounds of formula (I) to normotensive male Wistar rats as compared to a group of animals treated with vehicle only. Lymphocyte counts 6 h after oral administration have been measured for 39 of the 258 exemplified compounds and are in the range of −82% to −48% with an average of −65%.

TABLE 2

| Compound of Example | Lymphocyte counts |
|---|---|
| 11 | −70 ± 2% |
| 24 | −72 ± 1% |
| 80 | −68 ± 2% |
| 94 | −75 ± 6% |
| 97 | −73 ± 2% |
| 149 | −82 ± 2% |
| 188 | −76 ± 1% |
| 199 | −72 ± 3% |
| 235 | −70 ± 2% |

The invention claimed is:

1. A compound of formula (I),

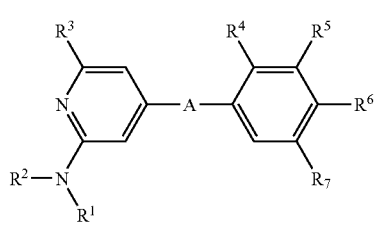

Formula (I)

wherein
A represents

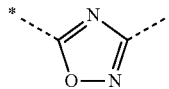 or 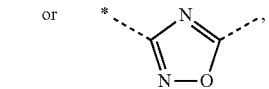, wherein the asterisks indicate the bond that is linked to the pyridine group of formula (I);
$R^1$ represents hydrogen, or $C_{1-3}$-alkyl;
$R^2$ represents $C_{1-4}$-alkyl;
$R^3$ represents $C_{1-4}$-alkyl, or chloro;
$R^4$ represents hydrogen;
$R^5$ represents hydrogen, $C_{1-4}$-alkyl, $C_{1-3}$-alkoxy, or halogen;
$R^6$ represents —CH$_2$—(CH$_2$)$_k$—NR$^{61}$R$^{62}$, —CH$_2$—(CH$_2$)$_k$—NHSO$_2$R$^{63}$, —(CH$_2$)$_n$CH(OH)—CH$_2$—NHSO$_2$R$^{63}$, —CH$_2$—(CH$_2$)$_k$—NHCOR$^{64}$, —(CH$_2$)$_n$CH(OH)—CH$_2$—NHCOR$^{64}$, —CH$_2$—(CH$_2$)$_n$—CONR$^{61}$R$^{62}$, —CO—NHR$^{61}$, —(CH$_2$)$_n$CH(OH)—CH$_2$—NR$^{61}$R$^{62}$, hydroxy-C$_{2-5}$-alkoxy, di-(hydroxy-C$_{1-4}$-alkyl)-C$_{1-4}$-alkoxy, 2,3-dihydroxy-propoxy, 2-hydroxy-3-methoxy-propoxy, —OCH$_2$—(CH$_2$)$_m$—NR$^{61}$R$^{62}$, —OCH$_2$—CH(OH)—CH$_2$—NR$^{61}$R$^{62}$, —OCH$_2$—(CH$_2$)$_m$—NHSO$_2$R$^{63}$, —OCH$_2$—CH(OH)—CH$_2$—NHSO$_2$R$^{63}$, —OCH$_2$—(CH$_2$)$_m$—NHCOR$^{64}$, —OCH$_2$—CH(OH)—CH$_2$—NHCOR$^{64}$, —NR$^{61}$R$^{62}$, —NHCO—R$^{61}$, or —SO$_2$NHR$^{61}$;
$R^{61}$ represents hydrogen, $C_{1-3}$-alkyl, 2-hydroxyethyl, 2-hydroxy-1-hydroxymethyl-ethyl, 2,3-dihydroxypropyl, carboxymethyl, ($C_{1-5}$-alkylcarboxy)methyl, 2-carboxyethyl, 2-($C_{1-5}$-alkylcarboxy)ethyl, or 2-aminoethyl;
$R^{62}$ represents hydrogen;
$R^{63}$ represents $C_{1-3}$-alkyl, methylamino, ethylamino, or dimethylamino;
$R^{64}$ represents hydroxy-$C_{1-2}$-alkyl, or $R^{65}R^{66}$N—$C_{1-2}$-alkyl;
$R^{65}$ and $R^{66}$ independently represent hydrogen, or methyl;
k represents the integer 1, 2, or 3;
m represents the integer 1 or 2;
n represents 0, 1, or 2; and
$R^7$ represents hydrogen, $C_{1-4}$-alkyl, or halogen;
in free or salt form.

2. The compound according to claim 1 wherein A represents

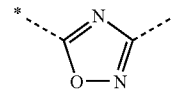

wherein the asterisk indicates the bond that is linked to the pyridine group of formula (I);
in free or salt form.

3. The compound according to claim 1 wherein $R^1$ represents methyl or ethyl;
in free or salt form.

4. The compound according to claim 1 wherein $R^2$ represents $C_{1-3}$-alkyl;
in free or salt form.

5. The compound according to claim 1 wherein $R^3$ represents $C_{1-4}$-alkyl;
in free or salt form.

6. The compound according to claim 1 wherein $R^5$ represents methyl, or ethyl; and $R^7$ represents methyl;
in free or salt form.

7. The compound according to claim 1 wherein $R^6$ represents —CH$_2$—(CH$_2$)$_k$—NHSO$_2$R$^{63}$, —(CH$_2$)$_n$CH(OH)—CH$_2$—NHSO$_2$R$^{63}$, —CH$_2$—(CH$_2$)$_k$—NHCOR$^{64}$, —(CH$_2$)$_n$CH(OH)—CH$_2$—NHCOR$^{64}$, —CH$_2$—(CH$_2$)$_n$—CONR$^{61}$R$^{62}$, —(CH$_2$)$_n$CH(OH)—CH$_2$—NR$^{61}$R$^{62}$, hydroxy-C$_{2-5}$-alkoxy, di-(hydroxy-C$_{1-4}$-alkyl)-C$_{1-4}$-alkoxy, 2,3-dihydroxy-propoxy, 2-hydroxy-3-methoxy-propoxy, —OCH$_2$—(CH$_2$)$_m$—NR$^{61}$R$^{62}$, —OCH$_2$—CH(OH)—CH$_2$—NR$^{61}$R$^{62}$, —OCH$_2$—(CH$_2$)$_m$—NHSO$_2$R$^{63}$, —OCH$_2$—CH(OH)—CH$_2$—NHSO$_2$R$^{63}$, —OCH$_2$—(CH$_2$)$_m$—NHCOR$^{64}$, —OCH$_2$—CH(OH)—CH$_2$—NHCOR$^{64}$, or —NR$^{61}$R$^{62}$;
in free or salt form.

8. The compound according to claim 1 wherein $R^6$ represents —CH$_2$—(CH$_2$)$_n$—CONR$^{61}$R$^{62}$, 2,3-dihydroxy-propoxy, or —OCH$_2$—CH(OH)—CH$_2$—NHCOR$^{64}$;
in free or salt form.

9. The compound according to claim 1 wherein $R^6$ represents 2,3-dihydroxy-propoxy, or —OCH$_2$—CH(OH)—CH$_2$—NHCOR$^{64}$;
in free or salt form.

10. The compound according to claim 1 selected from the group consisting of:
(R)-3-{4-[5-(2-diethylamino-6-ethyl-pyridin-4-yl)-[1,2,4]oxadiazol-3-yl]-2-ethyl-6-methyl-phenoxy}-propane-1,2-diol;
(S)-3-{4-[5-(2-diethylamino-6-ethyl-pyridin-4-yl)-[1,2,4]oxadiazol-3-yl]-2-ethyl-6-methyl-phenoxy}-propane-1,2-diol;
(R)-3-{4-[5-(2-diethylamino-6-methyl-pyridin-4-yl)-[1,2,4]oxadiazol-3-yl]-2-ethyl-6-methyl-phenoxy}-propane-1,2-diol;
(S)-3-{4-[5-(2-diethylamino-6-methyl-pyridin-4-yl)-[1,2,4]oxadiazol-3-yl]-2-ethyl-6-methyl-phenoxy}-propane-1,2-diol;
(R)-3-(2-ethyl-4-{5-[2-(ethyl-methyl-amino)-6-methyl-pyridin-4-yl]-[1,2,4]oxadiazol-3-yl}-6-methyl-phenoxy)-propane-1,2-diol;
(S)-3-(2-ethyl-4-{5-[2-(ethyl-methyl-amino)-6-methyl-pyridin-4-yl]-[1,2,4]oxadiazol-3-yl}-6-methyl-phenoxy)-propane-1,2-diol;
(R)-3-{4-[5-(2-diethylamino-6-methyl-pyridin-4-yl)-[1,2,4]oxadiazol-3-yl]-2,6-dimethyl-phenoxy}-propane-1,2-diol;
(S)-3-{4-[5-(2-diethylamino-6-methyl-pyridin-4-yl)-[1,2,4]oxadiazol-3-yl]-2,6-dimethyl-phenoxy}-propane-1,2-diol;
N—((R)-3-{4-[5-(2-dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide;
N—((S)-3-{4-[5-(2-dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide;
(R)-3-{4-[5-(2-diethylamino-6-methyl-pyridin-4-yl)-[1,2,4]oxadiazol-3-yl]-2-ethyl-6-methyl-phenoxy}-propane-1,2-diol;
(S)-3-{4-[5-(2-diethylamino-6-methyl-pyridin-4-yl)-[1,2,4]oxadiazol-3-yl]-2-ethyl-6-methyl-phenoxy}-propane-1,2-diol;
(R)-3-(4-{5-[2-(ethyl-methyl-amino)-6-methyl-pyridin-4-yl]-[1,2,4]oxadiazol-3-yl}-2,6-dimethyl-phenoxy)-propane-1,2-diol;
(S)-3-(4-{5-[2-(ethyl-methyl-amino)-6-methyl-pyridin-4-yl]-[1,2,4]oxadiazol-3-yl}-2,6-dimethyl-phenoxy)-propane-1,2-diol;
(S)-3-(4-{5-[2-(isopropyl-methyl-amino)-6-methyl-pyridin-4-yl]-[1,2,4]oxadiazol-3-yl}-2,6-dimethyl-phenoxy)-propane-1,2-diol;
N—((S)-3-{4-[5-(2-diethylamino-6-methyl-pyridin-4-yl)-[1,2,4]oxadiazol-3-yl]-2-ethyl-6-methyl-phenoxy}-2-hydroxy-propyl)-2-hydroxy-acetamide;
N—((R)-3-{4-[5-(2-diethylamino-6-methyl-pyridin-4-yl)-[1,2,4]oxadiazol-3-yl]-2-ethyl-6-methyl-phenoxy}-2-hydroxy-propyl)-2-hydroxy-acetamide; and
(S)-3-(2-ethyl-4-{5-[2-(isopropyl-methyl-amino)-6-methyl-pyridin-4-yl]-[1,2,4]oxadiazol-3-yl}-6-methyl-phenoxy)-propane-1,2-diol;
in free or salt form.

11. The compound according to claim 1 selected from the group consisting of:
3-[3-(2-ethyl-4-{5-[2-(isopropyl-methyl-amino)-6-methyl-pyridin-4-yl]-[1,2,4]oxadiazol-3-yl}-6-methyl-phenyl)-propionylamino]-propionic acid;
N—[(R)-3-(2-ethyl-4-{5-[2-(ethyl-methyl-amino)-6-methyl-pyridin-4-yl]-[1,2,4]oxadiazol-3-yl}-6-methyl-phenoxy)-2-hydroxy-propyl]-2-hydroxy-acetamide;
N—[(S)-3-(2-ethyl-4-{5-[2-(ethyl-methyl-amino)-6-methyl-pyridin-4-yl]-[1,2,4]oxadiazol-3-yl}-6-methyl-phenoxy)-2-hydroxy-propyl]-2-hydroxy-acetamide;
N—[(R)-3-(2-ethyl-4-{3-[2-(ethyl-methyl-amino)-6-methyl-pyridin-4-yl]-[1,2,4]oxadiazol-5-yl}-6-methyl-phenoxy)-2-hydroxy-propyl]-2-hydroxy-acetamide;
N—[(S)-3-(2-ethyl-4-{3-[2-(ethyl-methyl-amino)-6-methyl-pyridin-4-yl]-[1,2,4]oxadiazol-5-yl}-6-methyl-phenoxy)-2-hydroxy-propyl]-2-hydroxy-acetamide;
(3-{4-[5-(2-diethylamino-6-methyl-pyridin-4-yl)-[1,2,4]oxadiazol-3-yl]-2-ethyl-6-methyl-phenyl}-propionylamino)-acetic acid;
3-(3-{4-[5-(2-diethylamino-6-methyl-pyridin-4-yl)-[1,2,4]oxadiazol-3-yl]-2-ethyl-6-methyl-phenyl}-propionylamino)-propionic acid;
(R)-3-{4-[3-(2-diethylamino-6-methyl-pyridin-4-yl)-[1,2,4]oxadiazol-5-yl]-2-ethyl-6-methyl-phenoxy}-propane-1,2-diol;
N—((R)-3-{4-[3-(2-diethylamino-6-methyl-pyridin-4-yl)-[1,2,4]oxadiazol-5-yl]-2-ethyl-6-methyl-phenoxy}-2-hydroxy-propyl)-2-hydroxy-acetamide;
N—((S)-3-{4-[3-(2-diethylamino-6-methyl-pyridin-4-yl)-[1,2,4]oxadiazol-5-yl]-2-ethyl-6-methyl-phenoxy}-2-hydroxy-propyl)-2-hydroxy-acetamide;
N—((S)-3-{4-[5-(2-diethylamino-6-methyl-pyridin-4-yl)-[1,2,4]oxadiazol-3-yl]-2-methyl-6-propyl-phenoxy}-2-hydroxy-propyl)-2-hydroxy-acetamide;
(R)-3-{2-chloro-4-[5-(2-diethylamino-6-methyl-pyridin-4-yl)-[1,2,4]oxadiazol-3-yl]-6-methyl-phenoxy}-propane-1,2-diol;
(S)-3-{2-chloro-4-[5-(2-diethylamino-6-methyl-pyridin-4-yl)-[1,2,4]oxadiazol-3-yl]-6-methyl-phenoxy}-propane-1,2-diol;
N—((R)-3-{2-chloro-4-[5-(2-diethylamino-6-methyl-pyridin-4-yl)-[1,2,4]oxadiazol-3-yl]-6-methyl-phenoxy}-2-hydroxy-propyl)-2-hydroxy-acetamide;
N—((S)-3-{2-chloro-4-[5-(2-diethylamino-6-methyl-pyridin-4-yl)-[1,2,4]oxadiazol-3-yl]-6-methyl-phenoxy}-2-hydroxy-propyl)-2-hydroxy-acetamide;
{4-[3-(4-amino-3-chloro-5-methyl-phenyl)-[1,2,4]oxadiazol-5-yl]-6-methyl-pyridin-2-yl}-diethyl-amine;

(R)-3-{2-chloro-4-[5-(2-diethylamino-6-methyl-pyridin-4-yl)-[1,2,4]oxadiazol-3-yl]-6-methoxy-phenoxy}-propane-1,2-diol;

(S)-3-{2-chloro-4-[5-(2-diethylamino-6-methyl-pyridin-4-yl)-[1,2,4]oxadiazol-3-yl]-6-methoxy-phenoxy}-propane-1,2-diol;

(S)-1-amino-3-{2-chloro-4-[5-(2-diethylamino-6-methyl-pyridin-4-yl)-[1,2,4]oxadiazol-3-yl]-6-methoxy-phenoxy}-propan-2-ol;

N—((R)-3-{2-chloro-4-[5-(2-diethylamino-6-methyl-pyridin-4-yl)-[1,2,4]oxadiazol-3-yl]-6-methoxy-phenoxy}-2-hydroxy-propyl)-2-hydroxy-acetamide;

N—((S)-3-{2-chloro-4-[5-(2-diethylamino-6-methyl-pyridin-4-yl)-[1,2,4]oxadiazol-3-yl]-6-methoxy-phenoxy}-2-hydroxy-propyl)-2-hydroxy-acetamide;

(S)-3-{2,6-dichloro-4-[5-(2-diethylamino-6-methyl-pyridin-4-yl)-[1,2,4]oxadiazol-3-yl]-phenoxy}-propane-1,2-diol;

(R)-3-{2,6-dichloro-4-[5-(2-diethylamino-6-methyl-pyridin-4-yl)-[1,2,4]oxadiazol-3-yl]-phenoxy}-propane-1,2-diol;

N—[(R)-3-(2-ethyl-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

N—[(S)-3-(2-ethyl-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

3-(2-ethyl-4-{5-[2-(isopropyl-methyl-amino)-6-methyl-pyridin-4-yl]-[1,2,4]oxadiazol-3-yl}-6-methyl-phenyl)-N-(2-hydroxy-ethyl)-propionamide;

2-hydroxy-N—[(S)-2-hydroxy-3-(4-{5-[2-(isopropyl-methyl-amino)-6-methyl-pyridin-4-yl]-[1,2,4]oxadiazol-3-yl}-2-methyl-6-propyl-phenoxy)-propyl]-acetamide;

(R)-3-(2-chloro-4-{5-[2-(isopropyl-methyl-amino)-6-methyl-pyridin-4-yl]-[1,2,4]oxadiazol-3-yl}-6-methyl-phenoxy)-propane-1,2-diol;

(S)-3-(2-chloro-4-{5-[2-(isopropyl-methyl-amino)-6-methyl-pyridin-4-yl]-[1,2,4]oxadiazol-3-yl}-6-methyl-phenoxy)-propane-1,2-diol;

N—[(R)-3-(2-chloro-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

N—[(S)-3-(2-chloro-4-{5-[2-(isopropyl-methyl-amino)-6-methyl-pyridin-4-yl]-[1,2,4]oxadiazol-3-yl}-6-methyl-phenoxy)-2-hydroxy-propyl]-2-hydroxy-acetamide;

(R)-3-(2-chloro-4-{5-[2-(isopropyl-methyl-amino)-6-methyl-pyridin-4-yl]-[1,2,4]oxadiazol-3-yl}-6-methoxy-phenoxy)-propane-1,2-diol;

(S)-3-(2-chloro-4-{5-[2-(isopropyl-methyl-amino)-6-methyl-pyridin-4-yl]-[1,2,4]oxadiazol-3-yl}-6-methoxy-phenoxy)-propane-1,2-diol;

(R)-1-amino-3-(2-chloro-4-{5-[2-(isopropyl-methyl-amino)-6-methyl-pyridin-4-yl]-[1,2,4]oxadiazol-3-yl}-6-methoxy-phenoxy)-propan-2-ol;

(S)-1-amino-3-(2-chloro-4-{5-[2-(isopropyl-methyl-amino)-6-methyl-pyridin-4-yl]-[1,2,4]oxadiazol-3-yl}-6-methoxy-phenoxy)-propan-2-ol;

N—[(R)-3-(2-chloro-4-{5-[2-(isopropyl-methyl-amino)-6-methyl-pyridin-4-yl]-[1,2,4]oxadiazol-3-yl}-6-methoxy-phenoxy)-2-hydroxy-propyl]-2-hydroxy-acetamide;

N—[(S)-3-(2-chloro-4-{5-[2-(isopropyl-methyl-amino)-6-methyl-pyridin-4-yl]-[1,2,4]oxadiazol-3-yl}-6-methoxy-phenoxy)-2-hydroxy-propyl]-2-hydroxy-acetamide;

(R)-3-(2-ethyl-4-{3-[2-(isopropyl-methyl-amino)-6-methyl-pyridin-4-yl]-[1,2,4]oxadiazol-5-yl}-6-methyl-phenoxy)-propane-1,2-diol;

N—[(S)-3-(2-ethyl-4-{3-[2-(isopropyl-methyl-amino)-6-methyl-pyridin-4-yl]-[1,2,4]oxadiazol-5-yl}-6-methyl-phenoxy)-2-hydroxy-propyl]-2-hydroxy-acetamide;

N—((S)-3-{4-[5-(2-dimethylamino-6-ethyl-pyridin-4-yl)-[1,2,4]oxadiazol-3-yl]-2-ethyl-6-methyl-phenoxy}-2-hydroxy-propyl)-2-hydroxy-acetamide;

(S)-3-{4-[5-(2-diethylamino-6-ethyl-pyridin-4-yl)-[1,2,4]oxadiazol-3-yl]-2-ethyl-6-methyl-phenoxy}-propane-1,2-diol;

(R)-3-{2-ethyl-4-[5-(2-isopropylamino-6-methyl-pyridin-4-yl)-[1,2,4]oxadiazol-3-yl]-6-methyl-phenoxy}-propane-1,2-diol;

(S)-3-{2-ethyl-4-[5-(2-isopropylamino-6-methyl-pyridin-4-yl)-[1,2,4]oxadiazol-3-yl]-6-methyl-phenoxy}-propane-1,2-diol;

N—((R)-3-{2-ethyl-4-[5-(2-isopropylamino-6-methyl-pyridin-4-yl)-[1,2,4]oxadiazol-3-yl]-6-methyl-phenoxy}-2-hydroxy-propyl)-2-hydroxy-acetamide;

N—((S)-3-{2-ethyl-4-[5-(2-isopropylamino-6-methyl-pyridin-4-yl)-[1,2,4]oxadiazol-3-yl]-6-methyl-phenoxy}-2-hydroxy-propyl)-2-hydroxy-acetamide;

N—[(R)-3-(2-ethyl-4-{5-[2-ethyl-6-(ethyl-methyl-amino)-pyridin-4-yl]-[1,2,4]oxadiazol-3-yl}-6-methyl-phenoxy)-2-hydroxy-propyl]-2-hydroxy-acetamide;

N—[(S)-3-(2-ethyl-4-{5-[2-ethyl-6-(ethyl-methyl-amino)-pyridin-4-yl]-[1,2,4]oxadiazol-3-yl}-6-methyl-phenoxy)-2-hydroxy-propyl]-2-hydroxy-acetamide;

N—[(S)-3-(2-ethyl-4-{5-[2-(isobutyl-methyl-amino)-6-methyl-pyridin-4-yl]-[1,2,4]oxadiazol-3-yl}-6-methyl-phenoxy)-2-hydroxy-propyl]-2-hydroxy-acetamide;

(S)-3-(4-{5-[2-chloro-6-(isopropyl-methyl-amino)-pyridin-4-yl]-[1,2,4]oxadiazol-3-yl}-2,6-dimethyl-phenoxy)-propane-1,2-diol;

(R)-3-(4-{5-[2-chloro-6-(isopropyl-methyl-amino)-pyridin-4-yl]-[1,2,4]oxadiazol-3-yl}-2,6-dimethyl-phenoxy)-propane-1,2-diol;

(S)—N-[3-(4-{5-[2-chloro-6-(isopropyl-methyl-amino)-pyridin-4-yl]-[1,2,4]oxadiazol-3-yl}-2,6-dimethyl-phenoxy)-2-hydroxy-propyl]-2-hydroxy-acetamide; and (R)—N-[3-(4-{5-[2-chloro-6-(isopropyl-methyl-amino)-pyridin-4-yl]-[1,2,4]oxadiazol-3-yl}-2,6-dimethyl-phenoxy)-2-hydroxy-propyl]-2-hydroxy-acetamide;

in free or salt form.

12. A pharmaceutical composition comprising a compound according to claim 1 in free or pharmaceutically acceptable salt form, and a pharmaceutically acceptable carrier.

13. The compound according to claim 1, which is N-(3-{4-[5-(2-Diethylamino-6-methyl-pyridin-4-yl)-[1,2,4]oxadiazol-3-yl]-2-ethyl-6-methyl-phenoxy}-(S)-2-hydroxy-propyl)-2-hydroxy-acetamide in free or salt form.

14. A pharmaceutical composition comprising the compound according to claim 13 in free or pharmaceutically acceptable salt form, and a pharmaceutically acceptable carrier.

* * * * *

UNITED STATES PATENT AND TRADEMARK OFFICE
CERTIFICATE OF CORRECTION

PATENT NO. : 8,592,460 B2  Page 1 of 1
APPLICATION NO. : 12/531374
DATED : November 26, 2013
INVENTOR(S) : Bolli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 682 days.

Signed and Sealed this

Twenty-second Day of September, 2015

Michelle K. Lee
*Director of the United States Patent and Trademark Office*